US012663493B2

(12) United States Patent
Dosenbach et al.

(10) Patent No.: US 12,663,493 B2
(45) Date of Patent: Jun. 23, 2026

(54) REAL TIME MONITORING AND PREDICTION OF MOTION IN MRI

(71) Applicants: Washington University, St. Louis, MO (US); Oregon Health and Science University, Portland, OR (US)

(72) Inventors: Nico Dosenbach, St. Louis, MO (US); Jonathan Koller, St. Louis, MO (US); Andrew Van, St. Louis, MO (US); Abraham Snyder, St. Louis, MO (US); Amy Mirro, St. Louis, MO (US); Damien Fair, Portland, OR (US); Eric Earl, Portland, OR (US); Rachel Klein, Portland, OR (US); Oscar Miranda Dominguez, Tigard, OR (US); Anders Perrone, Portland, OR (US)

(73) Assignees: Washington University, St. Louis, MO (US); Oregon Health & Science University, Portland, OR (US)

( * ) Notice: Subject to any disclaimer, the term of this patent is extended or adjusted under 35 U.S.C. 154(b) by 207 days.

(21) Appl. No.: 18/745,232

(22) Filed: Jun. 17, 2024

(65) Prior Publication Data

US 2024/0337718 A1    Oct. 10, 2024

Related U.S. Application Data

(63) Continuation of application No. 18/061,254, filed on Dec. 2, 2022, now Pat. No. 12,050,257, which is a
(Continued)

(51) Int. Cl.
*G01R 33/56* (2006.01)
*A61B 5/055* (2006.01)
(Continued)

(52) U.S. Cl.
CPC ........ *G01R 33/56509* (2013.01); *A61B 5/055* (2013.01); *G01R 33/0041* (2013.01); *G01R 33/4831* (2013.01); *G01R 33/5608* (2013.01)

(58) Field of Classification Search
CPC .......... G01R 33/56509; G01R 33/0041; G01R 33/4831; G01R 33/5608; A61B 5/055;
(Continued)

(56) References Cited

U.S. PATENT DOCUMENTS

| | | | |
|---|---|---|---|
| 6,454,714 B1 | 9/2002 | Ng et al. | |
| 8,126,230 B2 | 2/2012 | Wheaton et al. | |

(Continued)

FOREIGN PATENT DOCUMENTS

| | | |
|---|---|---|
| CN | 101542491 A | 9/2009 |
| CN | 103462612 A | 12/2013 |

(Continued)

OTHER PUBLICATIONS

Rejection Decision issued in Chinese Patent Application No. 20188001741.8 on Oct. 23, 2024, with partial English translation; 43 pgs.

(Continued)

*Primary Examiner* — G.M. A Hyder
(74) *Attorney, Agent, or Firm* — Armstrong Teasdale LLP

(57) ABSTRACT

Methods, computer-readable storage devices, and systems are described for reducing movement of a patient undergoing a magnetic resonance imaging (MRI) scan. One method includes receiving a data frame from the MRI system performing the MRI scan of the patient, comparing the data frame to a reference image to assess motion of a body part of the patient during the MRI scan, generating stimulus to be communicated to the patient during the MRI scan based on a task of the MRI scan and the motion of the body part of the patient during the MRI scan, adjusting the stimulus
(Continued)

during the MRI scan to adjust the task and as the motion of the body part of the patient changes, and communicating the stimulus to the patient during the MRI scan, wherein the sensory feedback includes at least one of a game, a movie, a cartoon, a shape, or an auditory signal.

20 Claims, 54 Drawing Sheets

Related U.S. Application Data continuation of application No. 17/451,539, filed on Oct. 20, 2021, now Pat. No. 11,543,483, which is a continuation of application No. 16/491,413, filed as application No. PCT/US2018/021608 on Mar. 8, 2018, now Pat. No. 11,181,599.

(60) Provisional application No. 62/468,858, filed on Mar. 8, 2017.

(51) Int. Cl.
| | |
|---|---|
| *G01R 33/00* | (2006.01) |
| *G01R 33/483* | (2006.01) |
| *G01R 33/565* | (2006.01) |

(58) Field of Classification Search
CPC ...... A61B 5/7207; G16H 30/40; G16H 40/63; G16H 50/70
See application file for complete search history.

(56) References Cited

U.S. PATENT DOCUMENTS

| | | | |
|---|---|---|---|
| 8,144,201 | B2 | 3/2012 | Lee et al. |
| 8,683,972 | B2 | 4/2014 | Taenzer |
| 10,687,754 | B2 | 6/2020 | Nishimoto et al. |
| 2005/0054910 | A1 | 3/2005 | Tremblay et al. |
| 2005/0283068 | A1 | 12/2005 | Zuccolotto et al. |
| 2006/0100499 | A1 | 5/2006 | Shankaranarayanan et al. |
| 2008/0118126 | A1 | 5/2008 | Sakaguchi |
| 2008/0169808 | A1 | 7/2008 | Taniguchi et al. |
| 2008/0283068 | A1 | 11/2008 | Tsai |
| 2009/0048505 | A1 | 2/2009 | Kuth et al. |
| 2009/0116761 | A1 | 5/2009 | Wheaton et al. |
| 2010/0074475 | A1 | 3/2010 | Chouno |
| 2010/0280353 | A1 | 11/2010 | Roth et al. |
| 2011/0169867 | A1 | 7/2011 | Kniffen et al. |
| 2011/0274334 | A1 | 11/2011 | Zhu et al. |
| 2013/0035588 | A1 | 2/2013 | Shea et al. |
| 2013/0211261 | A1 | 8/2013 | Wang et al. |
| 2014/0111199 | A1 | 4/2014 | Oh et al. |
| 2015/0227702 | A1 | 8/2015 | Krishna et al. |
| 2015/0306340 | A1 | 10/2015 | Giap et al. |
| 2016/0045149 | A1 | 2/2016 | Nishimoto et al. |
| 2016/0120437 | A1 * | 5/2016 | Graham ................ A61B 5/055 600/411 |

FOREIGN PATENT DOCUMENTS

| | | | |
|---|---|---|---|
| CN | 104379059 | A | 2/2015 |
| CN | 106444034 | A | 2/2017 |
| EP | 3106893 | A2 | 12/2016 |
| GB | 2545641 | A | 6/2017 |
| JP | 2003204952 | A | 7/2003 |
| JP | 2008125616 | A | 6/2008 |
| JP | 2009534115 | A | 9/2009 |
| JP | WO2011136031 | A1 | 7/2013 |
| JP | 2014183924 | A | 10/2014 |
| JP | 2014229971 | A | 12/2014 |
| JP | 2015198958 | A | 11/2015 |
| WO | 2006077715 | A1 | 7/2006 |
| WO | 2011133582 | A1 | 10/2011 |
| WO | 2014112242 | A1 | 7/2014 |
| WO | 2022125748 | A1 | 6/2022 |

OTHER PUBLICATIONS

Yao et al., "Development of QRS Complex Detection Algorithm in ECG Signal", Progress in Modern Biomedicine, Jul. 2012, vol. 12, No. 20, pp. 3988-3991, with English Abstract.

Yuan et al., "Computer Simulation of Human Machine Engineering", Beijing University of Aeronautics and Astronautics Press, Apr. 2005, pp. 80-81, with English Translation of the Examiner's Discussion of the Reference.

European Extended Search Report regarding European Patent Application No. 18764375.4 dated Nov. 11, 2022, pp. 1-6.

International Search Report and Written Opinion issued in International Application Serial No. PCT/US2015/021608 mailed Mar. 8, 2019, pp. 1-7.

General Electric Co., BrainWave Introduction: GE User Manual 5500865-1EN, Rev. 1, pp. 5-154 thru 5-273.

Baxter, Leslie C., Special Considerations When Using Functional MRI as a Presurgical Mapping Tool; GE Healthcare MR publication; 2009; pp. 47-49.

Williams, E. J., Clinical language fMRI with real-time monitoring in temporal lobe epilepsy Online processing methods; Epilepsy & Behavior; 2012; vol. 25: pp. 120-124.

Communication Pursuant to Article 34(3); issued on Jul. 6, 2022 for Application No. 18764375.4, pp. 6.

Feng, Liu, "Simulatin and Application Research of Inverse Filtering in Removing Motion Artifacts in Magnetic Resonance Images", Science and Technology Innovation Hearld, Issue 19, Jul. 1, 2013, English Abstract Only.

Guangyao et al., Evaluation of Common Artifacts in MRI, Radiology Practice, 2001, (04), Apr. 25, 2021, English Abstract Only.

Office Action and Search Report issued in Chinese Patent Application No. 201880017041.8, Mar. 29, 2023, pp. 1-29; with partial English translation.

Oakes et al., "Comparison of fMRI Motion Correction Software Tools", Neuroimage, 28(3); 529-543, (2005).

Translation of Japanese Office Action issued for Serial No. 2023-058925, dated Aug. 20, 2024 (5 pages).

* cited by examiner

Final pred. at Each TR

Final Amount of Usable Data

Actual Realization

Mean Error

Mean Error + Std

Mean Error − Std.

Figure 10:
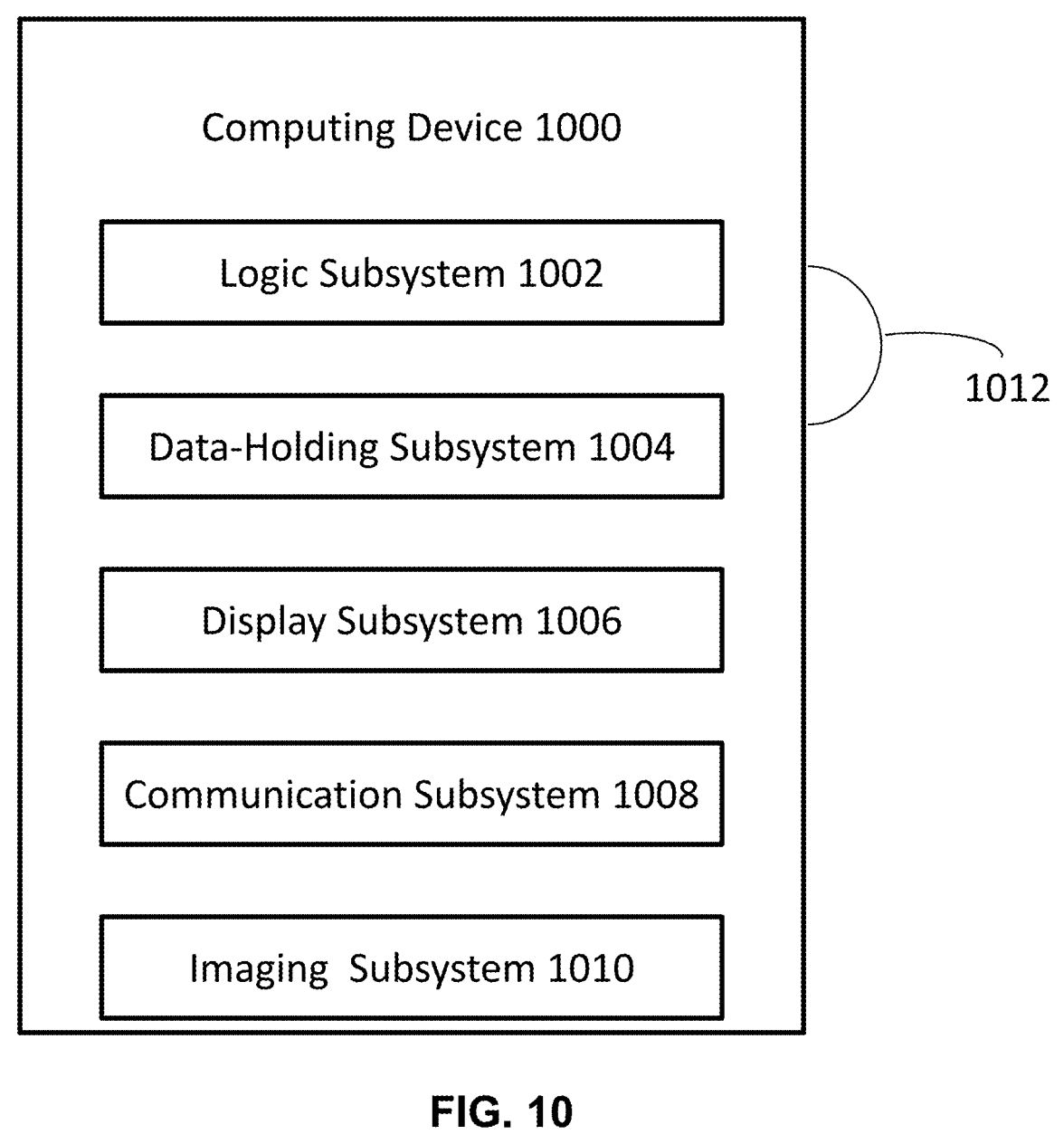

Computing Device 1000

Logic Subsystem 1002

Data-Holding Subsystem 1004

Display Subsystem 1006

Communication Subsystem 1008

Imaging  Subsystem 1010

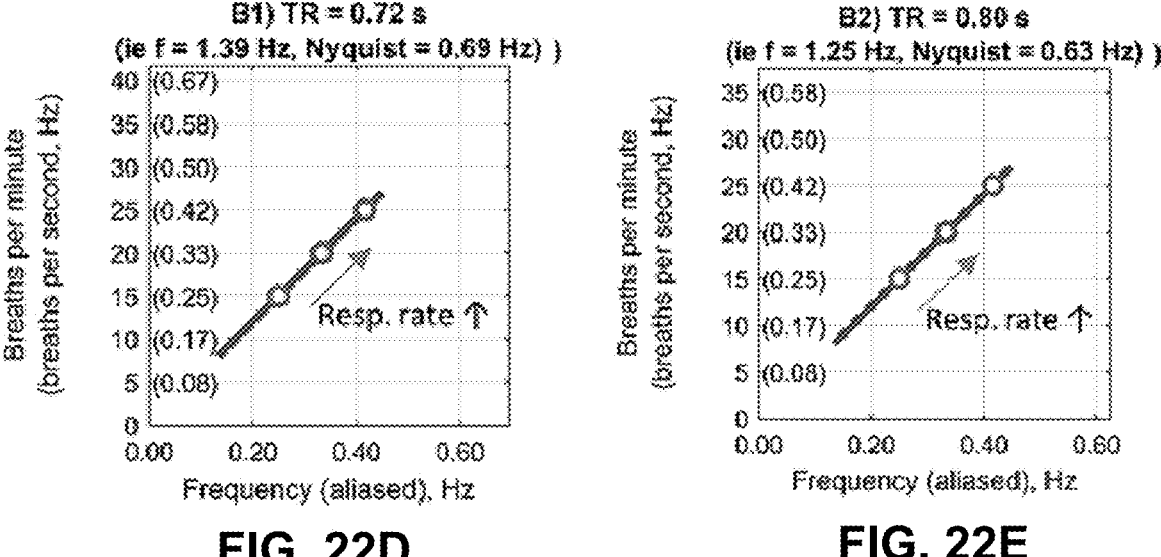
FIG. 22D          FIG. 22E
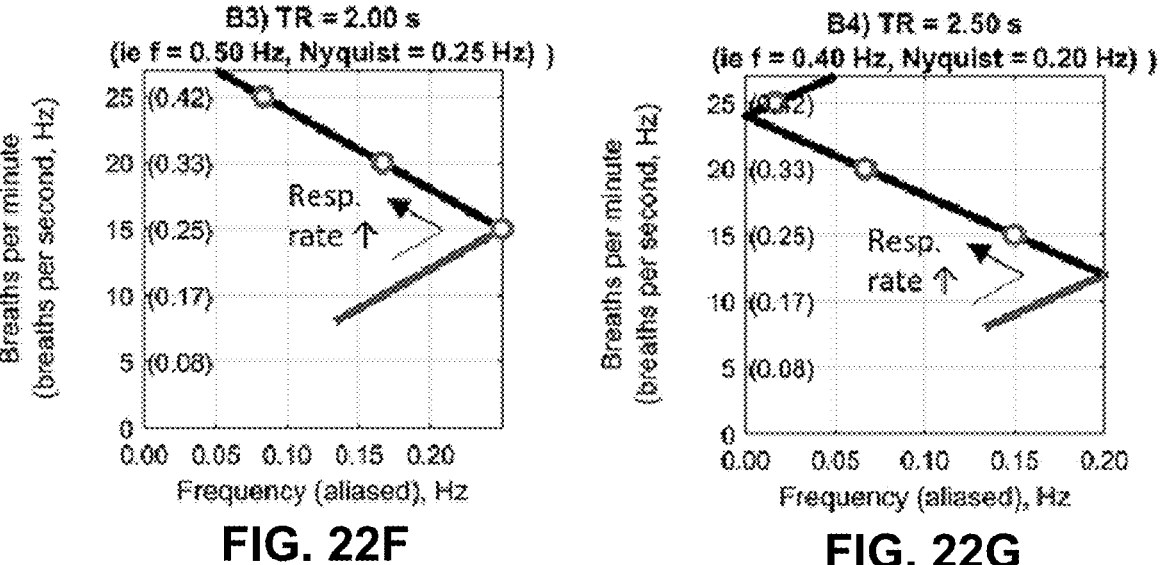
FIG. 22F          FIG. 22G

Post-Filter BVD Plot for Medium Moving ABCD Child

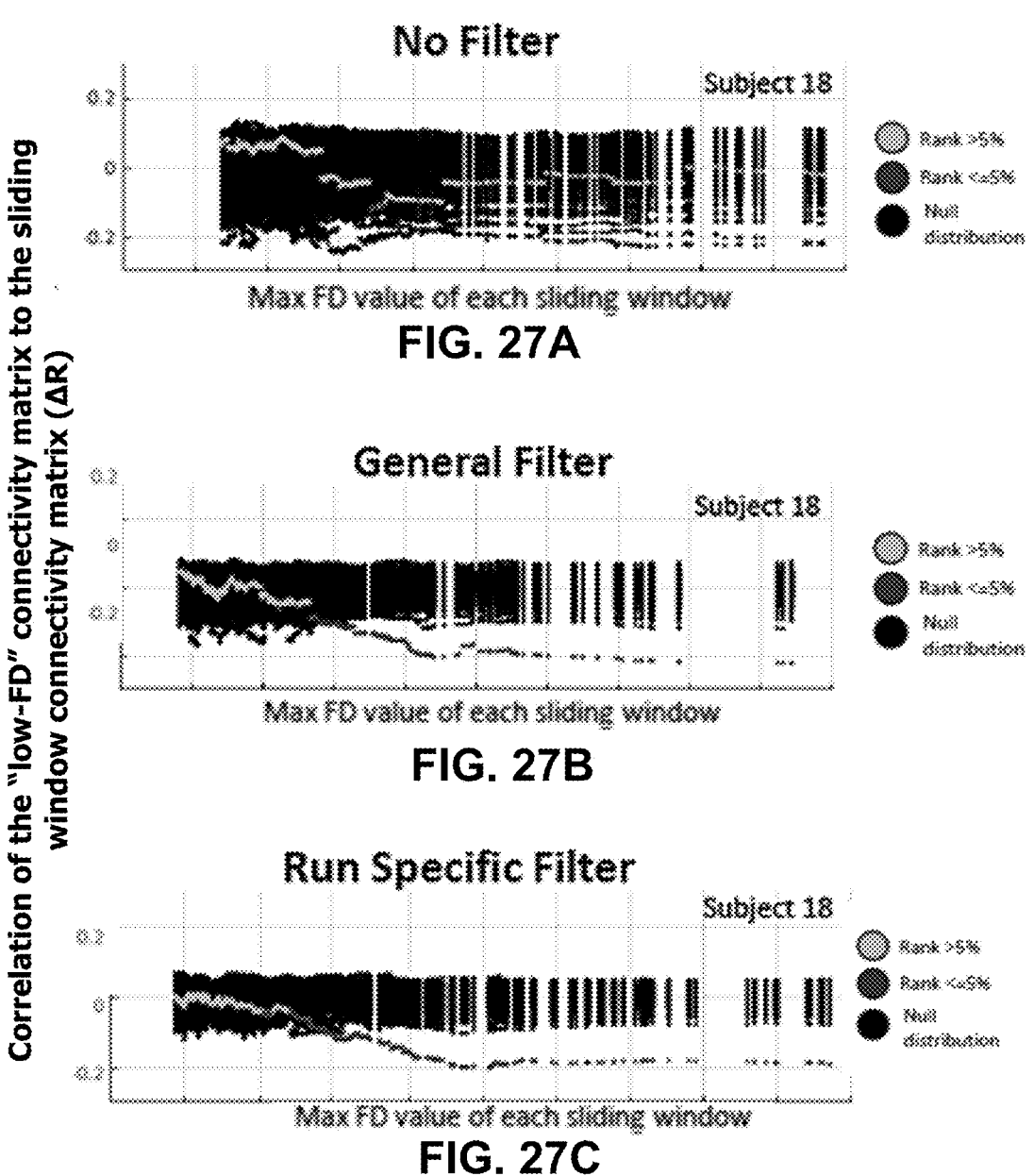

No Filter

Max FD value of each sliding window

General Filter

Max FD value of each sliding window

Run Specific Filter

Max FD value of each sliding window

Rank of Each Point in Relation to the Null Distribution

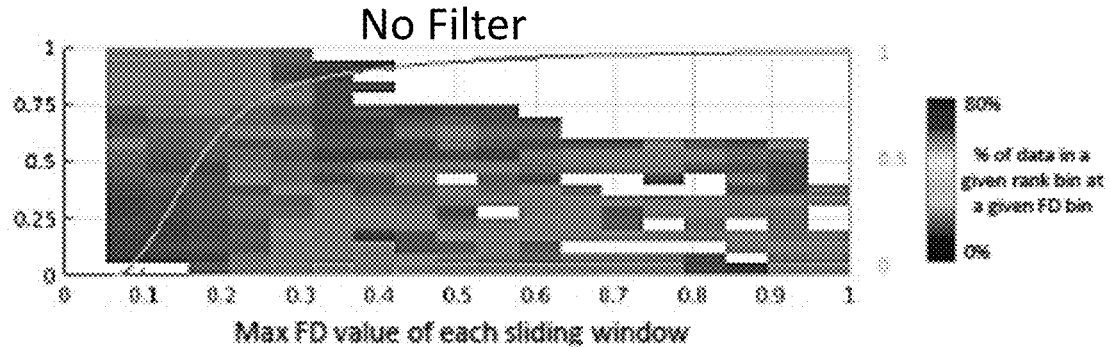
FIG. 27J
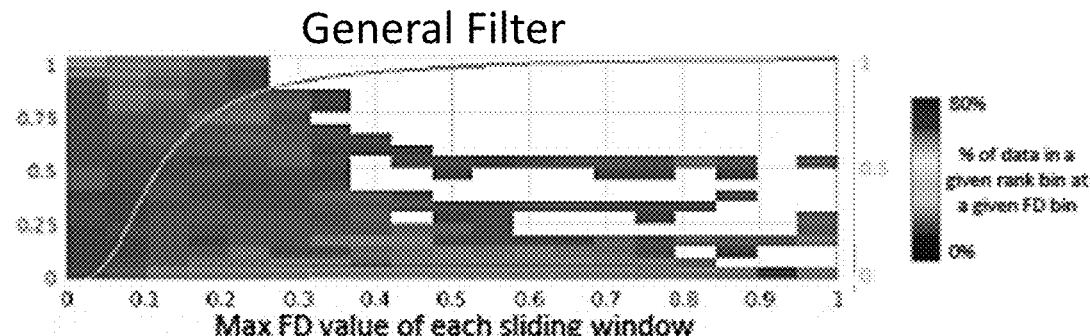
FIG. 27K
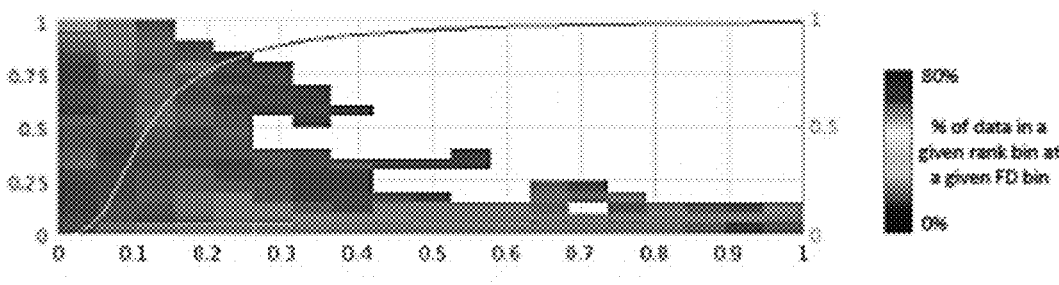
FIG. 27L

Theoretical Plot for Inaccurate
Movement Numbers

Theoretical Plot for Accurate
Movement Numbers

Largest FD value in sliding Window

Largest FD value in sliding Window

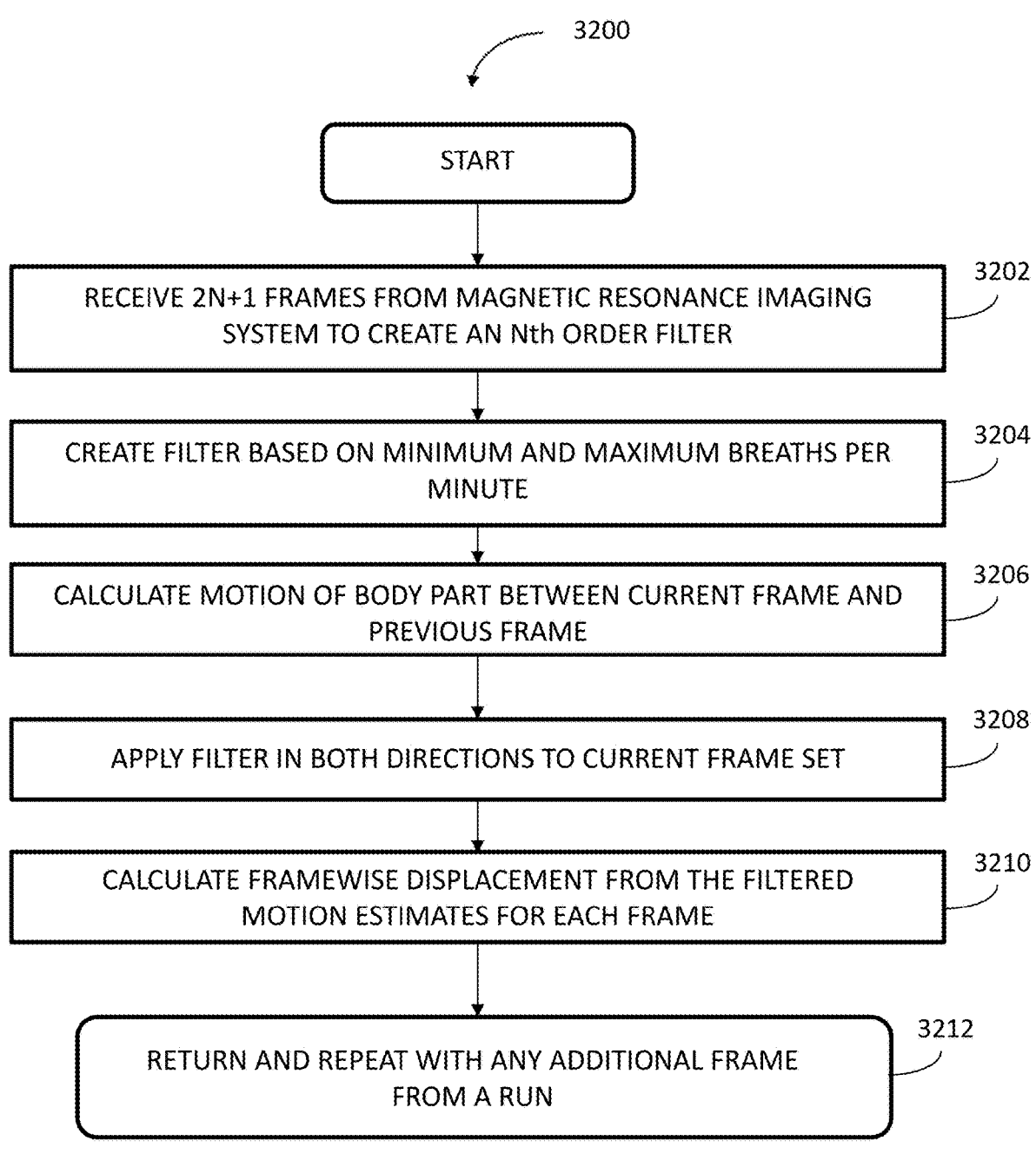

3200

START

RECEIVE 2N+1 FRAMES FROM MAGNETIC RESONANCE IMAGING SYSTEM TO CREATE AN Nth ORDER FILTER — 3202

CREATE FILTER BASED ON MINIMUM AND MAXIMUM BREATHS PER MINUTE — 3204

CALCULATE MOTION OF BODY PART BETWEEN CURRENT FRAME AND PREVIOUS FRAME — 3206

APPLY FILTER IN BOTH DIRECTIONS TO CURRENT FRAME SET — 3208

CALCULATE FRAMEWISE DISPLACEMENT FROM THE FILTERED MOTION ESTIMATES FOR EACH FRAME — 3210

RETURN AND REPEAT WITH ANY ADDITIONAL FRAME FROM A RUN — 3212

FIG. 32

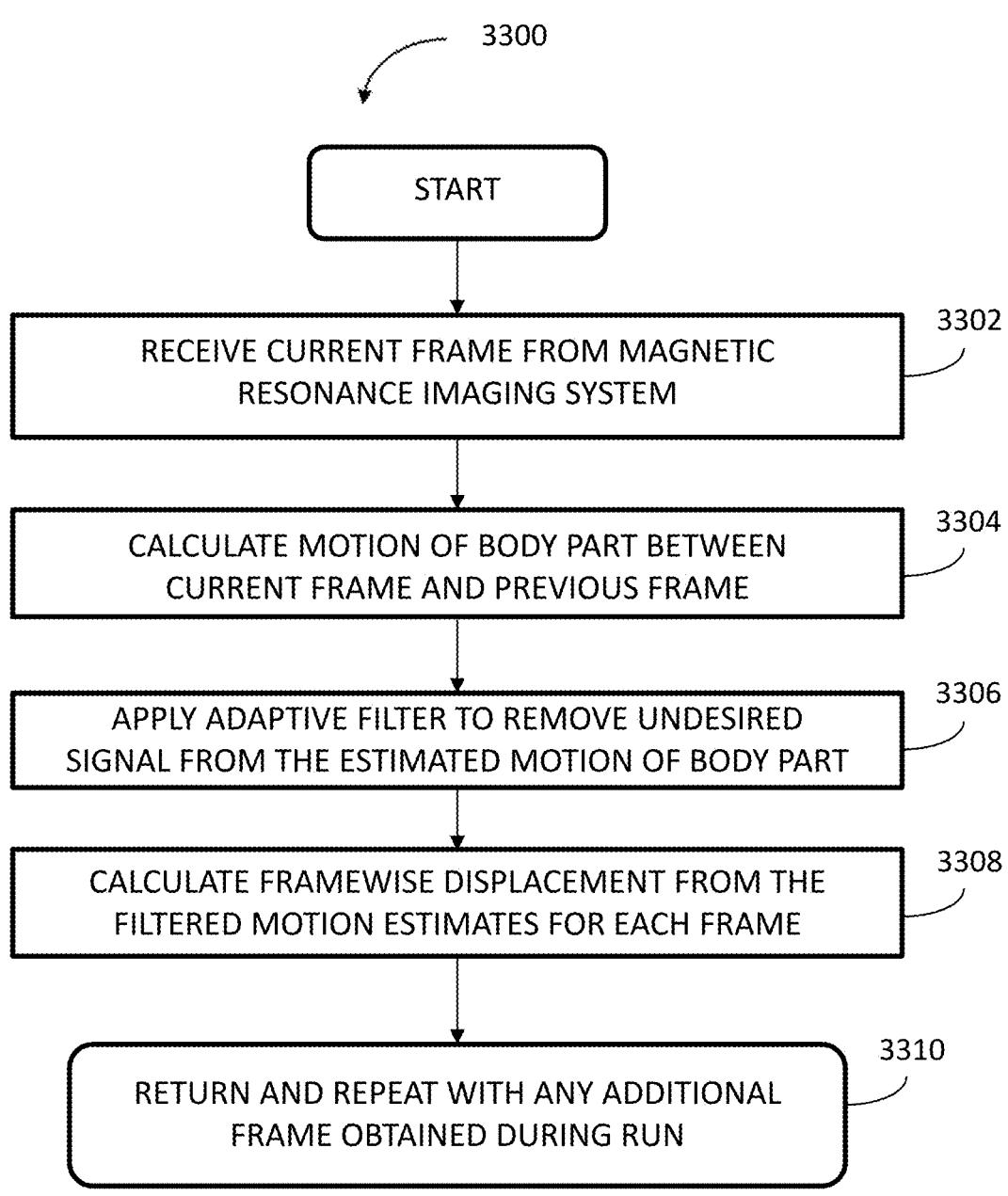

3300

START

RECEIVE CURRENT FRAME FROM MAGNETIC
RESONANCE IMAGING SYSTEM
3302

CALCULATE MOTION OF BODY PART BETWEEN
CURRENT FRAME AND PREVIOUS FRAME
3304

APPLY ADAPTIVE FILTER TO REMOVE UNDESIRED
SIGNAL FROM THE ESTIMATED MOTION OF BODY PART
3306

CALCULATE FRAMEWISE DISPLACEMENT FROM THE
FILTERED MOTION ESTIMATES FOR EACH FRAME
3308

RETURN AND REPEAT WITH ANY ADDITIONAL
FRAME OBTAINED DURING RUN
3310

FIG. 33

REAL TIME MONITORING AND PREDICTION OF MOTION IN MRI

CROSS-REFERENCE TO RELATED APPLICATION

This application is a continuation of U.S. application Ser. No. 18/061,254, filed Dec. 2, 2022, which is a continuation of U.S. application Ser. No. 17/451,539, filed Oct. 20, 2021, which is a continuation of U.S. application Ser. No. 16/491, 413, filed Sep. 5, 2019, which is a U.S. National Phase application of PCT/US2018/021608, filed Mar. 8, 2018, which claims priority to U.S. Provisional Application Ser. No. 62/468,858, filed Mar. 8, 2017, entitled REAL TIME MONITORING AND PREDICTION OF MOTION IN MRI, the entire disclosures of all of which are hereby incorporated herein by reference in their entireties.

ACKNOWLEDGEMENT OF GOVERNMENT SUPPORT

This invention was made with government support under NS088590, MH096773, HD087011, MH115357, DA041123, and DA041148 awarded by the National Institutes of Health. The government has certain rights in the invention.

FIELD

The field of the disclosure involves Magnetic Resonance Imaging (MRI), and more specifically, methods for monitoring, predicting and providing feedback about patient motion in real-time during MRI.

BACKGROUND

Body motion, such as head motion, represents the greatest obstacle to collecting quality brain Magnetic Resonance Imagining (MRI) data in humans. Head motion distorts both structural (T1-weighted, T2-weighted, etc.) and functional MRI data (task-driven [fMRI] and resting state functional connectivity [rs-fcMRI]). Even sub-millimeter head movements (e.g., micro-movements) may systematically alter structural and functional MRI data in some cases. Hence, much effort has been devoted towards developing post-acquisition methods for the removal of head motion distortions from MRI data.

Head movement from one MRI data frame to the next, rather than absolute movement away from the reference frame, is thought to induce the most significant MRI signal distortions. Motion-related distortions are strongly correlated with measures of framewise displacement (FD), which represent the sum of the absolute head movements in all six rigid body directions from frame to frame, as well as DVARS, the RMS of the derivatives of the differentiated timecourses of every voxel of an MRI image. Thus, measures such as FD and DVARS that capture the global effects of movement of the subject during MRI data acquisition, have been used to assess data quality in various post-hoc methods. For example, post-hoc frame censoring which removes all MRI data frames with FD values above a certain threshold (for example, excluding data frames with FD values >0.2 mm) has become a commonly used method for improving functional MRI data quality.

Though necessary for reducing artifacts, frame censoring comes at a steep price. For example, frame censoring can exclude 50% or more of rs-fcMRI data collected from a cohort depending on one's specific parameters and the quality of the underlying data. Because the accuracy of MRI measures improves as the number of frames increases, a minimum number of data frames may be required to obtain reliable data. If the number of frames remaining after censoring is too small, investigators may lose all data from a participant. In order to avoid this loss, investigators typically collect additional "buffer" data, an expensive practice that, by itself, does not guarantee sufficient high-quality MRI data for a given participant. The 'overscanning' required to remove motion-distorted data while maintaining sample sizes adequate to achieve a desired data quality has drastically increased the cost and duration of brain MRIs.

Recently developed structural MRI sequences with prospective motion correction use a similar approach to reduce the deleterious effects of head motion. These MRI sequences pair each structural data acquisition with a fast, low resolution, snap shot of the whole brain (echo-planar image=EPI), which is then used as a marker or navigator for head motion. These motion-correcting structural sequences calculate relative motion between successive navigator images and use this information to mark the linked structural data frames for exclusion and reacquisition. In this manner, structural data frames are 'censored,' thereby increasing the duration and cost of structural MRIs.

For both structural and functional MRI, access to real-time information about in-scanner head movement while scanning could greatly reduce the costs of MRI by eliminating the need for overscanning. The assessment of head movement obtained from real-time motion monitoring would allow scanner operators to continue each scan until the desired number of low-movement data frames have been acquired without need for excess buffer scans.

Existing approaches to real-time motion monitoring measure proxies for FD using expensive cameras and lasers. Unfortunately, such proxies of head movement are poorly correlated with FD because these proxies typically cannot distinguish movements of the face and scalp from brain movement. Therefore a need exists for additional methods and systems to account for motion distortions in MRI.

BRIEF DESCRIPTION OF THE DISCLOSURE

In one aspect, a computer-implemented method for monitoring movement of a patient undergoing a magnetic resonance imaging (MRI) scan by aligning MRI data is provided. The method is implemented on a computing device including at least one processor in communication with at least one memory device and the computing device is in communication with an MRI system. The method includes a) receiving, by the computing device, a data frame from the MRI system acquired during the MRI scan, b) aligning, by the computing device, the received data frame to a reference image, c) calculating, by the computing device, motion of at least a portion of the patient between the received data frame and the reference image, d) providing stimulus to the patient, by the computing device, wherein the stimulus includes a task to be performed by the patient during the MRI scan and sensor feedback indicating the motion of the at least a portion of the patient, and e) repeating steps a) through d) during the MRI scan to make the stimulus interactive with the patient to perform the task while controlling the motion of the patient.

In another aspect, a system includes a computing device including a memory device and a processor. The memory device stores instructions that configure the computing device to receive a data frame from a magnetic resonance imaging (MRI) system performing an MRI scan of a patient, compare the data frame to a reference image to assess motion of a body part of the patient during the MRI scan, generate sensory feedback to be communicated to the patient during the MRI scan based on the motion of the body part of the patient during the MRI scan; and adjust the sensory feedback during the MRI scan as the motion of the body part of the patient changes. The system also includes a feedback device configured to provide stimulus to the patient during the MRI scan, wherein the stimulus includes a task as part of at least one of a game, a movie, a cartoon, a shape, or an auditory signal.

Another aspect is a computer-implemented method for monitoring movement of a patient undergoing a magnetic resonance imaging (MRI) scan by aligning MRI data. The method is implemented on a computing device including at least one processor in communication with at least one memory device. The computing device is in communication with an MRI system. The method includes receiving a data frame from the MRI system performing the MRI scan of the patient, comparing the data frame to a reference image to assess motion of a body part of the patient during the MRI scan, generating stimulus to be communicated to the patient during the MRI scan based on a task of the MRI scan and the motion of the body part of the patient during the MRI scan, adjusting the stimulus during the MRI scan to adjust the task and as the motion of the body part of the patient changes, and communicating the stimulus to the patient during the MRI scan, wherein the sensory feedback includes at least one of a game, a movie, a cartoon, a shape, or an auditory signal.

BRIEF DESCRIPTION OF THE DRAWINGS

Aspects will be readily understood by the following detailed description in conjunction with the accompanying drawings. Aspects are illustrated by way of example and not by way of limitation in the figures of the accompanying drawings.

4

Figure 2A:
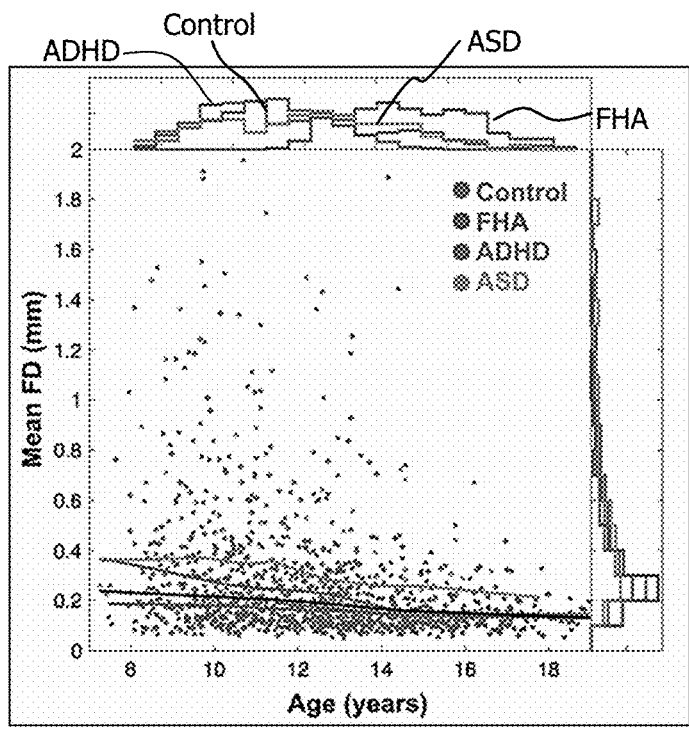
FIG. 2A is a graph summarizing the mean FD values as a function of the patient's age; each point is shaded according to each patient's diagnosis (Controls, Family History of Alcoholism [FHA], Attention Deficit Hyperactivity Disorder [ADHD] and Autism Spectrum Disorder (ASD)).
Figure 5A:
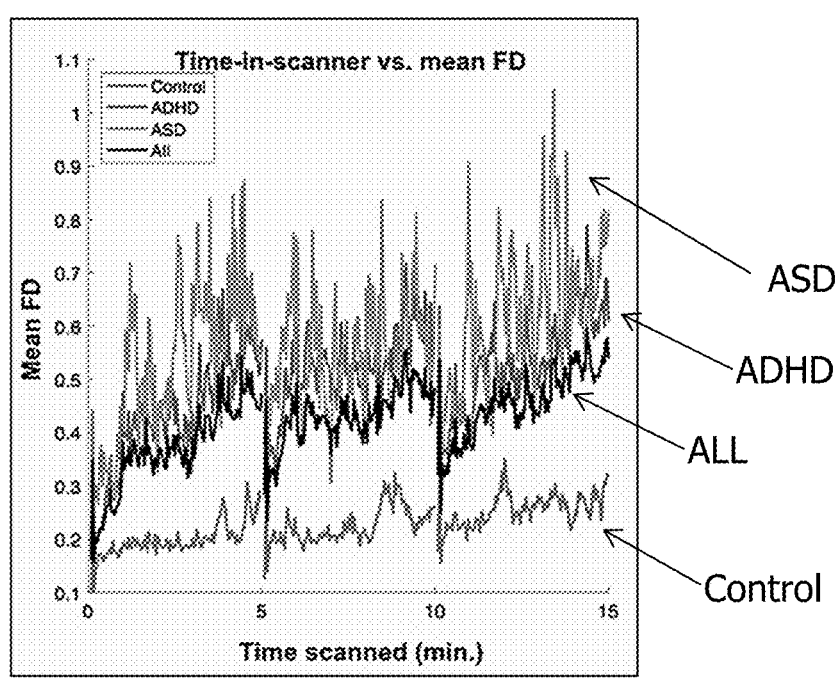

FIG. 5A shows the mean FD for each cohort illustrated in FIG. 2A and the sample as a whole (block) as a function of the time participants have already spent in the scanner.

Figure 5B:
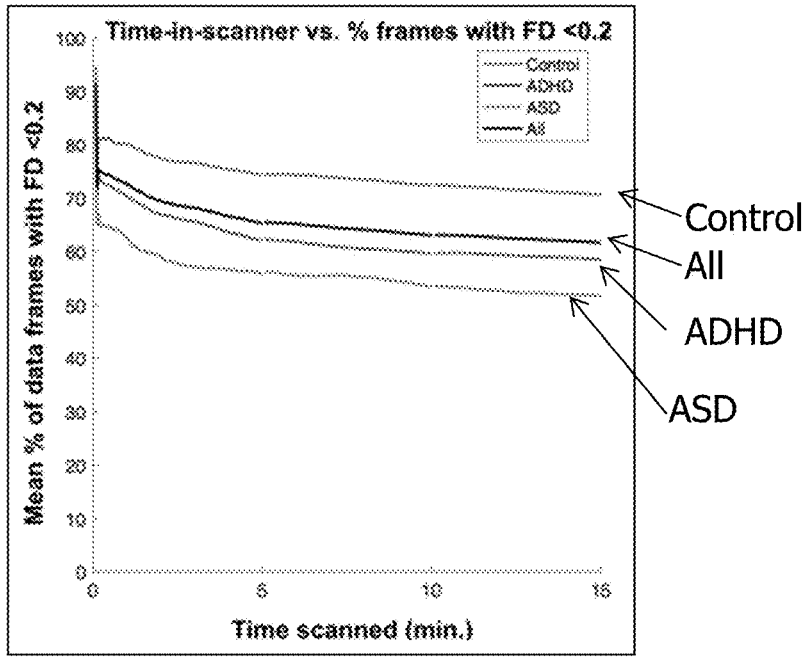

FIG. 5B shows the percentage of data frames that were FD<0.2 at every time-point in the scan for each of the cohorts illustrated in FIG. 2A.

Figure 5C:
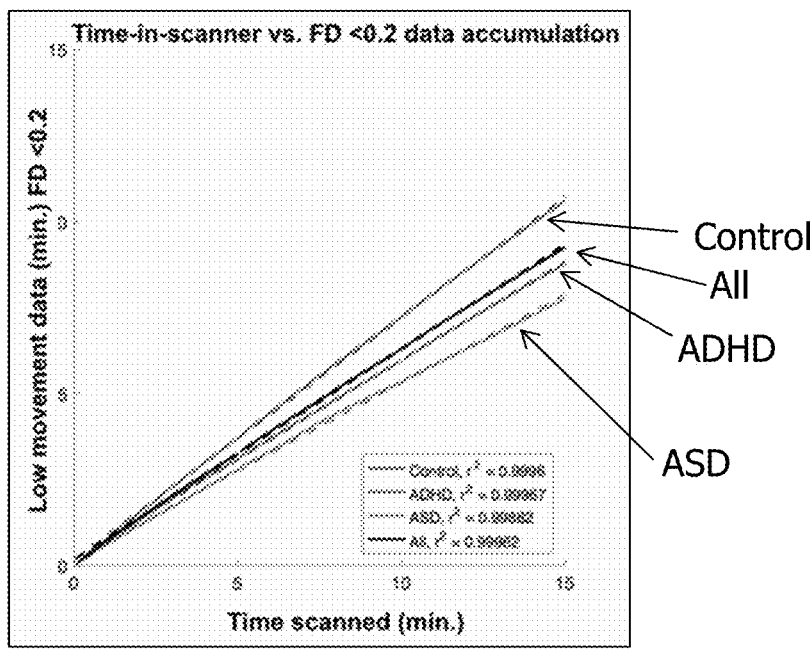

FIG. 5C shows the relationship between the time scanned (x-axis) and the mean amount of low movement data (FD<0.2) accumulated for each cohort.

Figure 5D:
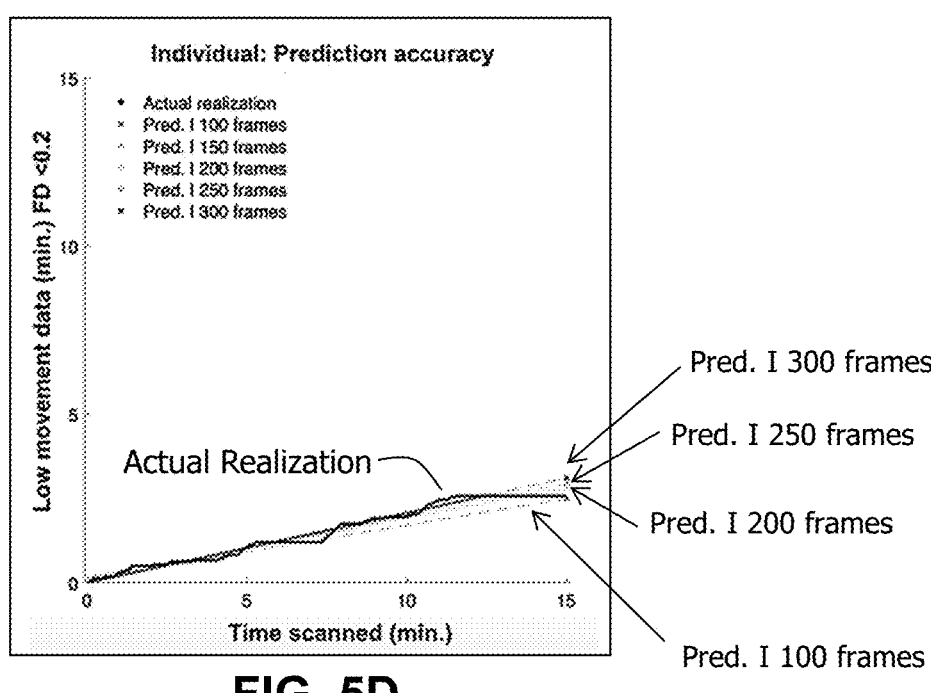

FIG. 5D shows the FD trace for a single individual MRI participant (black line) compared FIRMM predictions made at different points during the experiment (shaded traces).

Figure 5E:
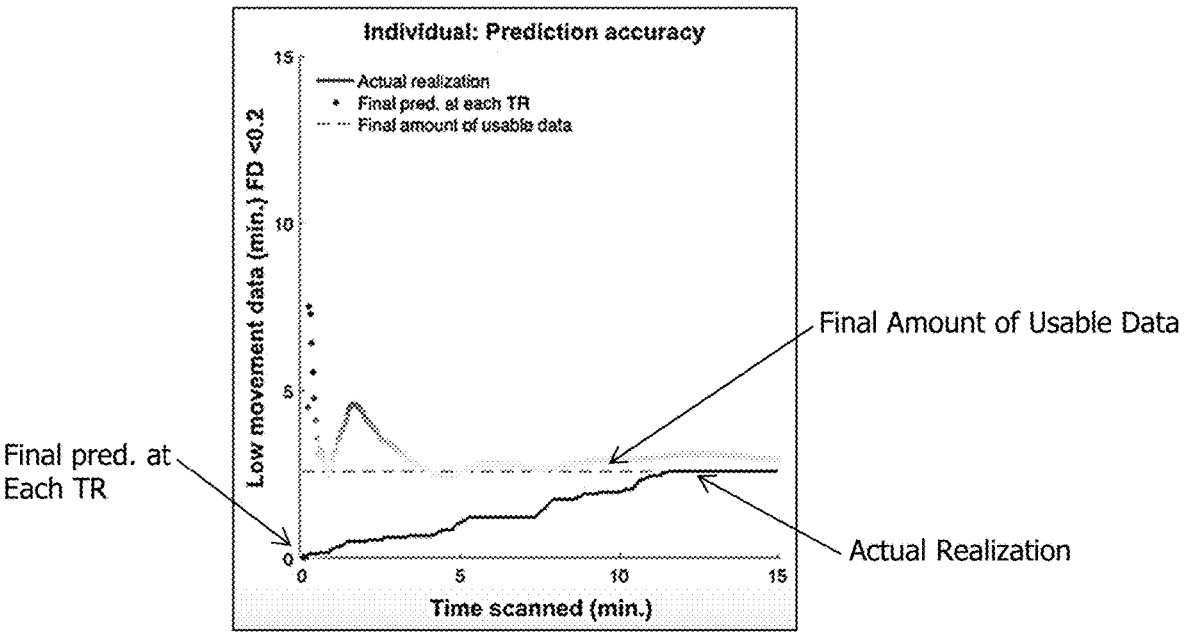
Figure 5F:
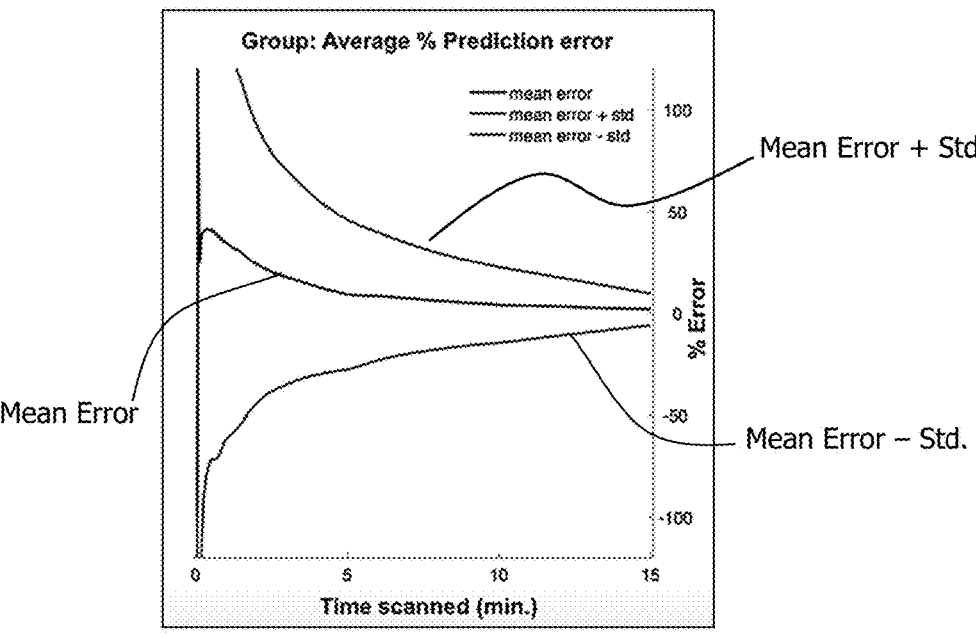

FIG. 5E shows FIRMM's prediction error (in percent; y-axis) across the length of the scan (x-axis) for the same subject as in FIG. 5F.

FIG. 5F shows FIRMM's average prediction error (%) over time (x-axis) for the entire group (black line).

Figure 6A:
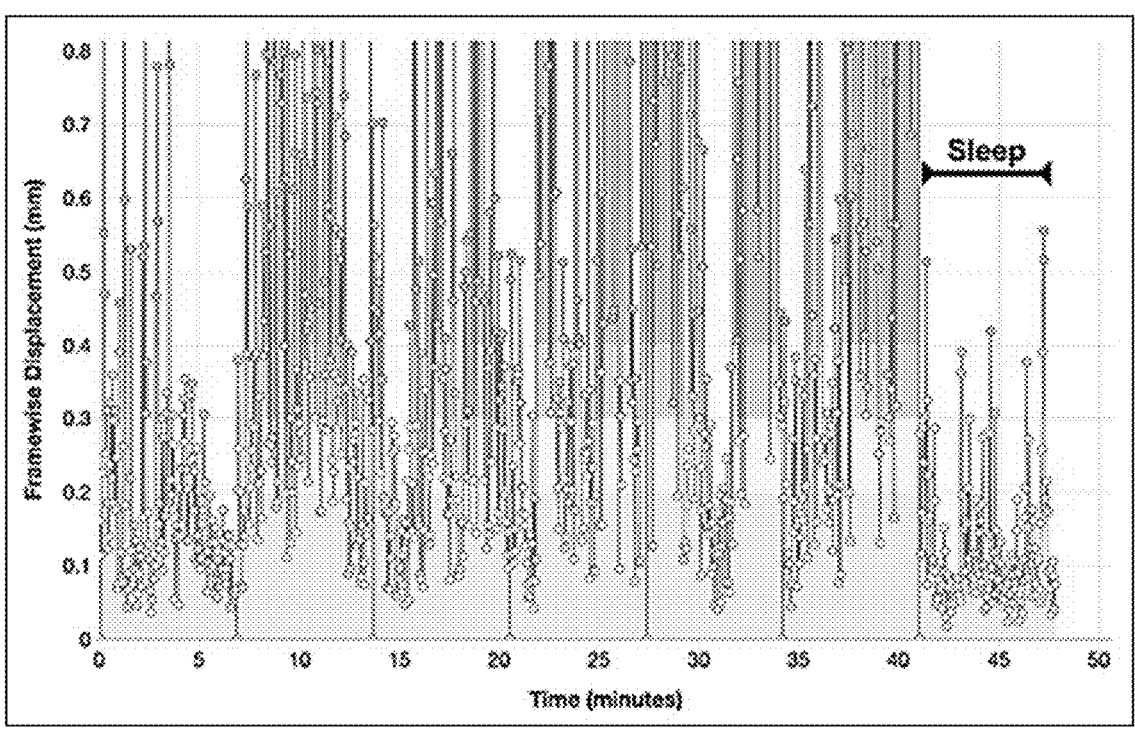

FIG. 6A shows the FIRMM trace for a child who fell asleep towards the end of the scanning session.

Figure 6B:
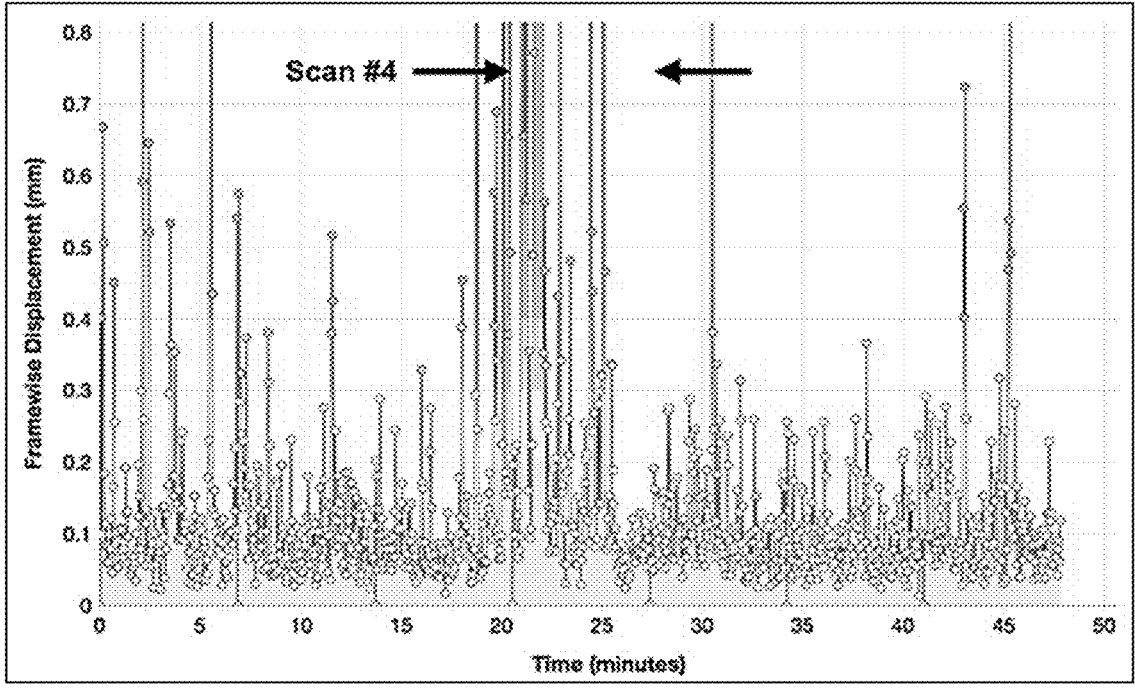

FIG. 6B shows the FIRMM trace for a child who had much greater head movement for scan #4.

Figure 7A:
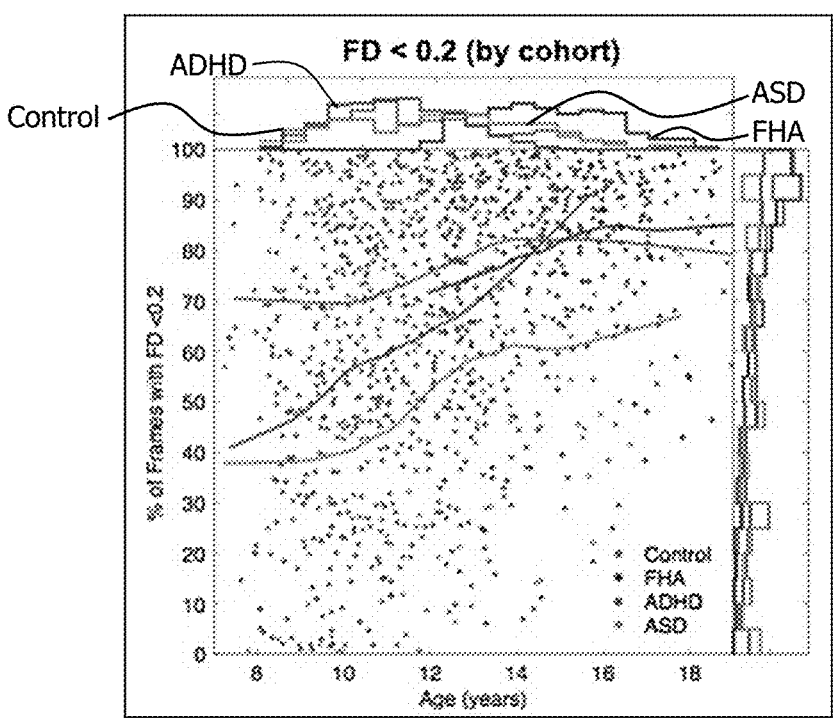

FIG. 7A shows the percentage of data frames below the criterion FD<0.2 for participants sorted by diagnoses (Controls, Family History of Alcoholism [FHA], Attention Deficit Hyperactivity Disorder [ADHD] and Autism Spectrum Disorder [ASD]).

Figure 7B:
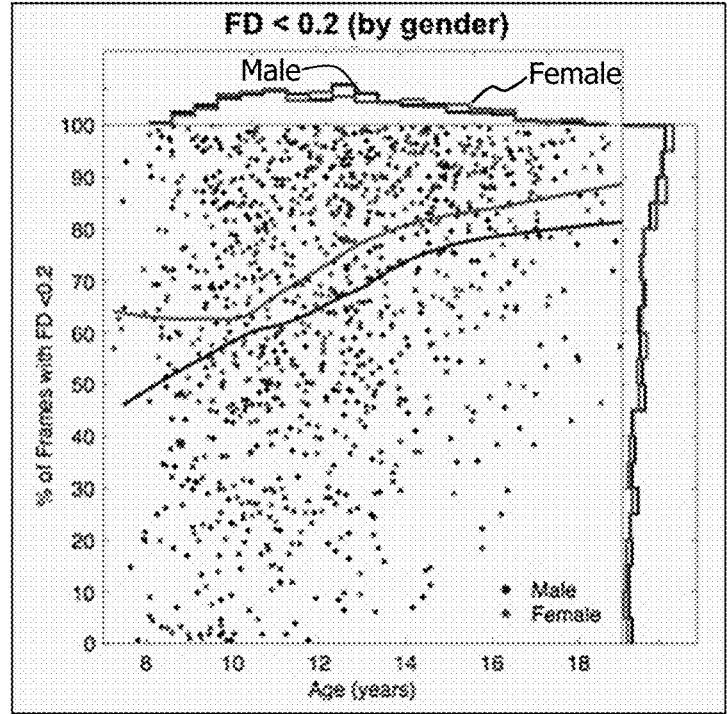

FIG. 7B shows the percentage of data frames below the criterion FD<0.2 for participants by gender.

Figure 7C:
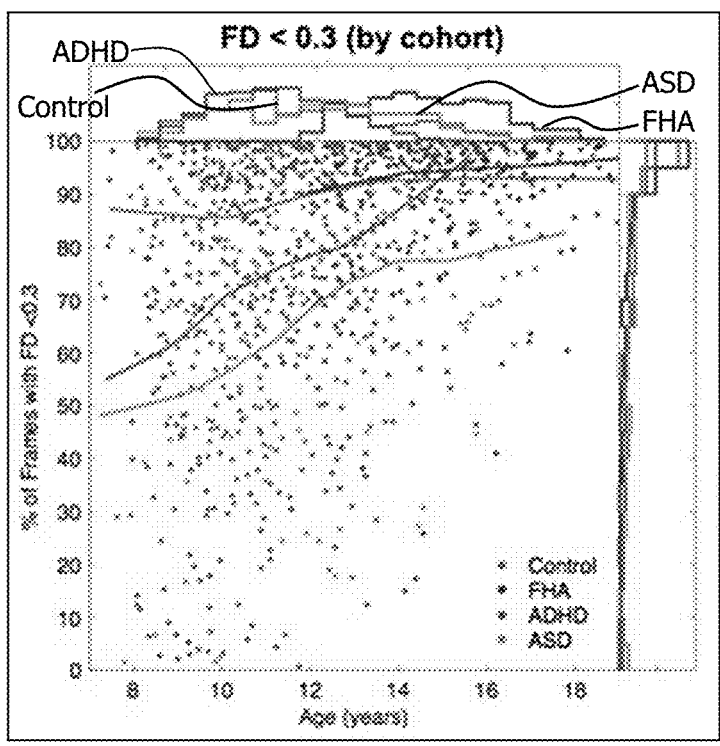

FIG. 7C shows the percentage of data frames below the criterion FD<0.3 for participants sorted by the cohorts of FIG. 7A.

Figure 7D:
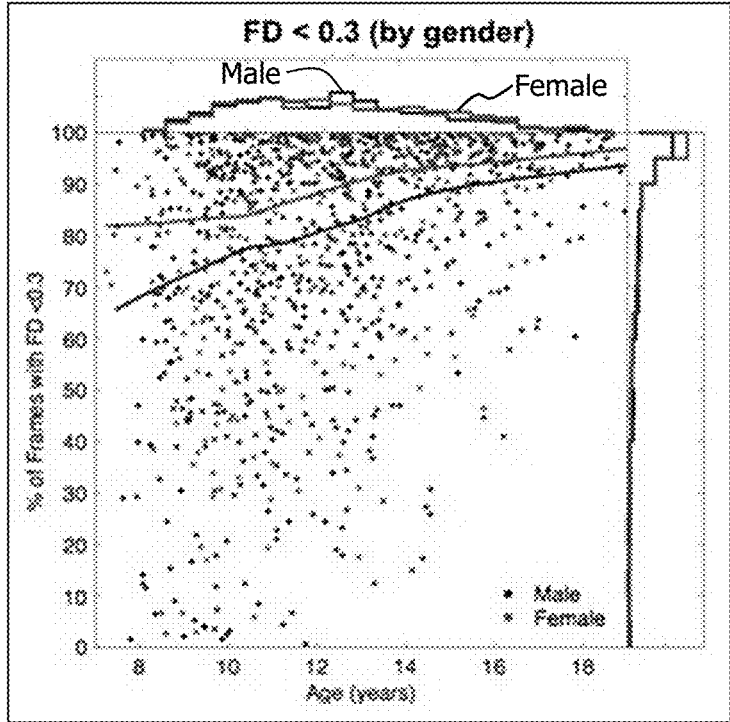

FIG. 7D shows the percentage of data frames below the criterion FD<0.3 for participants sorted by gender.

Figure 7E:
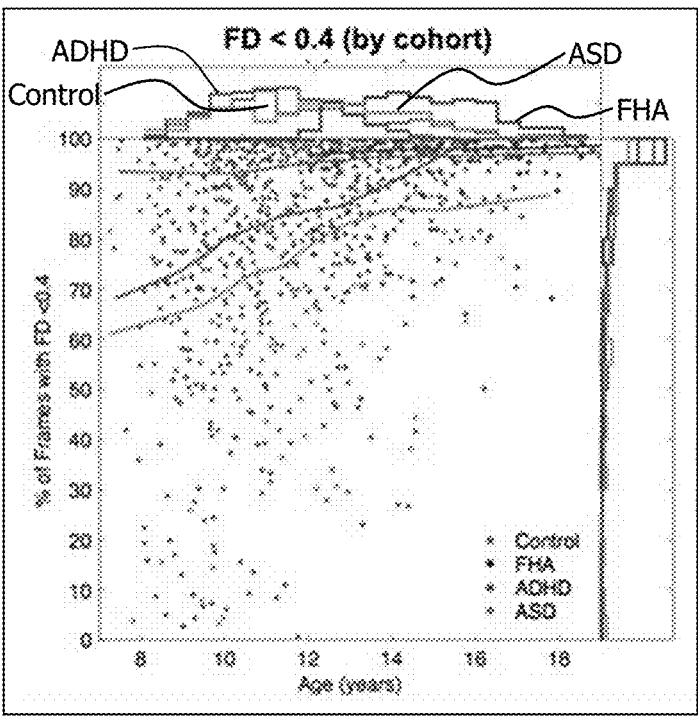

FIG. 7E shows the percentage of data frames below the criterion FD<0.4 for participants sorted by the cohorts of FIG. 7A.

Figure 7F:
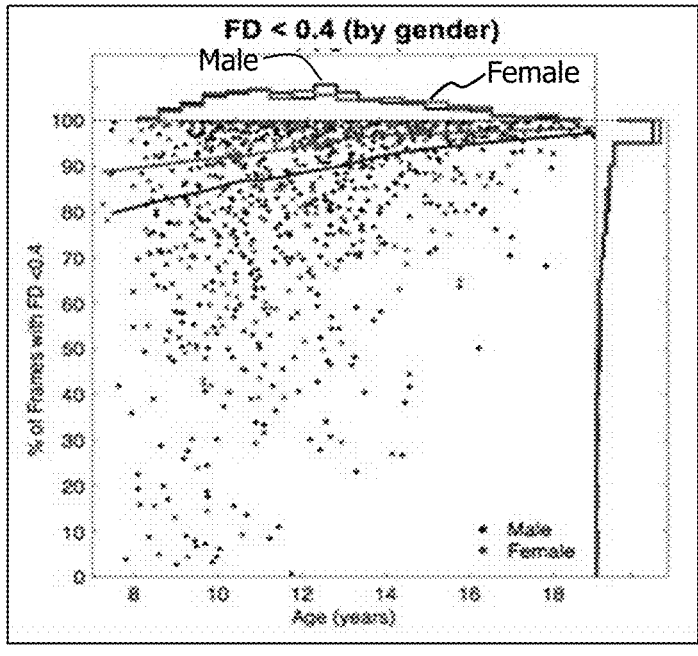

FIG. 7F shows the percentage of data frames below the criterion FD<0.4 for participants sorted by gender.

Figure 8:
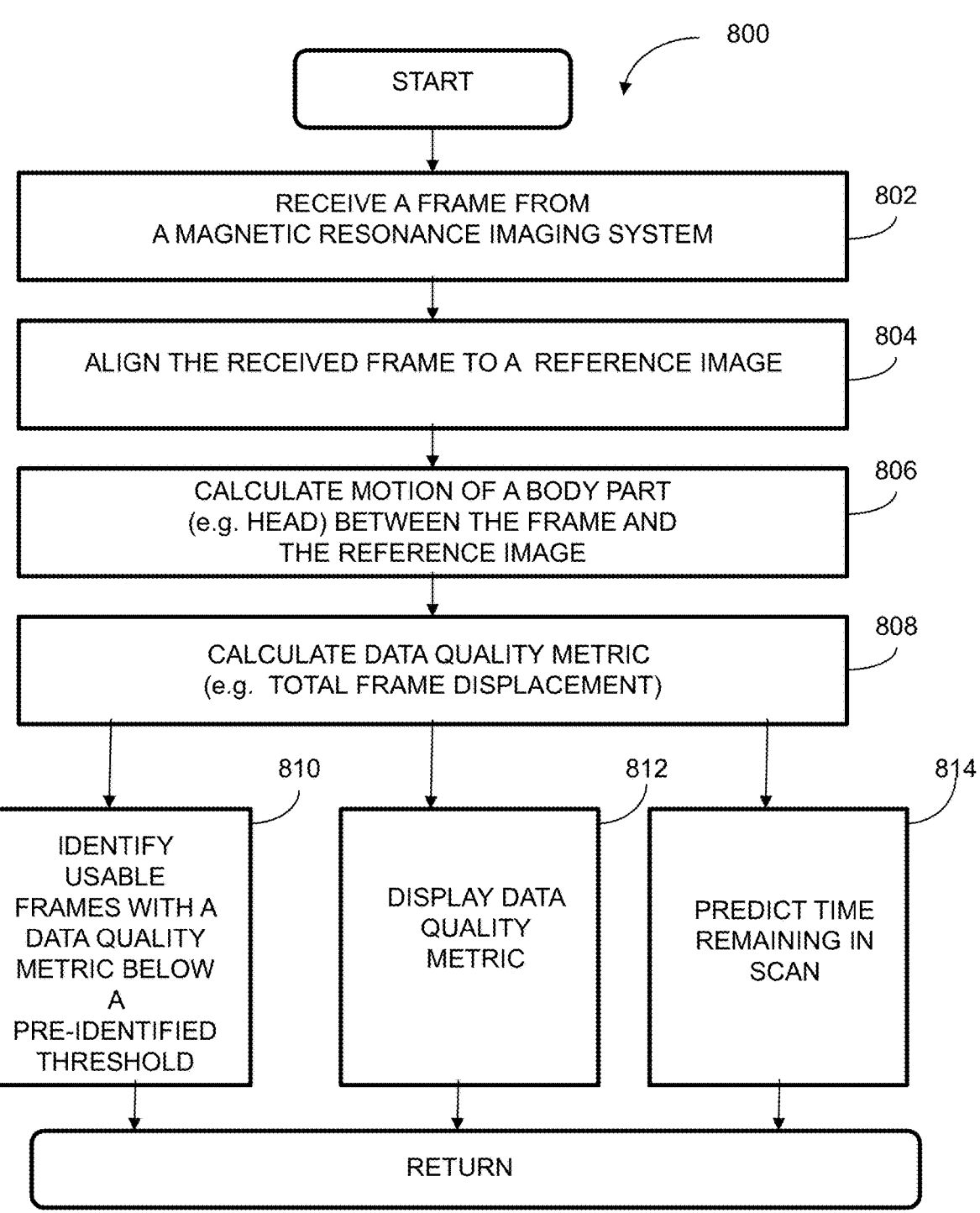

FIG. 8 is a flow chart illustrating the operations for aligning magnetic resonance imaging (MRI) data from a MRI scan to a selected frame in the MRI scan, in accordance with the disclosure.

Figure 9:
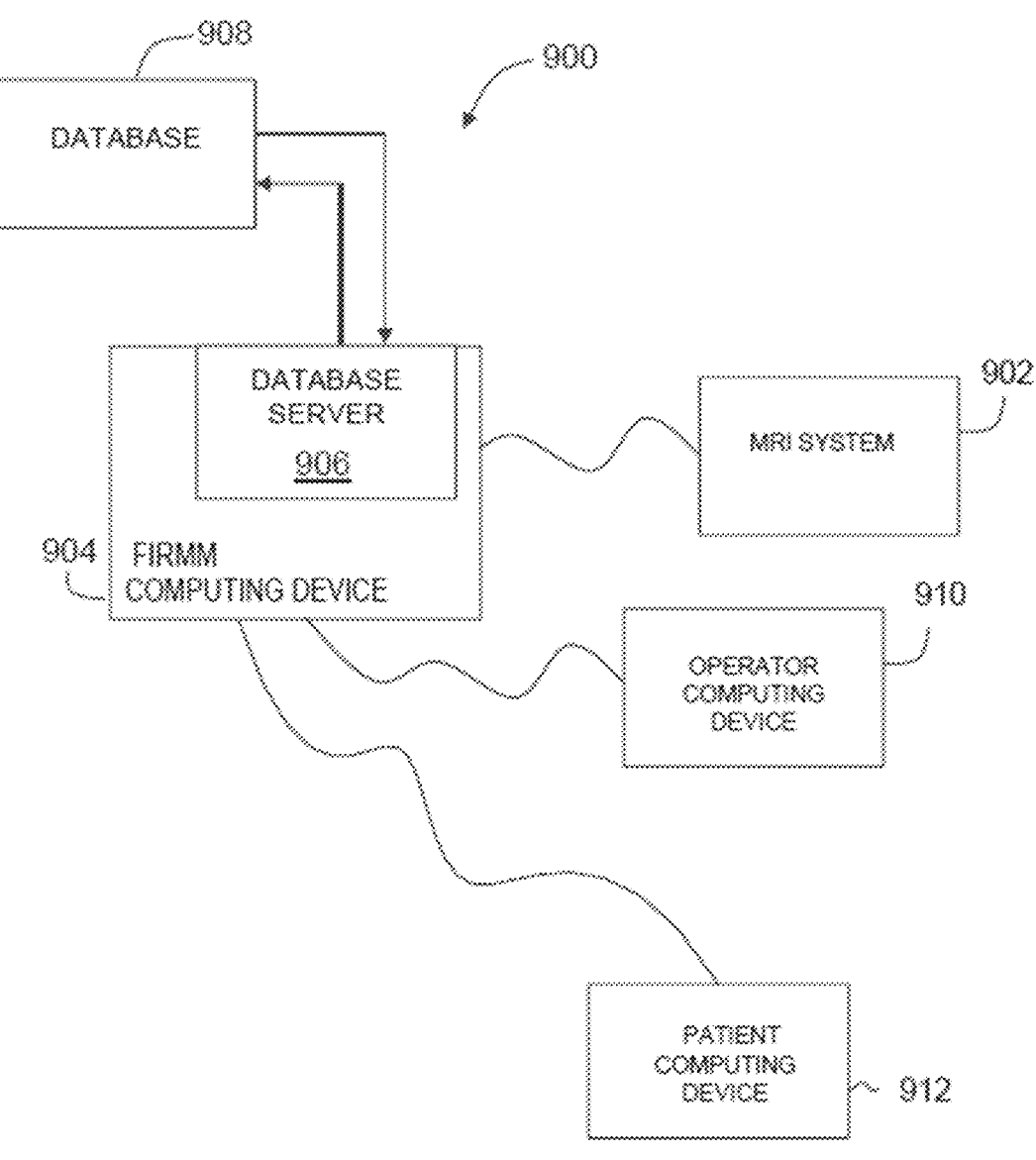

FIG. 9 is a block diagram schematically showing a system for real-time monitoring of patient motion while obtaining MRI images, in accordance with one aspect of the disclosure.

FIG. 10 is a block diagram schematically showing an example of a computing system, in accordance with one aspect of the disclosure.

Figure 11:
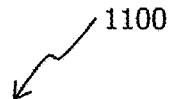

FIG. 11 shows a screen-shot image of a FIRMM (Framewise Integrated Real-time MRI Monitoring) graphical user interface (GUI), in accordance with one aspect of the disclosure.

Figure 12A:
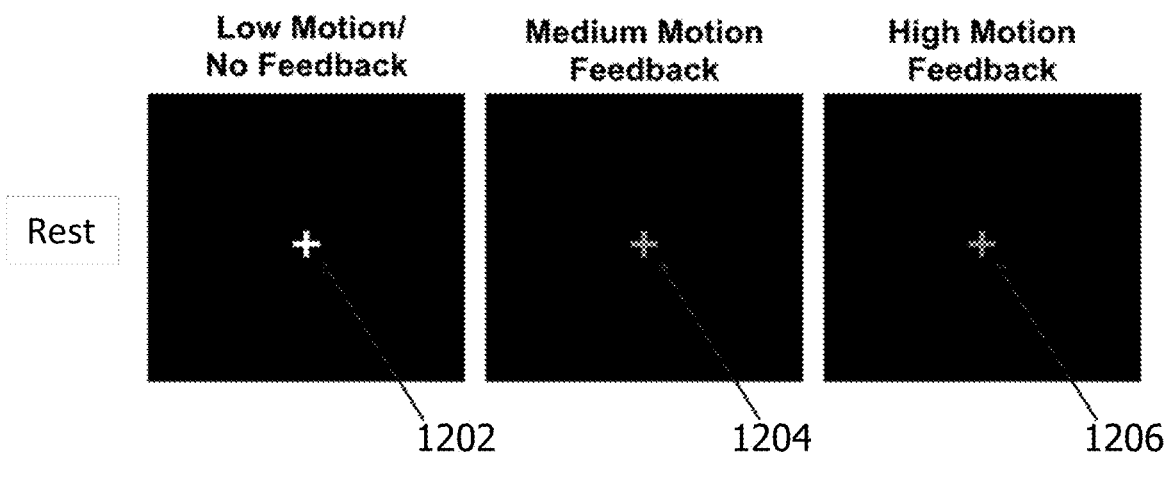

FIG. 12A shows a sample screen-shot of a real-time visual feedback display for a subject undergoing MRI scans for the rest condition including feedback for three levels of patient motion: low/no motion, medium motion, and high motion.

Figure 12B:
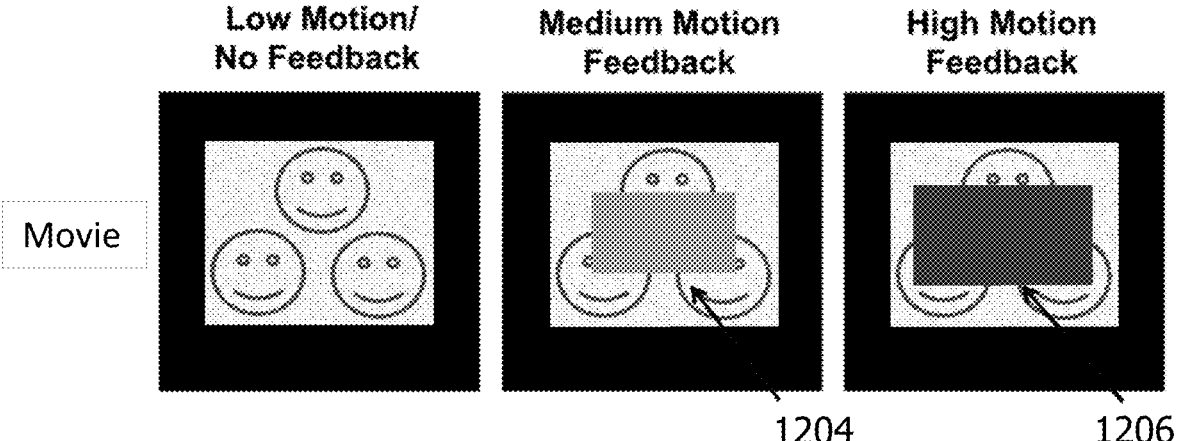

FIG. 12B shows a sample screen-shot of a real-time visual feedback display for a subject undergoing MRI scans for the movie condition including feedback for three levels of patient motion: low/no motion, medium motion, and high motion.

Figure 13A:
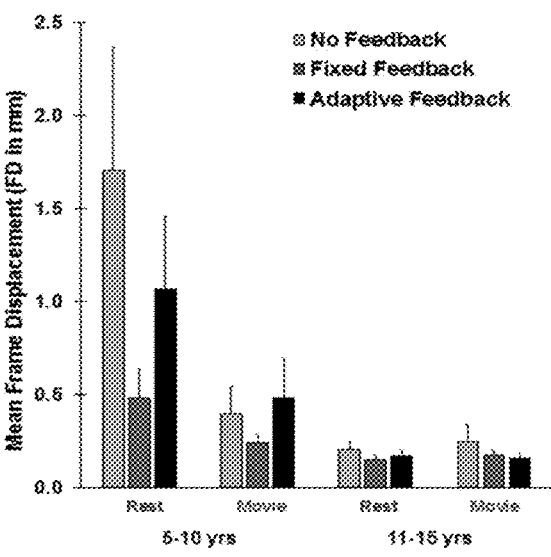

FIG. 13A shows the mean FD values for both rest and movie conditions for no feedback, fixed feedback, and adaptive feedback.

Figure 13B:
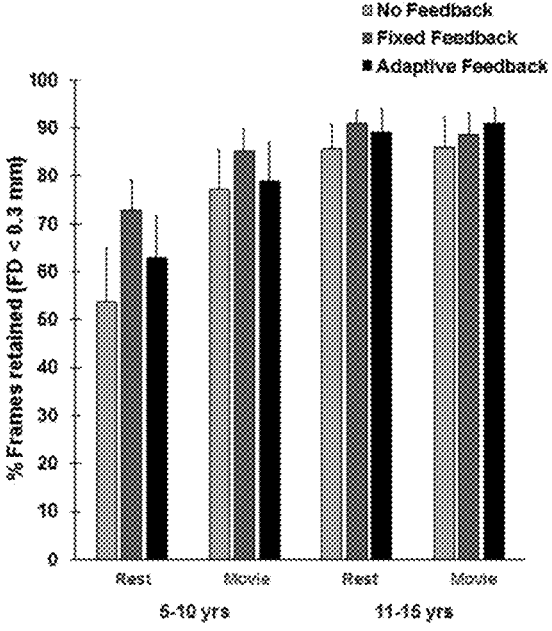

FIG. 13B shows the percentage of frames retained after volume censoring (FD<0.3 mm) for both rest and movie conditions for no feedback, fixed feedback, and adaptive feedback.

Figure 14A:
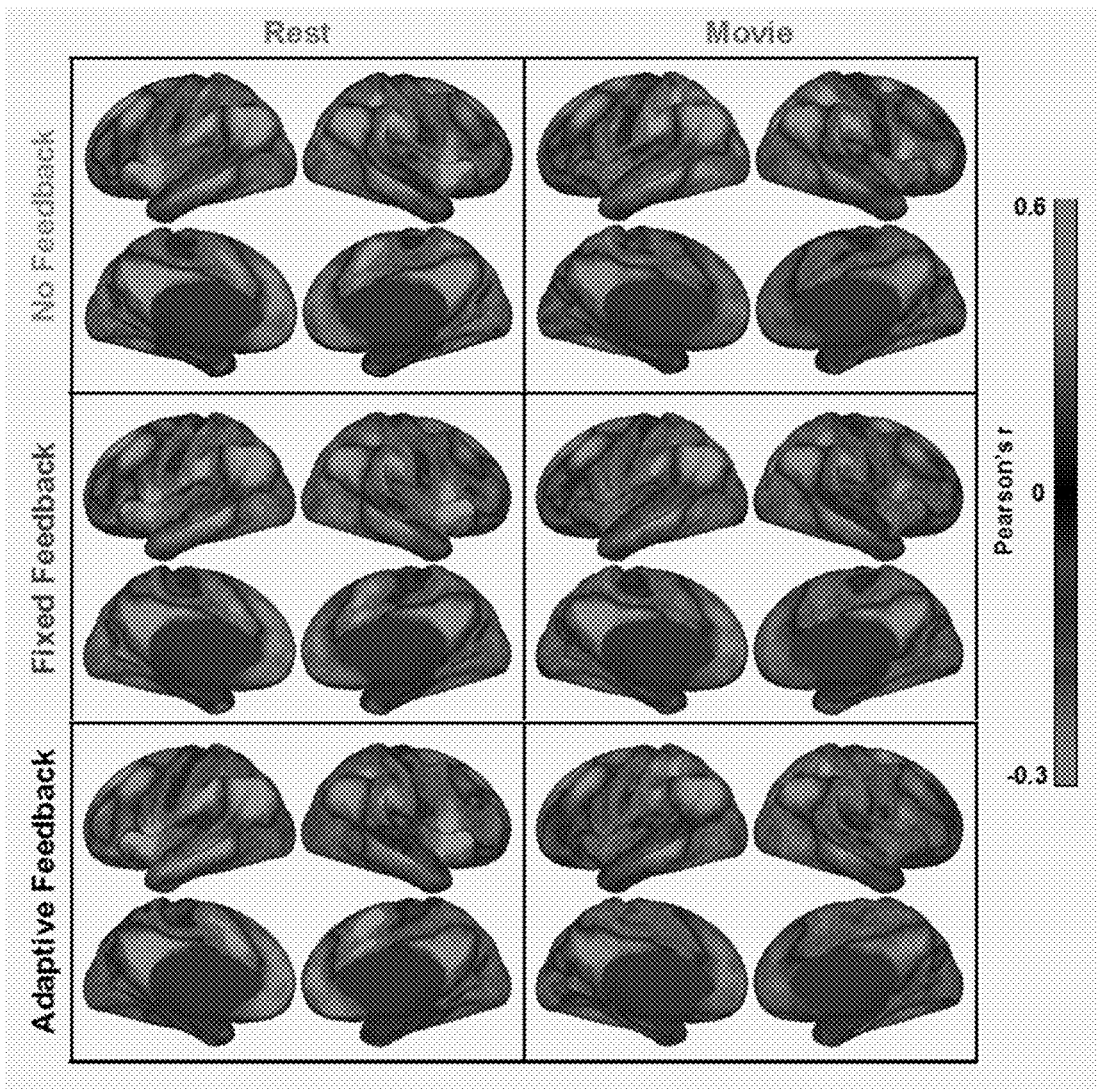

FIG. 14A shows seed maps for the left angular gyrus (Talairach coordinates −46, −63, 31) for 17 subjects with useable functional connectivity (FC) data in every condition.

Figure 14B:
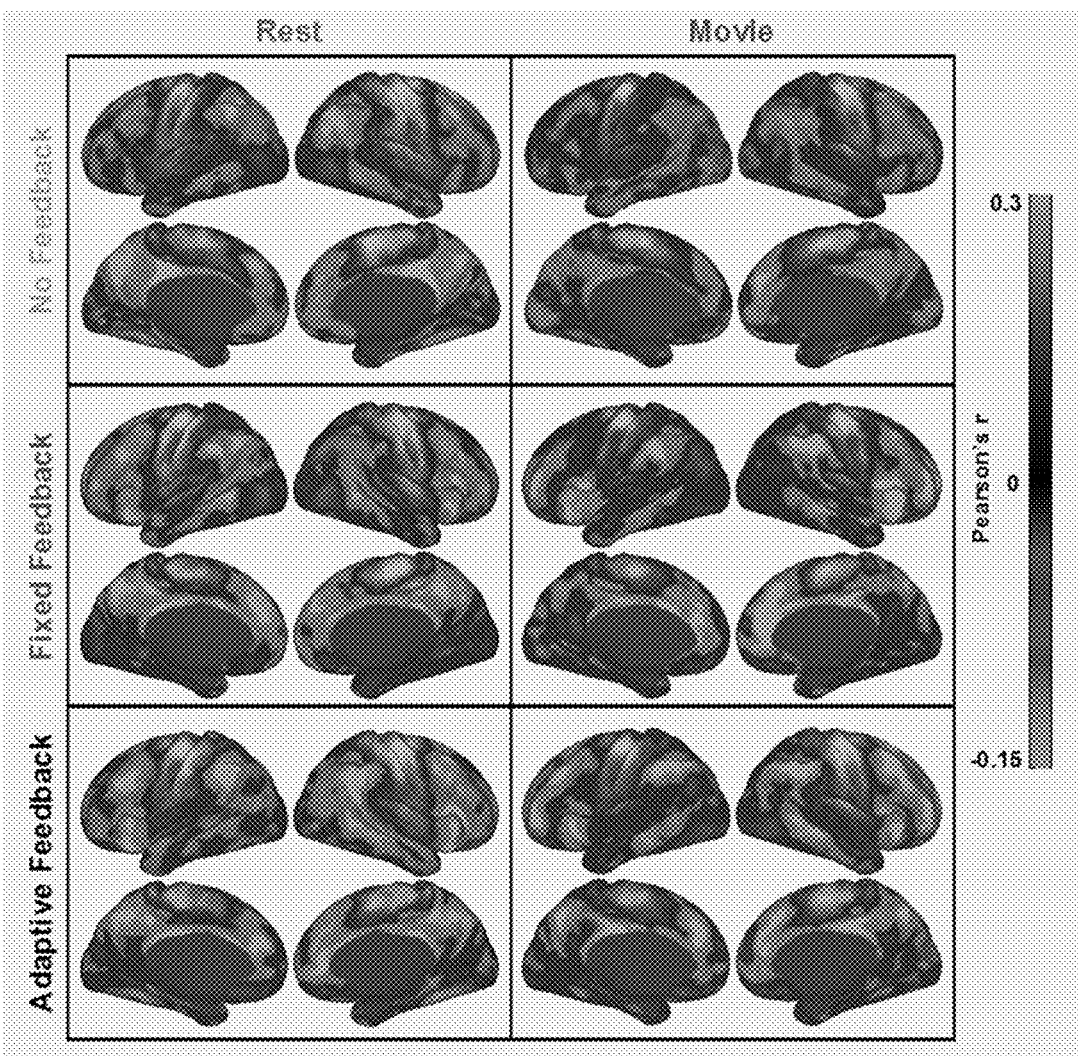

FIG. 14B shows seed maps for the right motor cortex (Talairach coordinates 39, −19, 56) for 17 subjects with useable functional connectivity (FC) data in every condition.

Figure 15A:
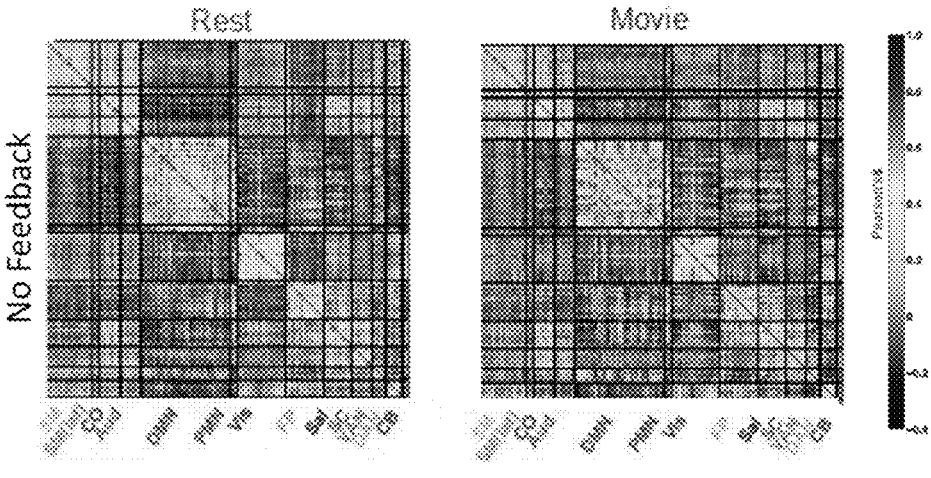

FIG. 15A shows correlation matrices that display FC between 264 previously defined regions of interest (ROI) organized by network for both rest and movie conditions with no feedback.

Figure 15B:
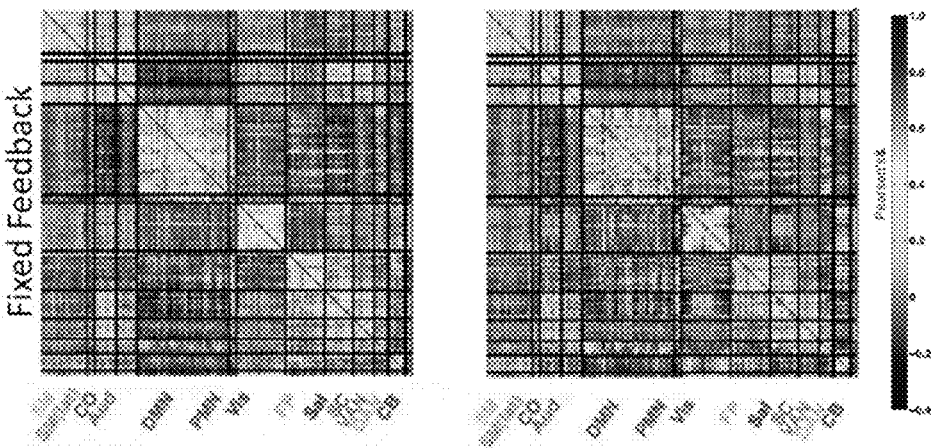

FIG. 15B shows correlation matrices that display FC between 264 previously defined ROI organized by network for both rest and movie conditions with fixed feedback.

Figure 15C:
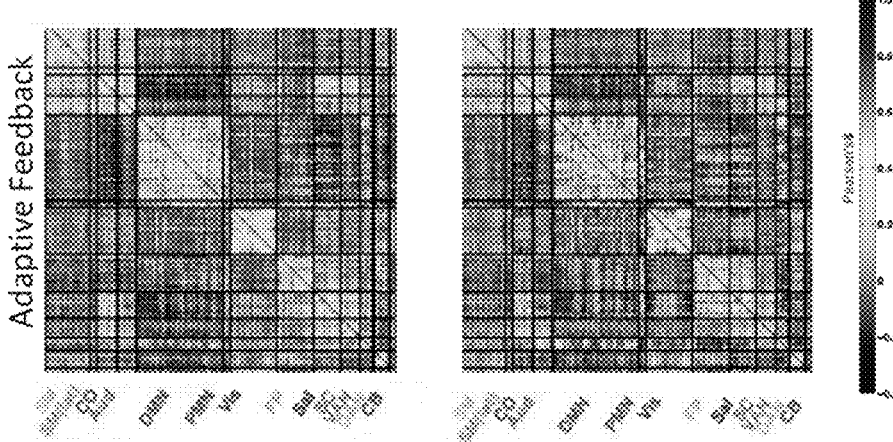

FIG. 15C shows correlation matrices that display FC between 264 previously defined ROI organized by network for both rest and movie conditions with adaptive feedback.

Figures 16A, 16B, 16C, 16D:
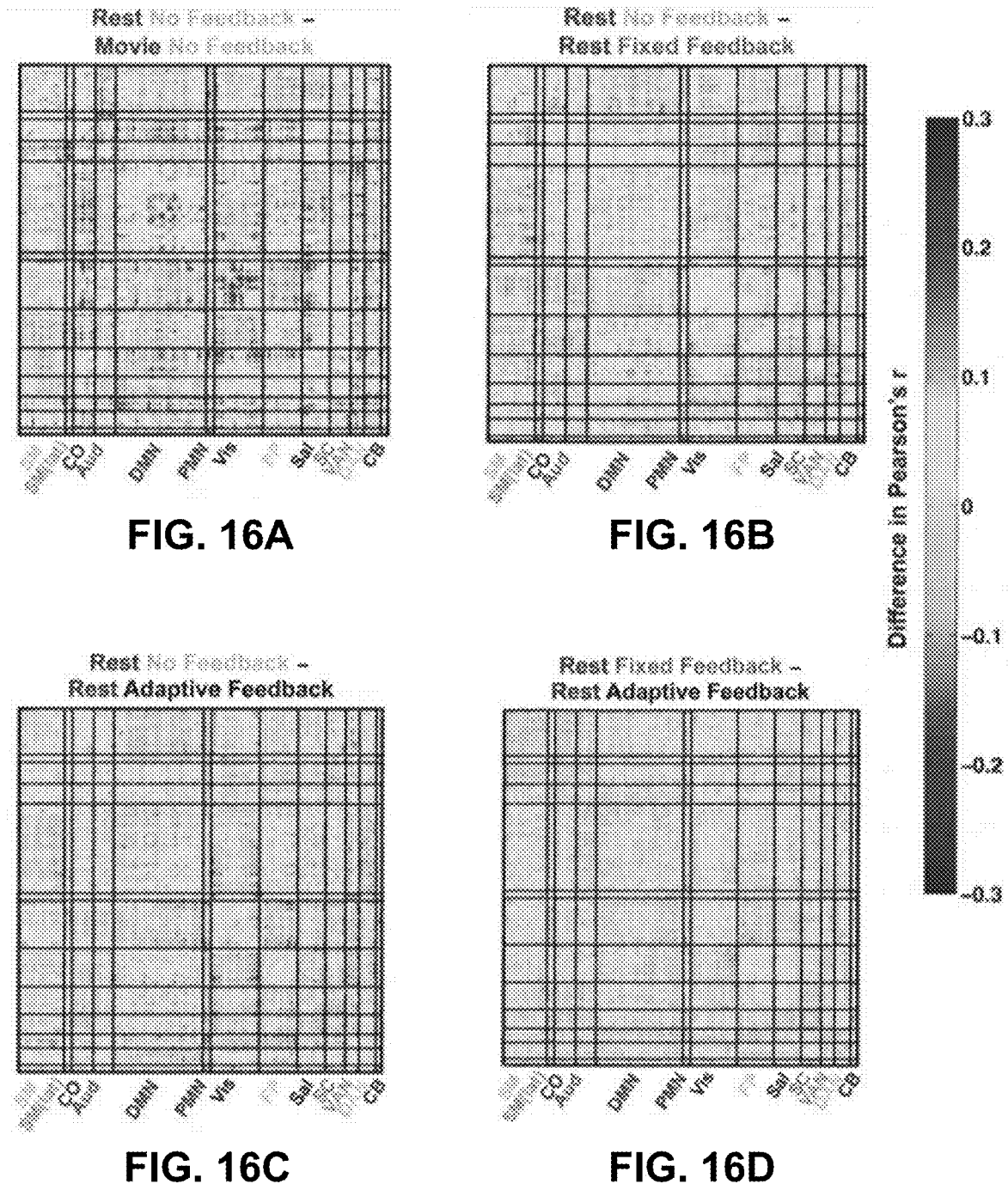

FIG. 16A shows differences in FC data between rest condition with no feedback and movie condition with no feedback.

FIG. 16B shows differences in FC data between rest condition with no feedback and rest condition with fixed feedback.

FIG. 16C shows differences in FC data between rest condition with no feedback and rest condition with adaptive feedback.

FIG. 16D shows differences in FC data between rest condition with fixed feedback and rest condition with adaptive feedback.

Figure 17:
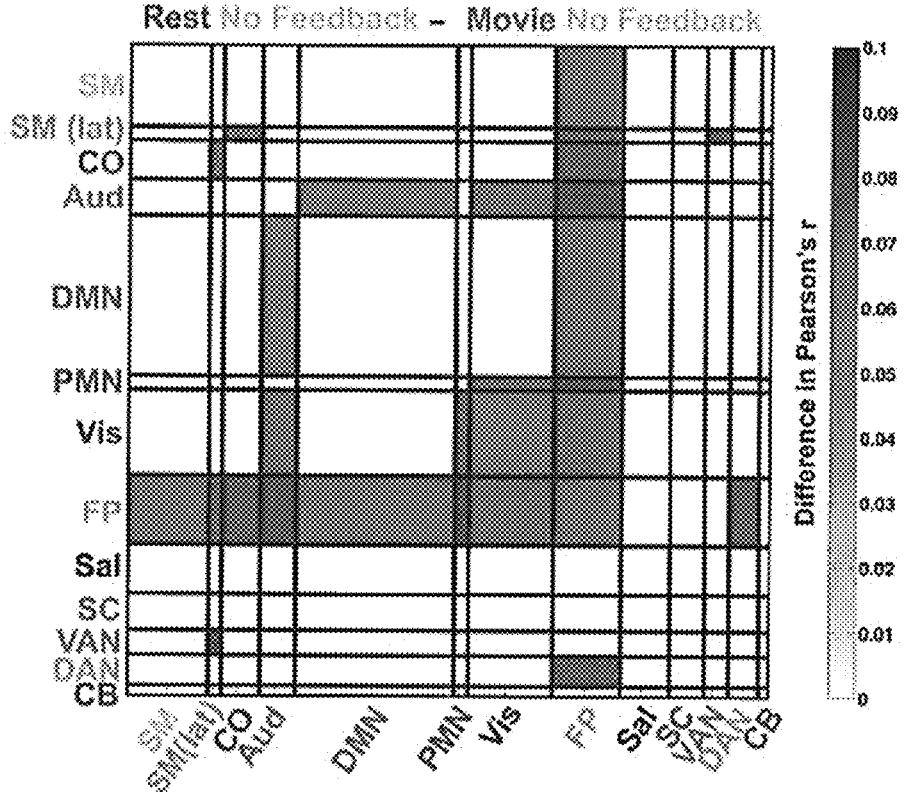

FIG. 17 shows significant network-level differences between rest condition with no feedback and movie condition with no feedback.

Figure 18A:
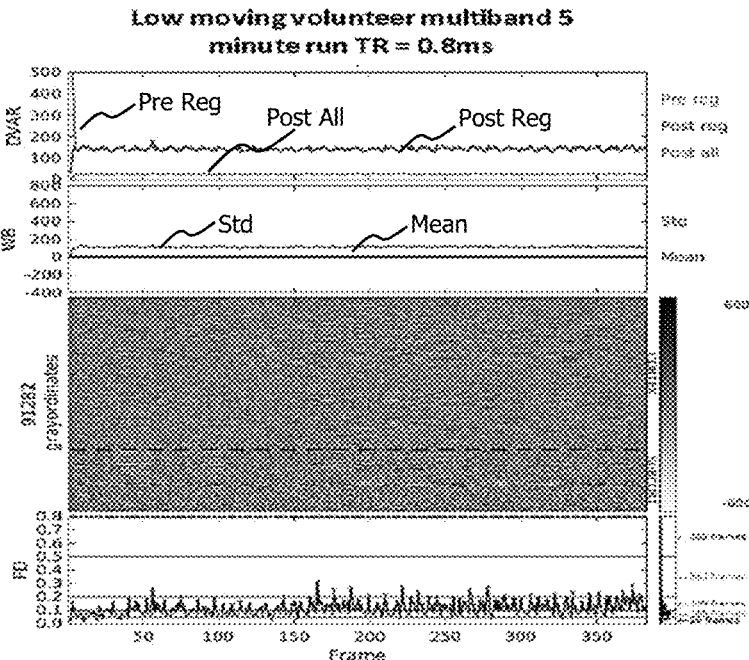

FIG. 18A shows BOLD visualization data (BVD) plots of a low moving subject using multiband imaging.

Figure 18B:
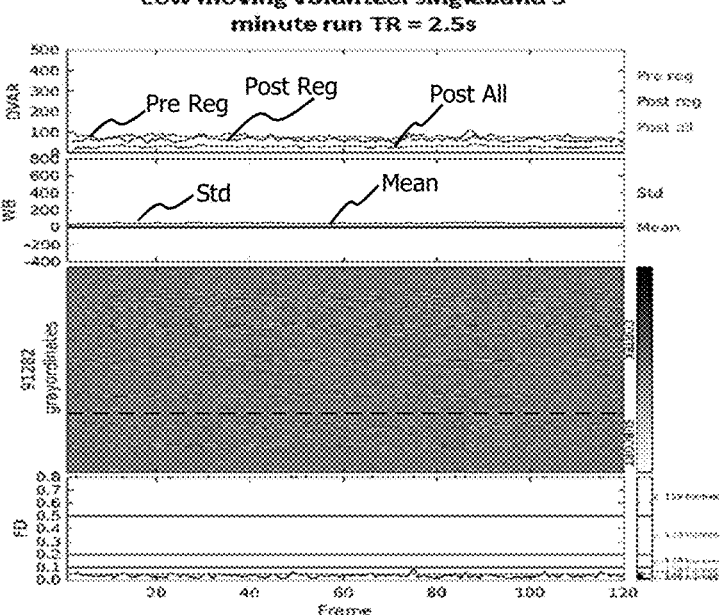

FIG. 18B shows BOLD visualization data (BVD) plots of a low moving subject using single-band imaging.

Figure 19A:
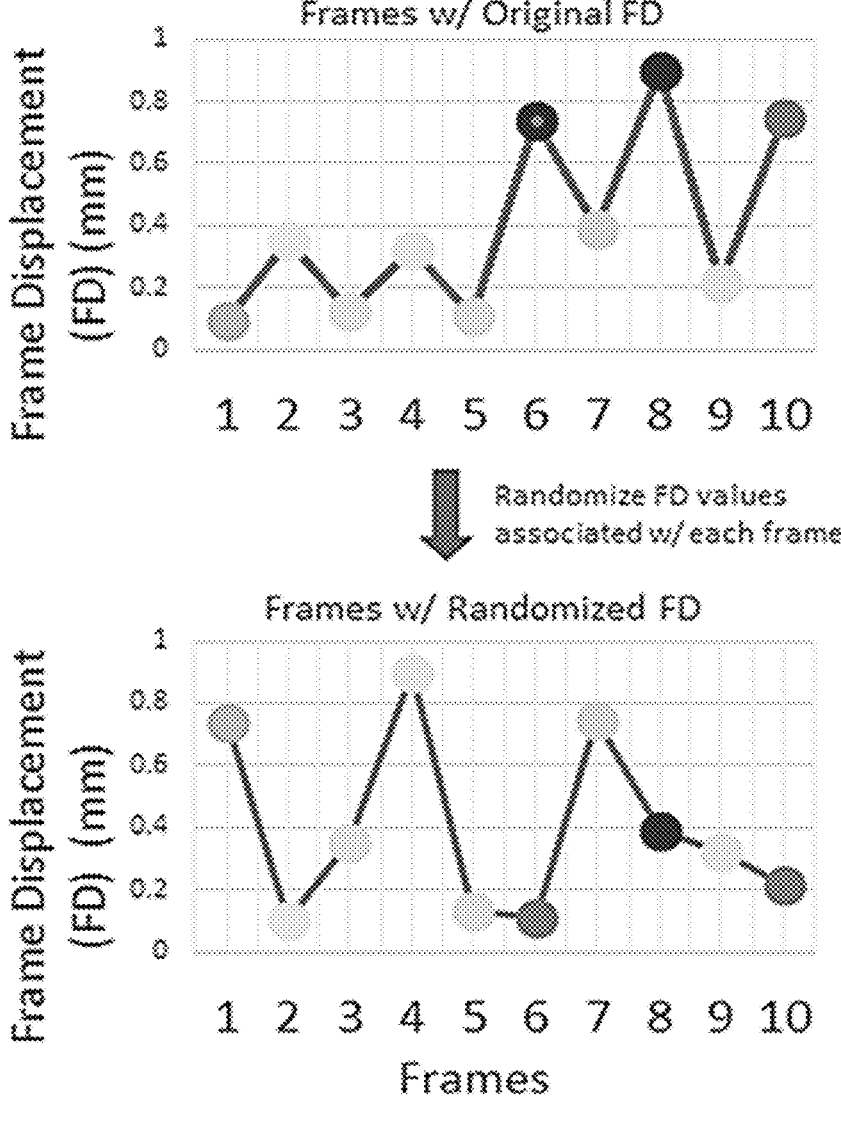

FIG. 19A illustrates a first step in conducting quantitative assessment using a quality measure described herein.

Figure 19B:
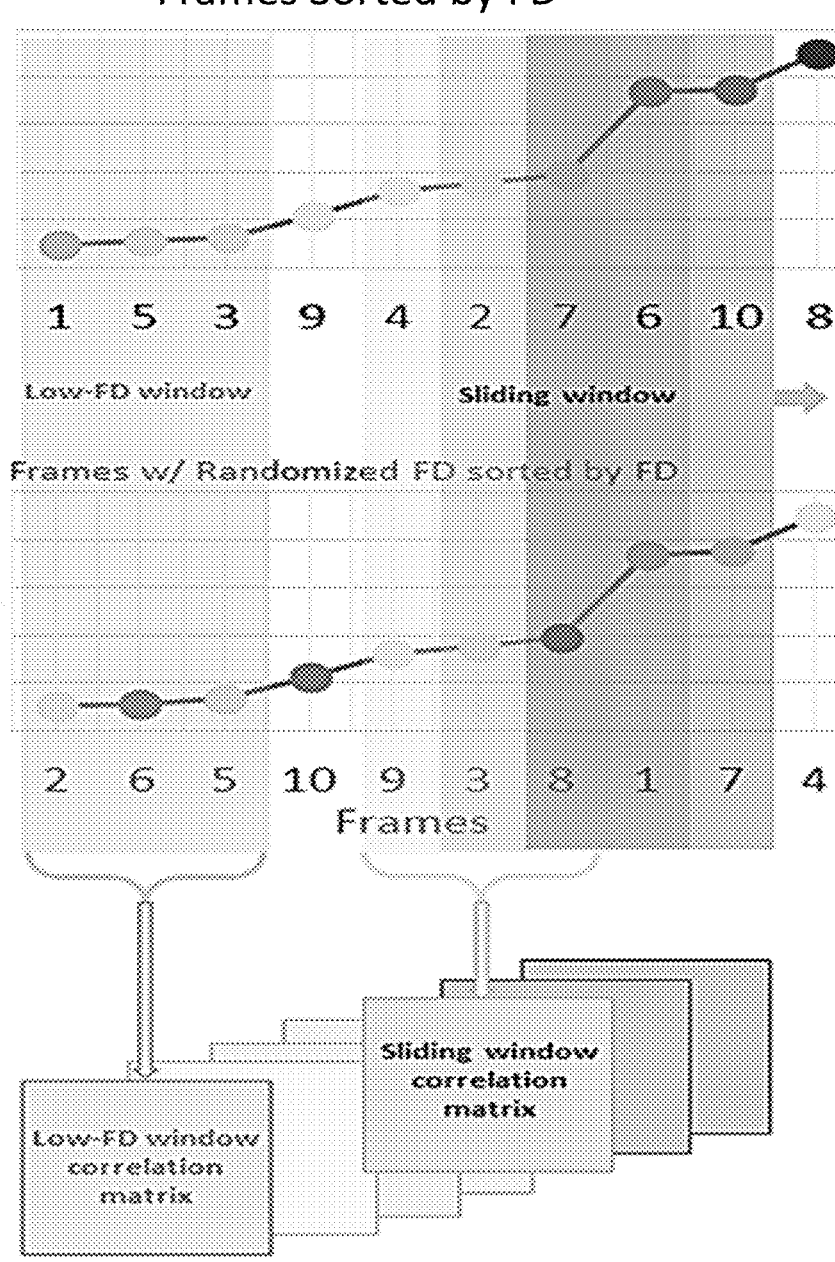

FIG. 19B illustrates a second step in conducting quantitative assessment using a quality measure described herein.

Figure 19C:
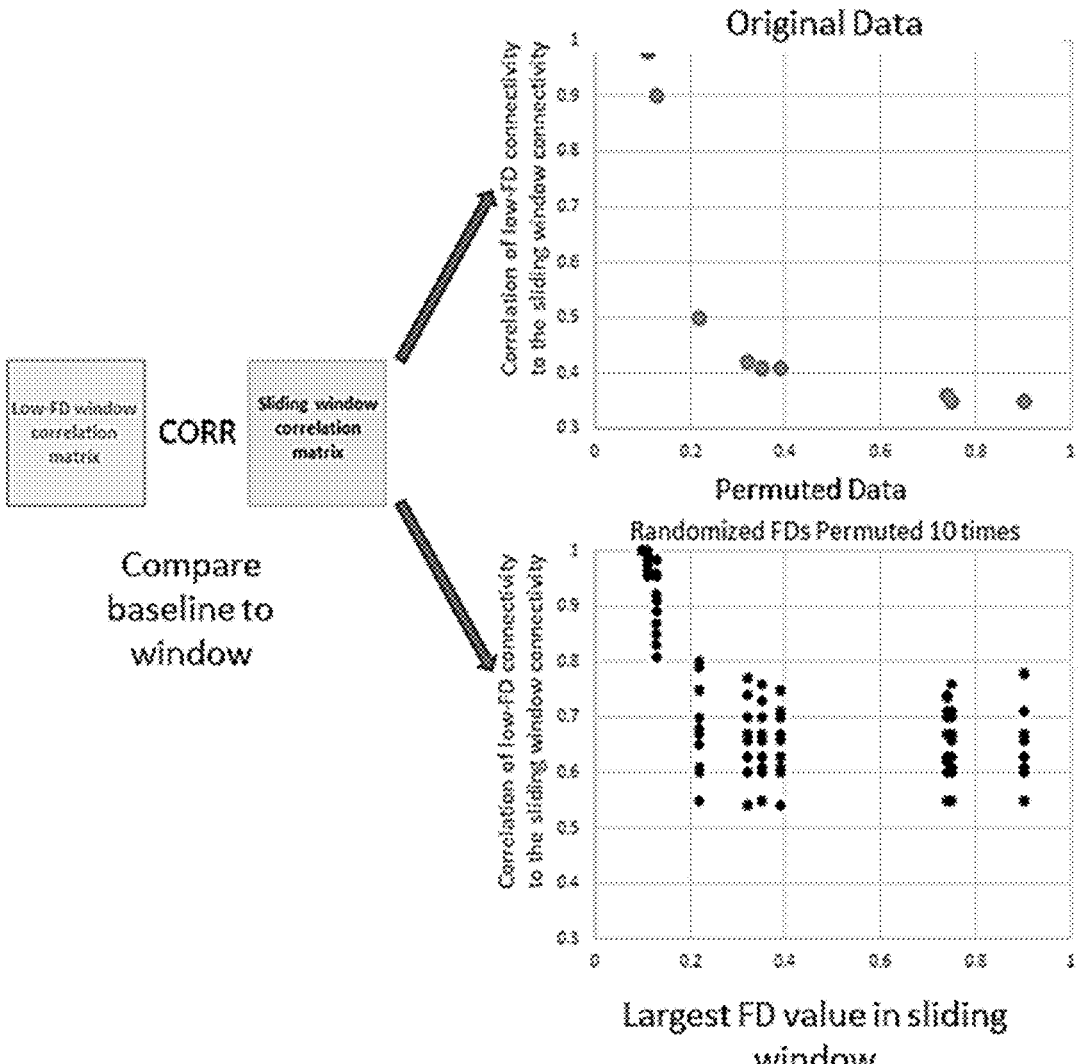

FIG. 19C illustrates a second and third step in conducting quantitative assessment using a quality measure described herein.

Figure 19D:
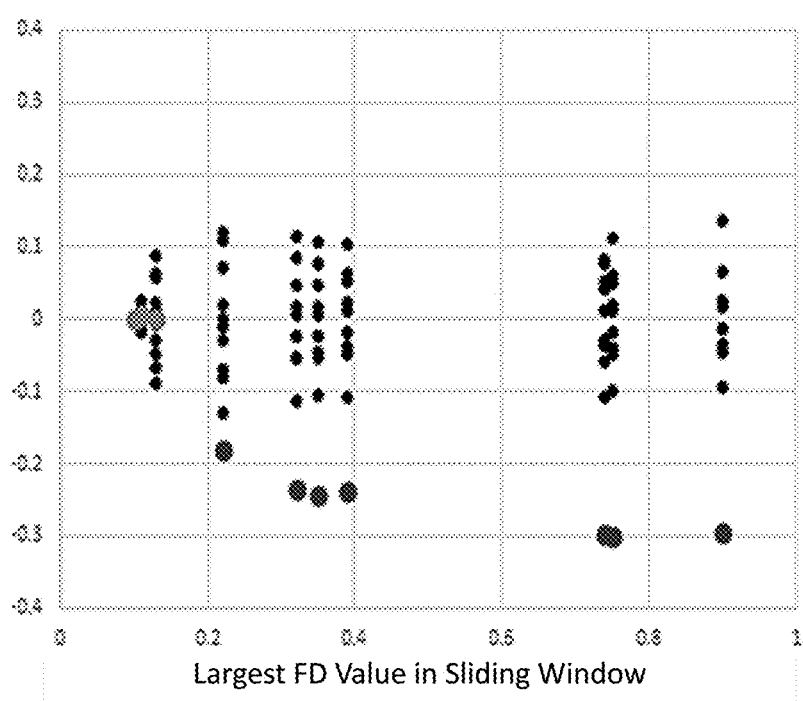

FIG. 19D illustrates a fifth and final step in in conducting quantitative assessment using a quality measure described herein.

Figure 20A:
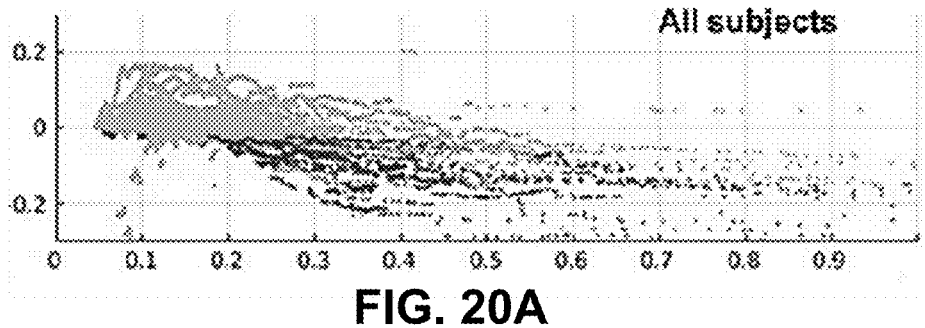

FIG. 20A shows the plotted rank of data quality metric-ordered outcomes across all subjects.

Figure 20B:
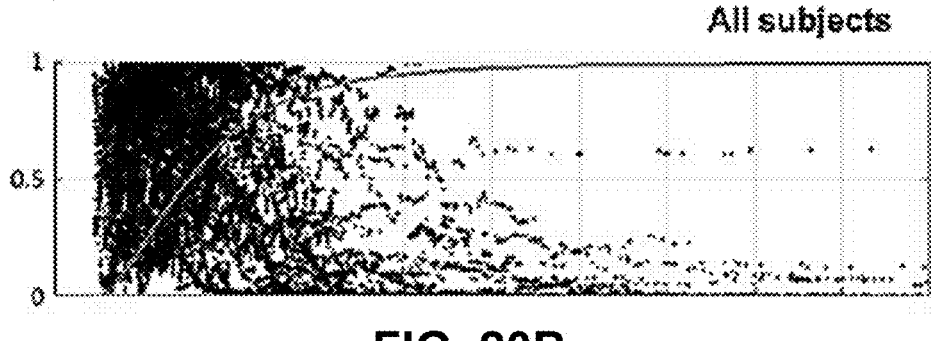

FIG. 20B shows the plotted rank of data quality metric-ordered outcomes across all subjects, in accordance with the disclosure.

Figure 20C:
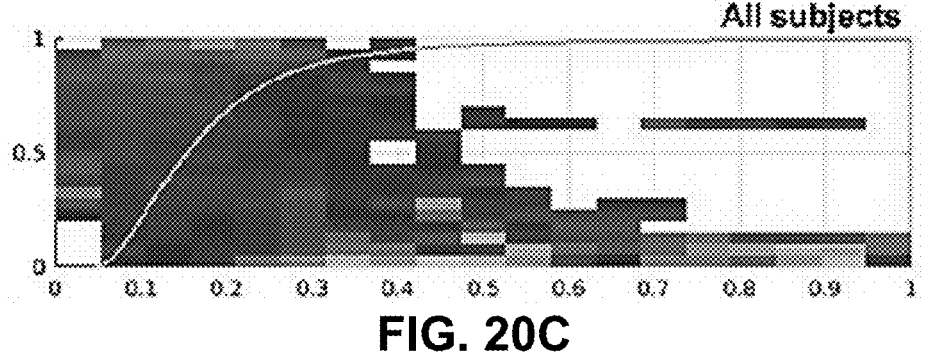

FIG. 20C shows the plotted rank of data quality metric-ordered outcomes across all subjects represented with a heat map.

Figure 21A:
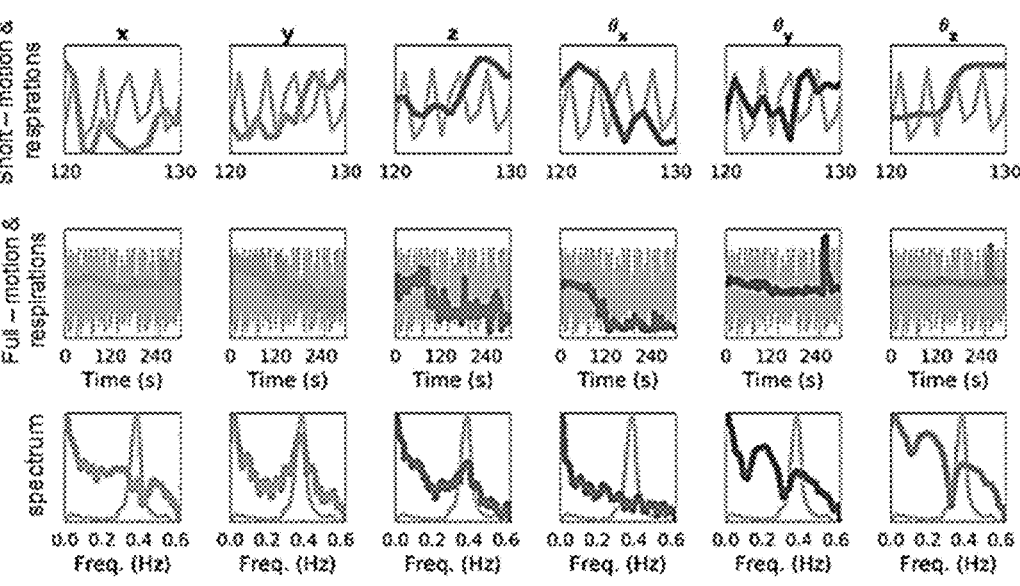

FIG. 21A shows motion estimates for six directions of the rigid body registration parameters in a single representative subject for multi-band data.

Figure 21B:
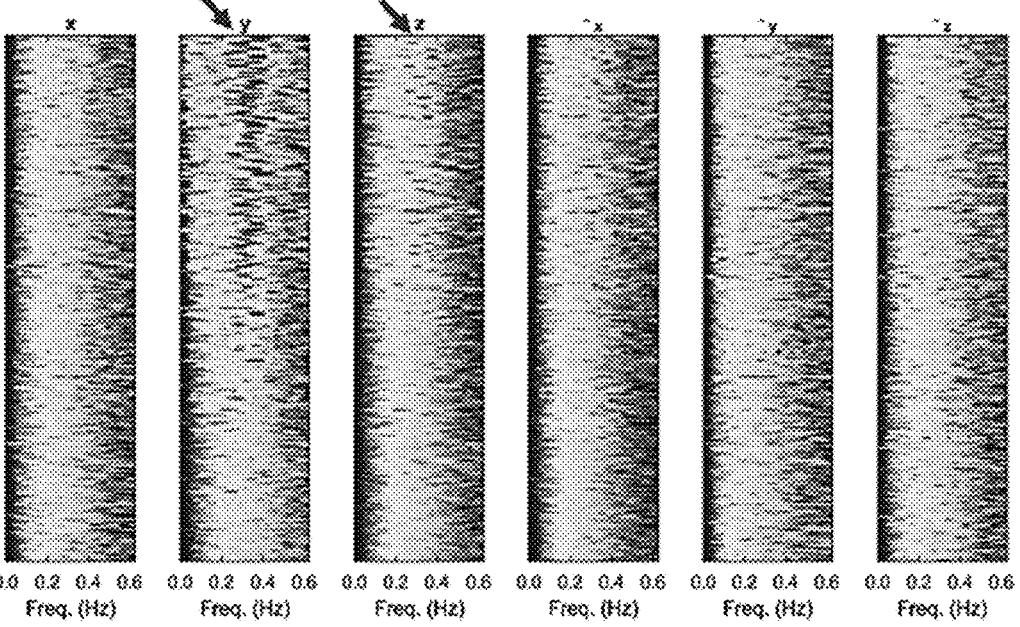

FIG. 21B shows the power spectrum across all subjects ranked from lowest to highest movers, whereby the highest movers are at the bottom of the figure for multi-band data.

Figures 22A, 22B:
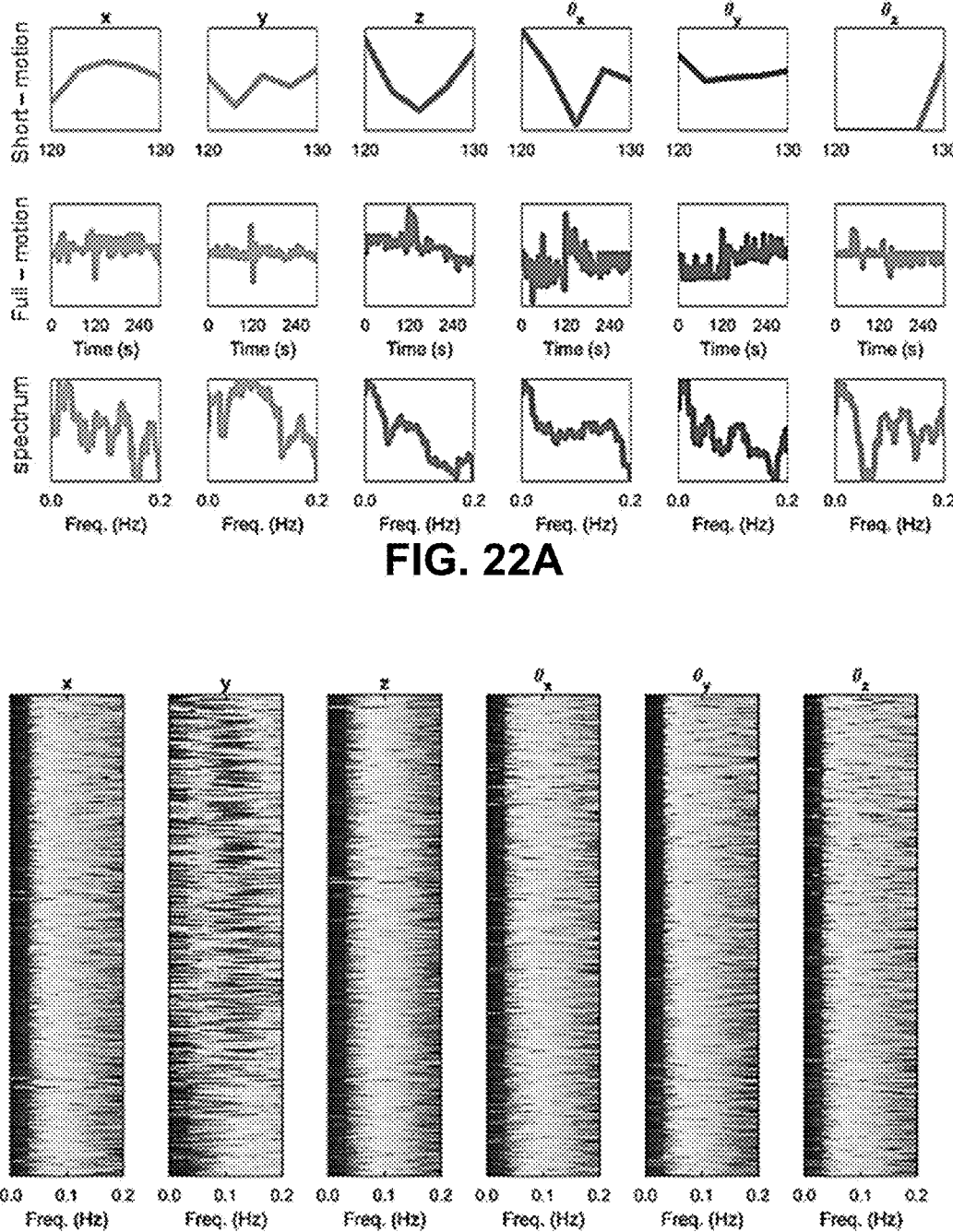

FIG. 22A shows motion estimates for six directions of the rigid body registration parameters in a single representative subject for single-band (e.g., single shot) acquisition data.

FIG. 22B shows the power spectrum across all subjects ranked from lowest to highest movers, whereby the highest movers are at the bottom of the figure for single-band data.

Figure 22C:
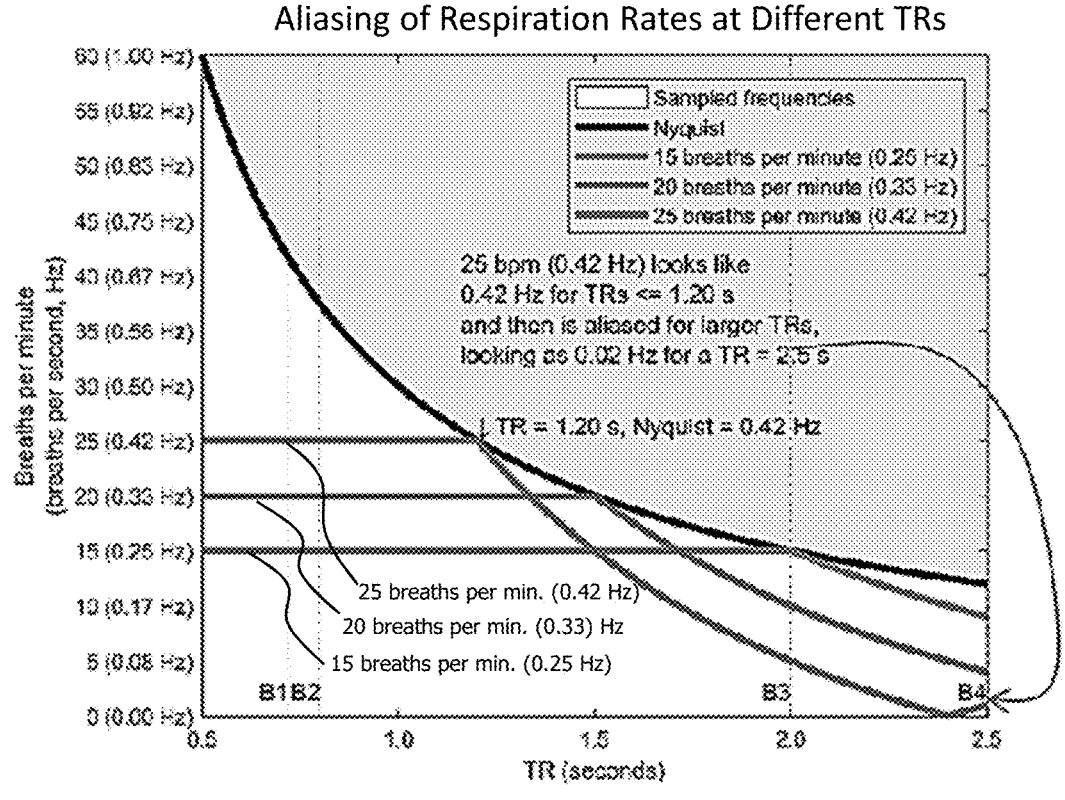

FIG. 22C shows data illustrating aliasing of respiration rates at different TRs (e.g., sampling rates).

FIG. 22D shows data for respiration rates at TR=0.72 s.

FIG. 22E shows data for respiration rates at TR=0.80 s.

FIG. 22F shows data for respiration rates at TR=2.00 s.

FIG. 22G shows data for respiration rates at TR=2.50 s.

Figure 23A:
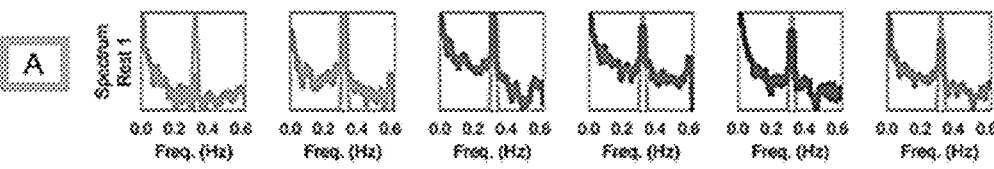

FIG. 23A shows movement spectra for respiration rate 0.33 Hz at TR=0.8 ms.

Figure 23B:
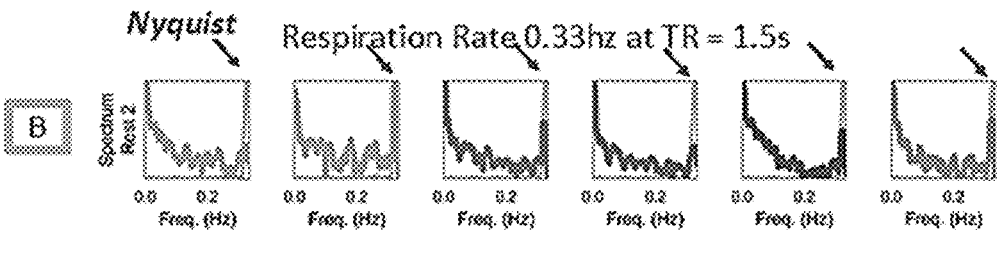

FIG. 23B shows movement spectra for respiration rate 0.33 Hz at TR=1.5 s.

Figure 23C:
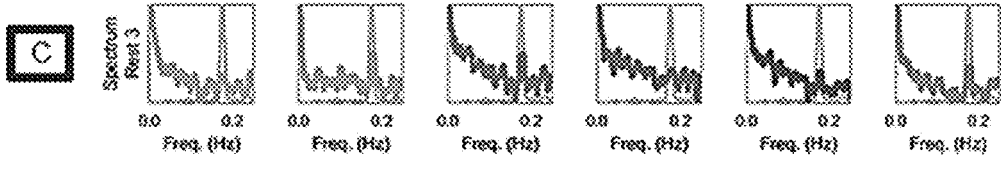

FIG. 23C shows movement spectra for respiration rate 0.33 Hz at TR=2.0 s.

Figure 23D:
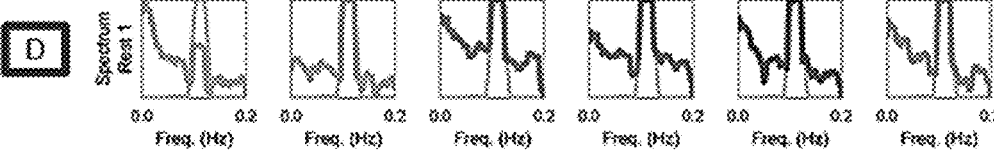

FIG. 23D shows movement spectra for respiration rate 0.33 Hz at TR=2.5 s.

Figure 23E:
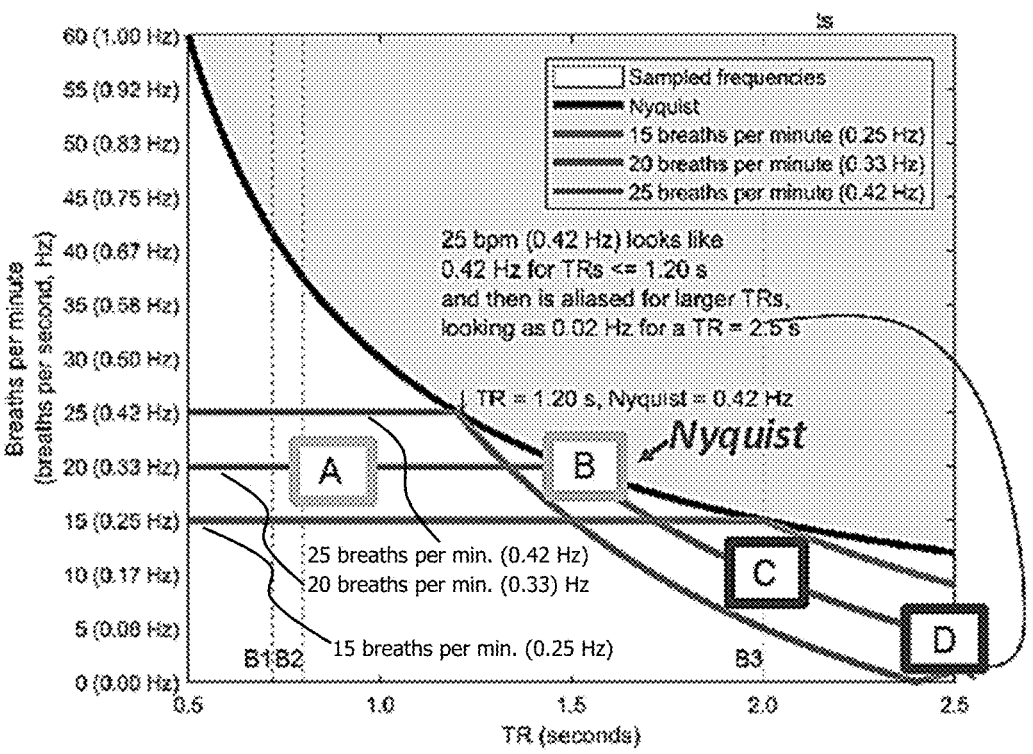

FIG. 23E is a graph illustrating aliasing of respiration rates at different TRs correlating to data shown in FIGS. 23A, 23B, 23C, and 23D.

Figure 24A:
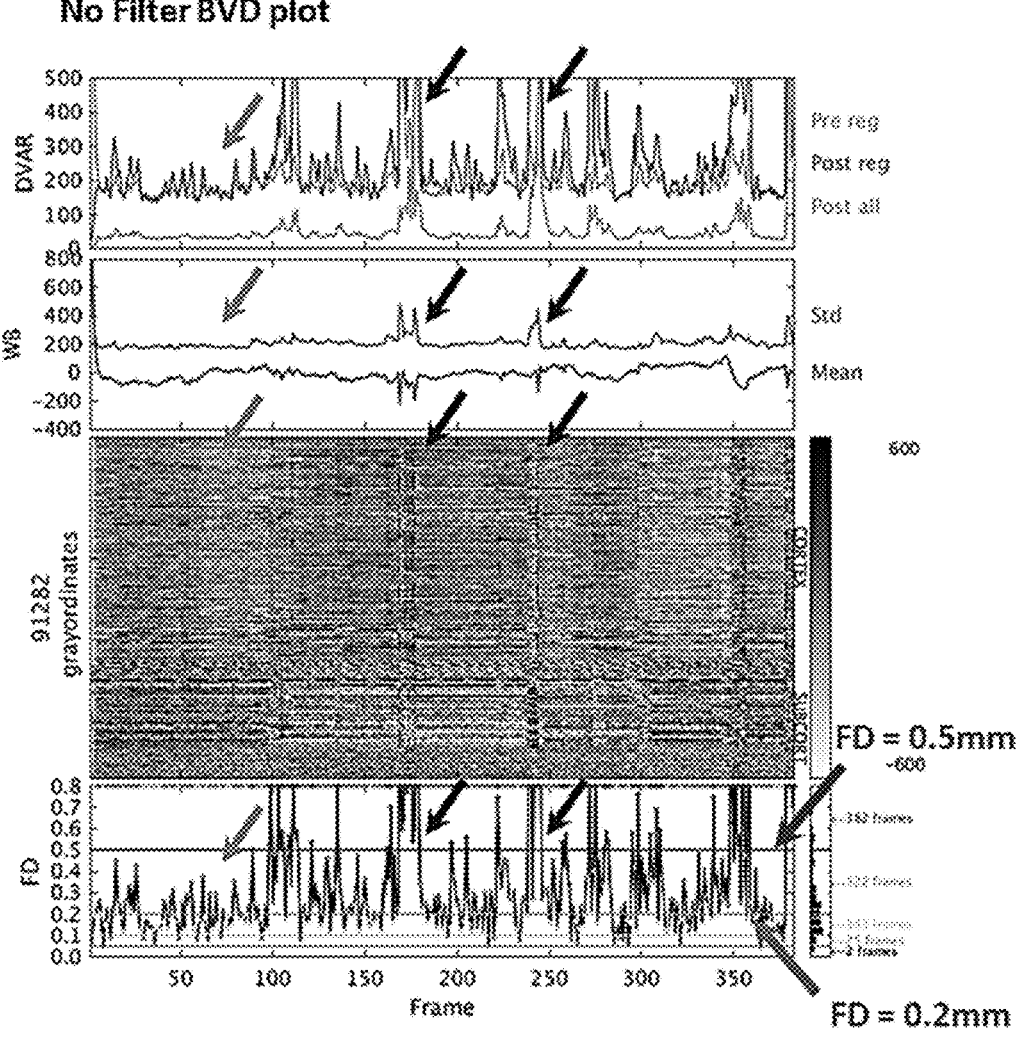

FIG. 24A qualitatively shows the result of implementing no filter on a BVD plot.

Figure 24B:
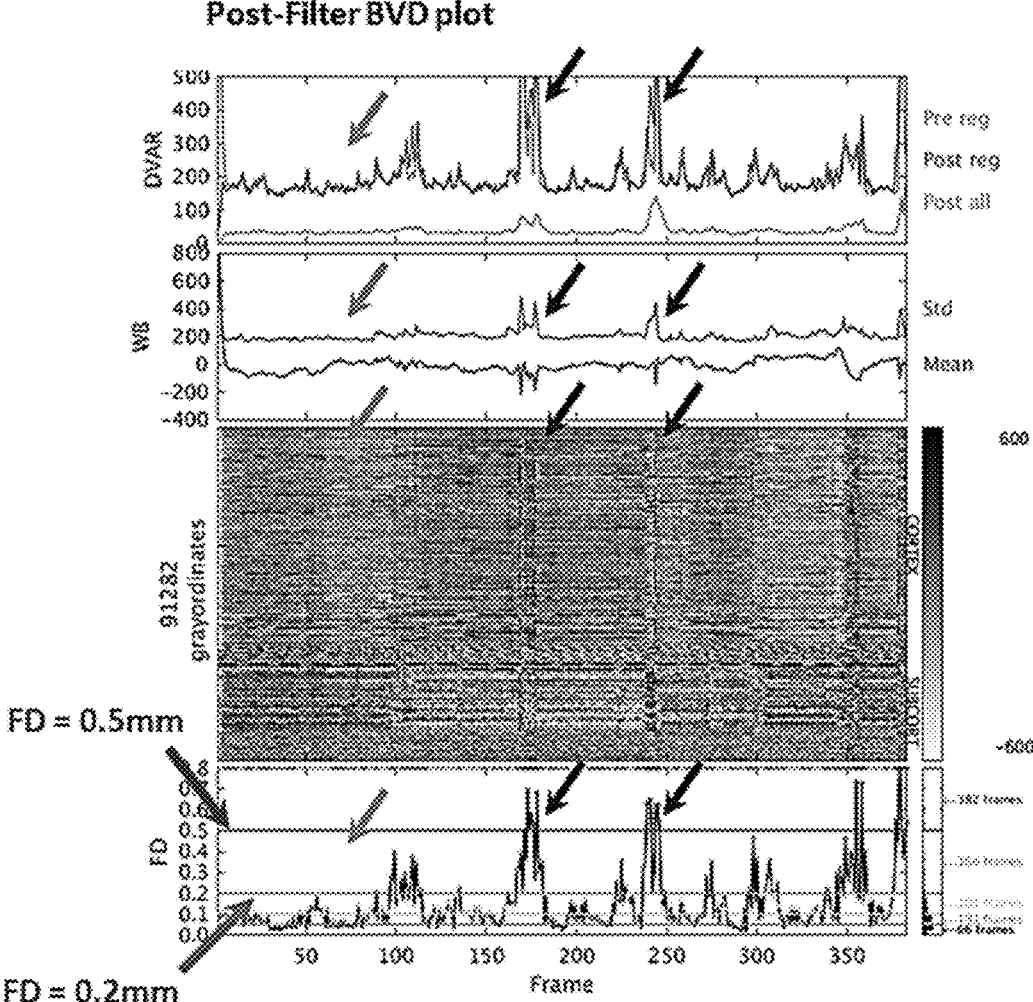

FIG. 24B qualitatively shows the result of implementing a general filter on a BVD plot.

Figure 24C:
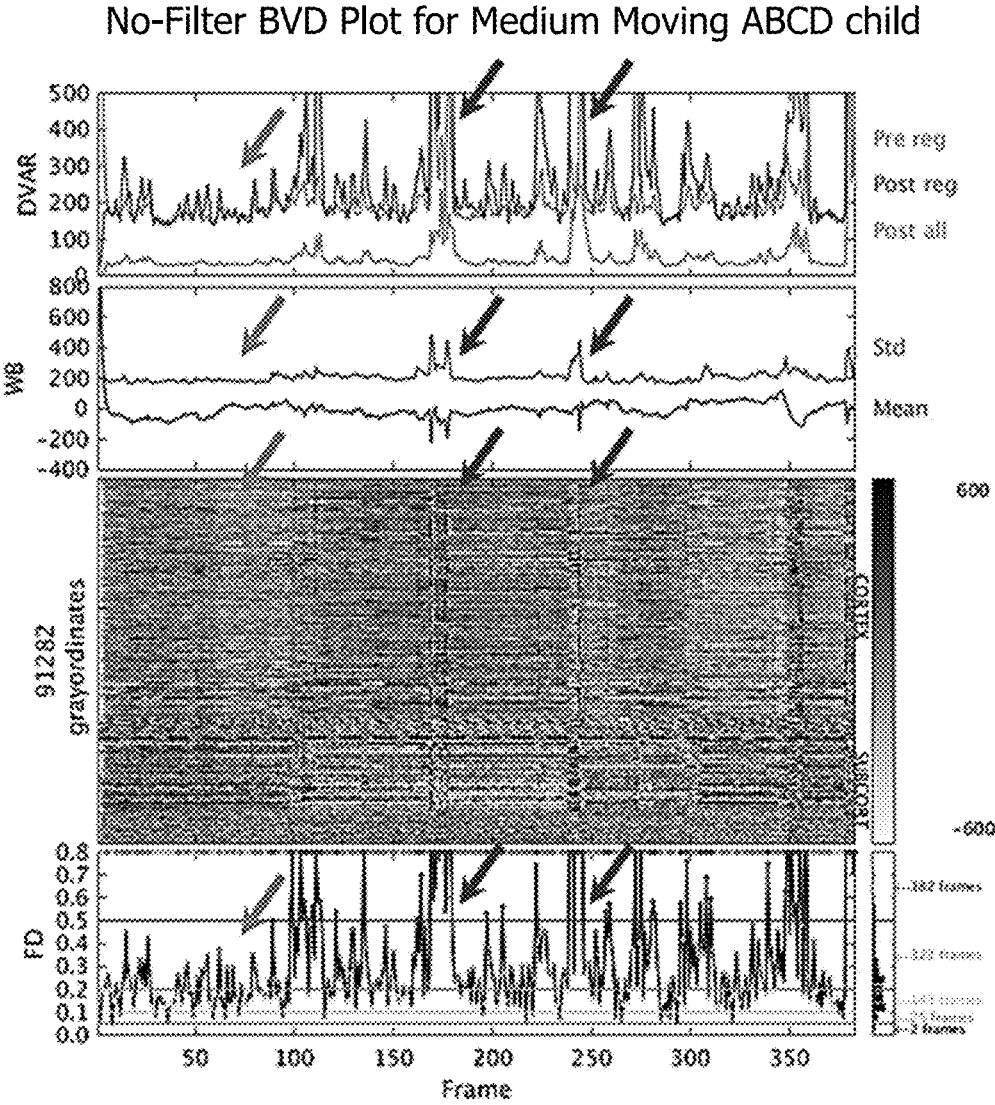

FIG. 24C qualitatively shows the result of implementing no filter on a BVD plot for a medium moving ABCD child.

Figure 24D:
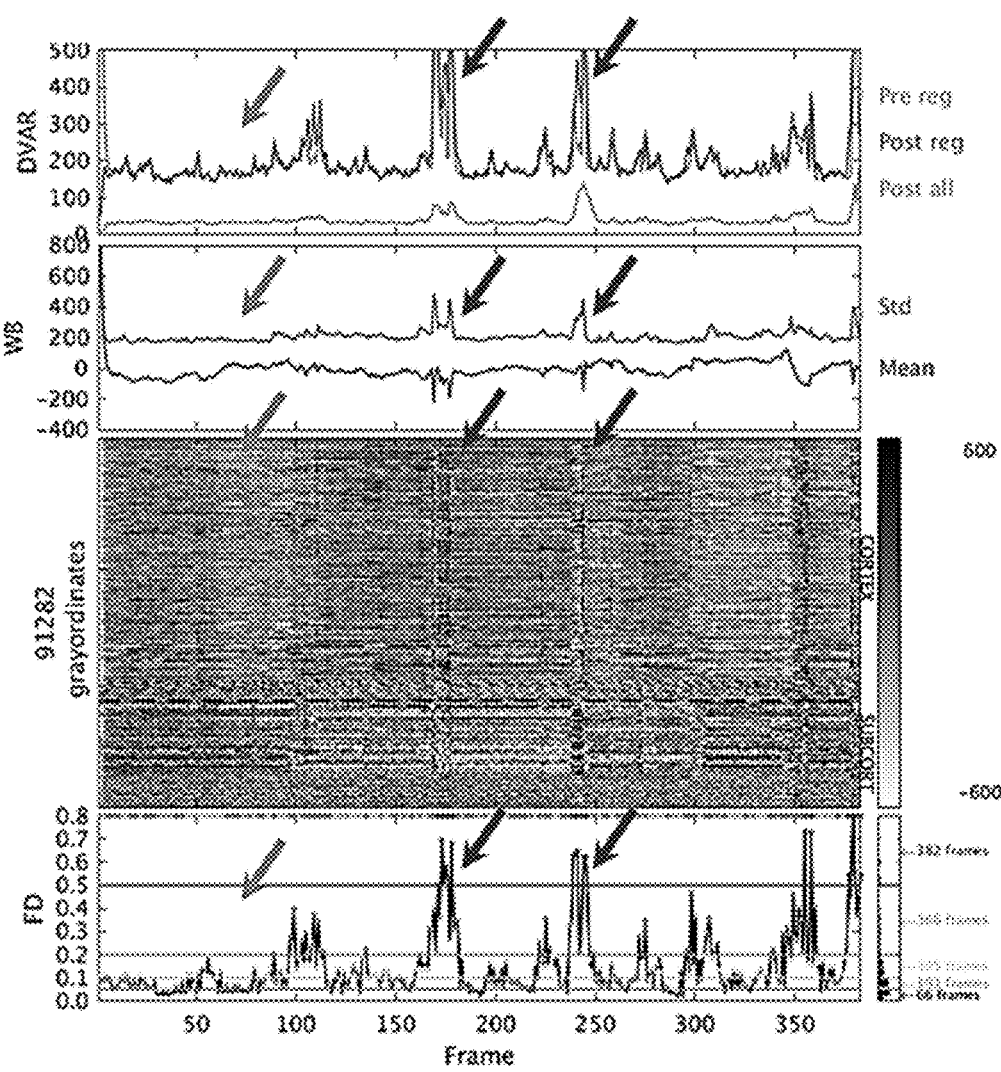

FIG. 24D qualitatively shows the result of implementing a general filter on a BVD plot for the medium moving ABCD child of FIG. 24C.

Figure 25A:
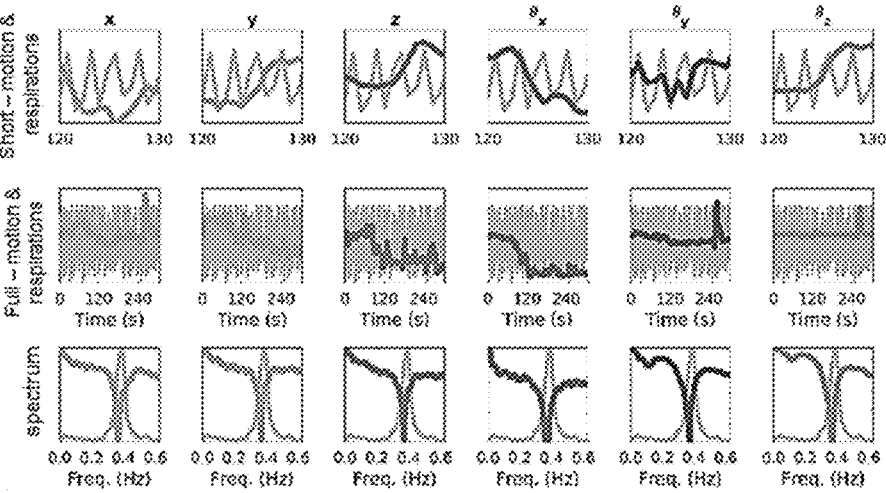

FIG. 25A provides a replicate of the data provided in FIG. 21A after implementing a general filter.

Figure 25B:
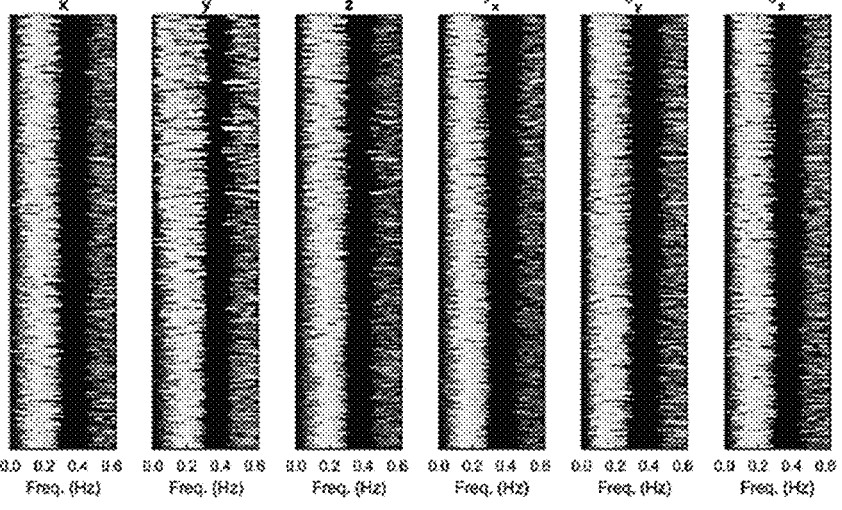

FIG. 25B provides a replicate of the data provided in FIG. 21B after implementing a general filter.

Figure 26A:
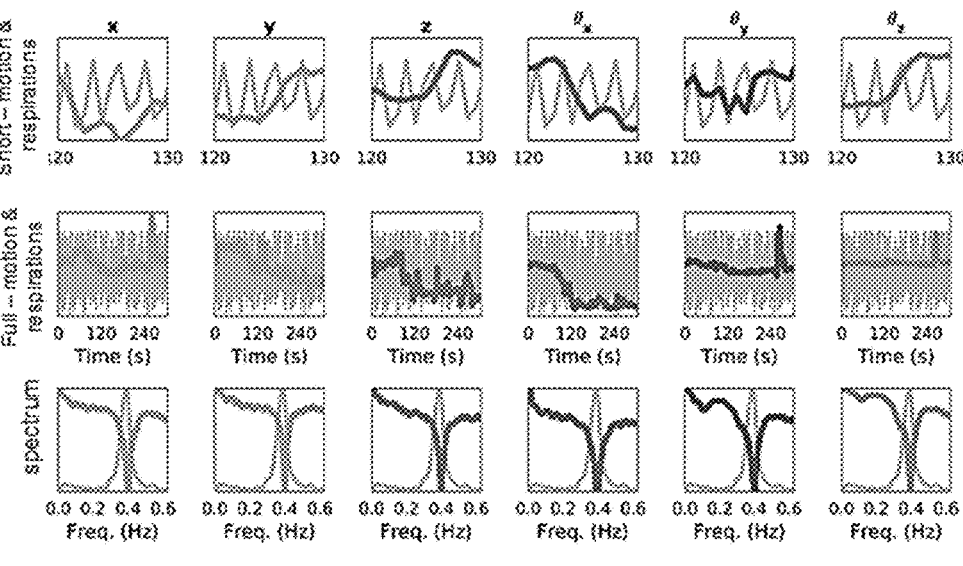

FIG. 26A provides a replicate of the data provided in FIG. 21A after implementing a subject-specific filter.

Figure 26B:
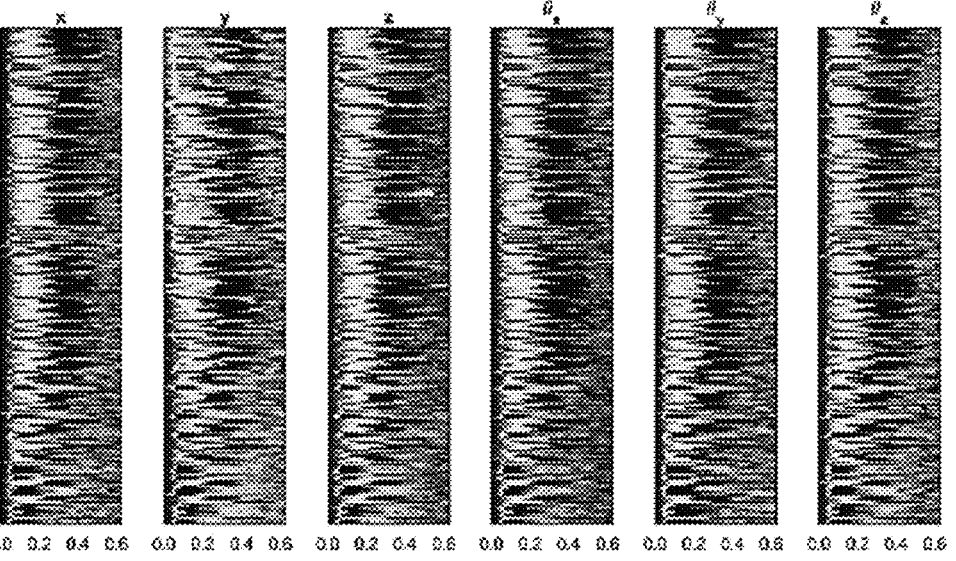

FIG. 26B provides a replicate of the data provided in FIG. 21B after implementing a subject-specific filter.

FIG. 27A shows a quantitative measurement of motion estimates with no filter application for a specific subject.

FIG. 27B shows a quantitative measurement of motion estimates after implementing a general filter for a specific subject.

FIG. 27C shows a quantitative measurement of motion estimates after implementing a run-specific filter for a specific subject.

Figures 27D, 27E, 27F:
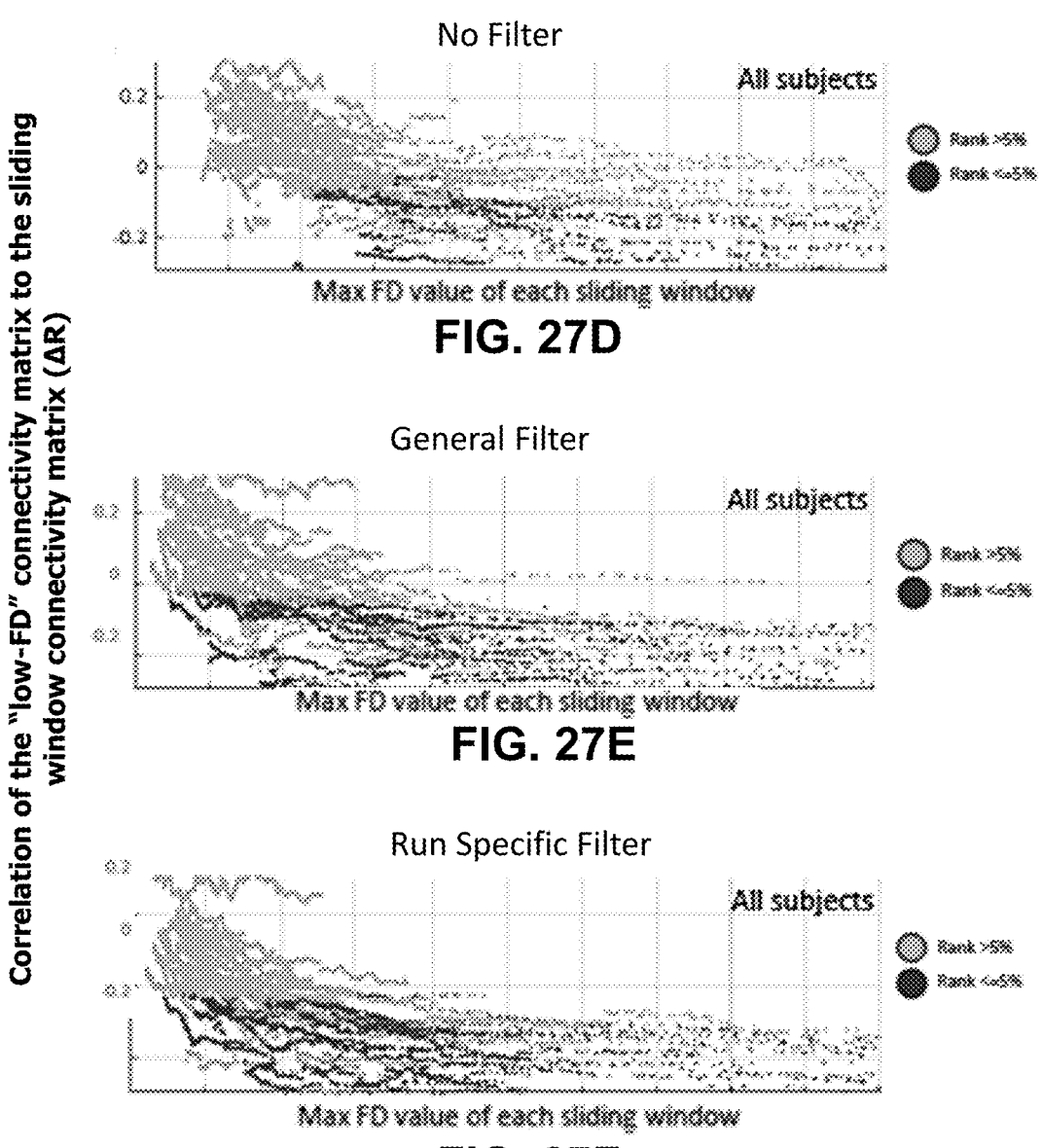

FIG. 27D shows a quantitative measurement of motion estimates with no filter application for all subjects.

FIG. 27E shows a quantitative measurement of motion estimates after implementing a general filter for all subjects.

FIG. 27F shows a quantitative measurement of motion estimates after implementing a run-specific filter for all subjects.

Figure 27G:
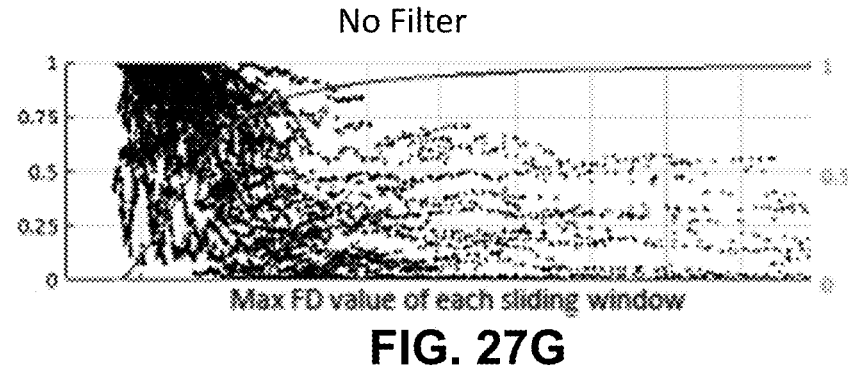

FIG. 27G shows a rank of each point in relation to the null distribution for motion estimates with no filter application.

Figure 27H:
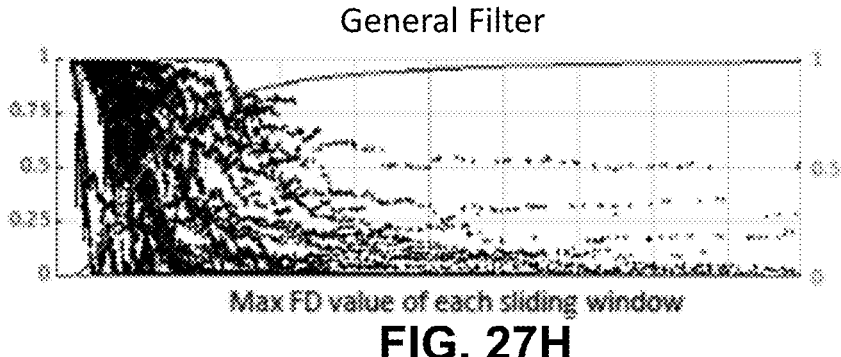

FIG. 27H shows a rank of each point in relation to the null distribution for motion estimates after implementing a general filter.

Figure 27I:
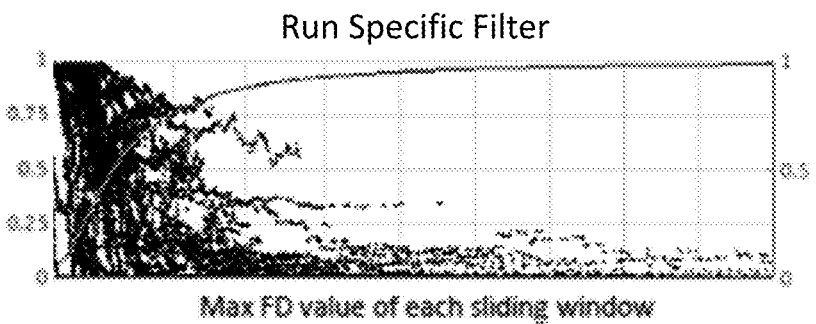

FIG. 27I shows a rank of each point in relation to the null distribution for motion estimates after implementing a run-specific filter.

FIG. 27J is a heat map summarizing the data shown in FIG. 27G.

FIG. 27K is a heat map summarizing the data shown in FIG. 27H.

FIG. 27L is a heat map summarizing the data shown in FIG. 27I.

Figure 28:
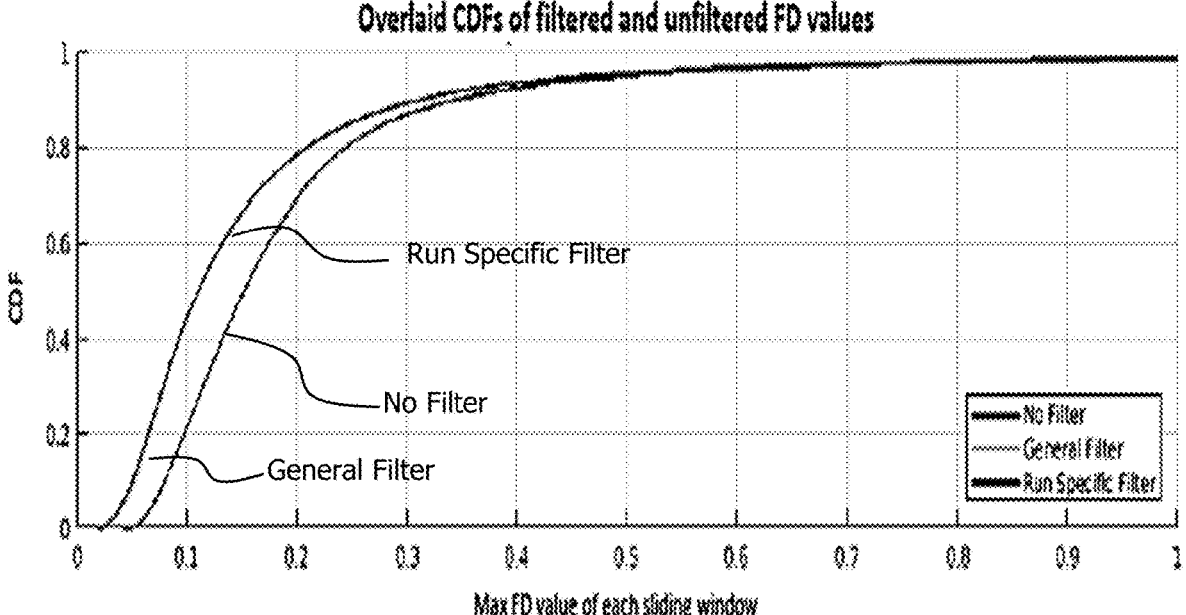

FIG. 28 shows a plot comparing CDFs of filtered and unfiltered FD values illustrating significant differences between no filter application and general filter application as well as between no filter application and run-specific filter application.

Figure 29A:
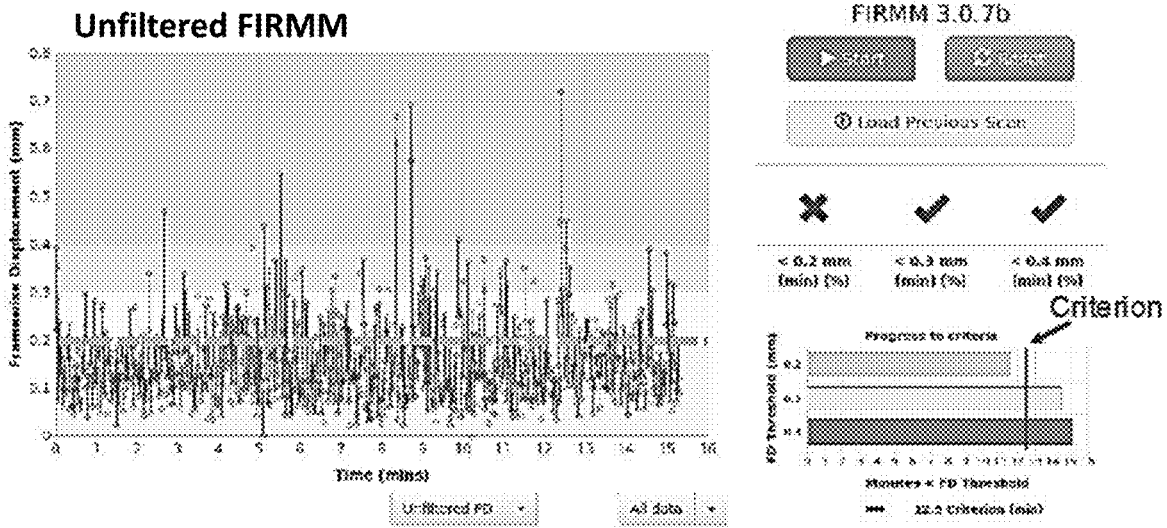

FIG. 29A provides a screen-shot image of an unfiltered FIRMM GUI, in accordance with one aspect of the disclosure.

Figure 29B:
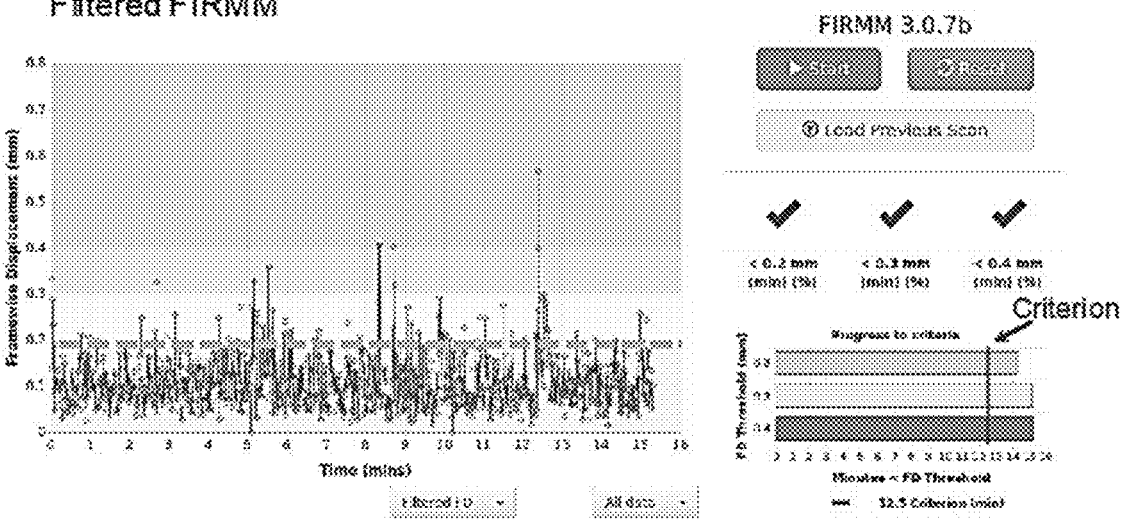

FIG. 29B provides a screen-shot image of a filtered FIRMM GUI, in accordance with one aspect of the disclosure.

Figure 29C:
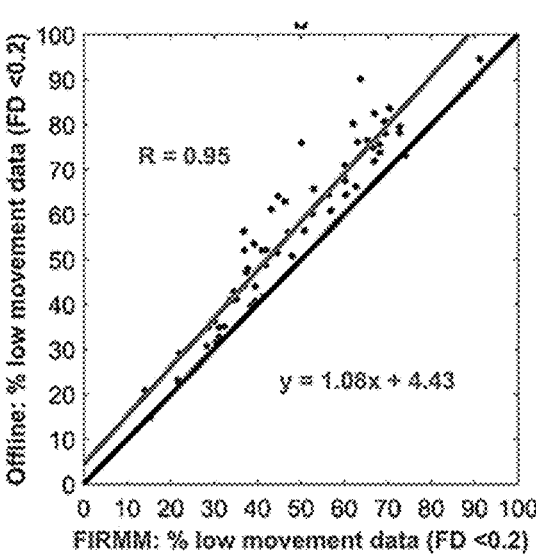

FIG. 29C is a graph showing percentage of unfiltered low movement FIRMM data compared to percentage of low movement Offline data.

Figure 29D:
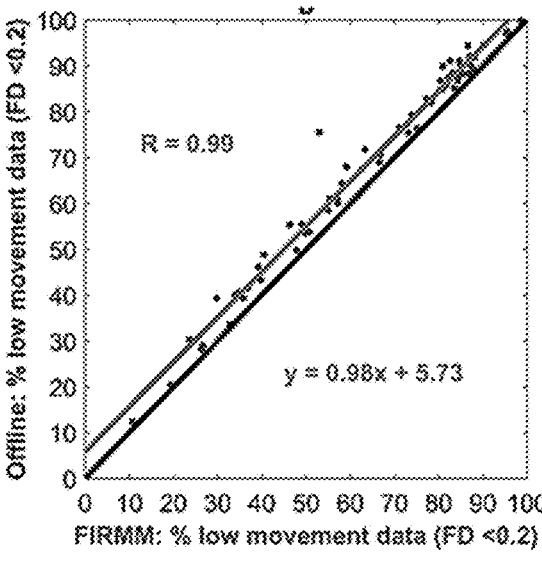

FIG. 29D is a graph showing percentage of filtered low movement FIRMM data compared to a percentage of low movement Offline data.

Figure 30A:
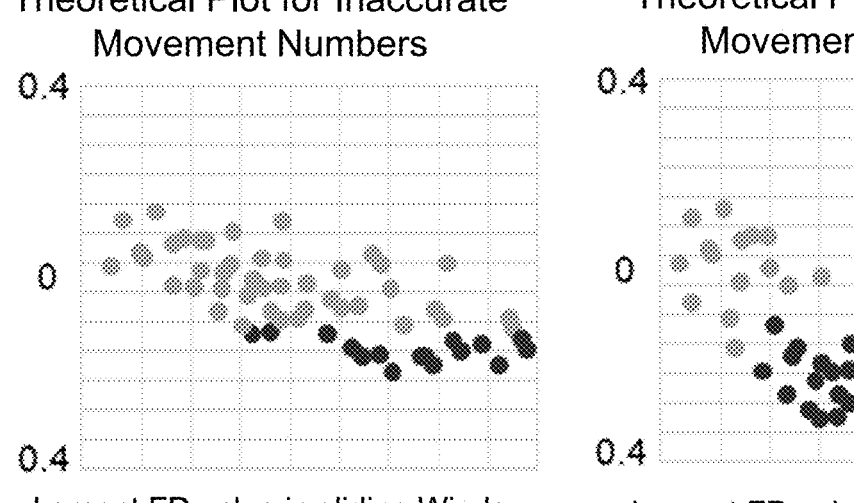

FIG. 30A provides theoretical plots for inaccurate and accurate movement numbers for all subject windows.

Figure 30B:
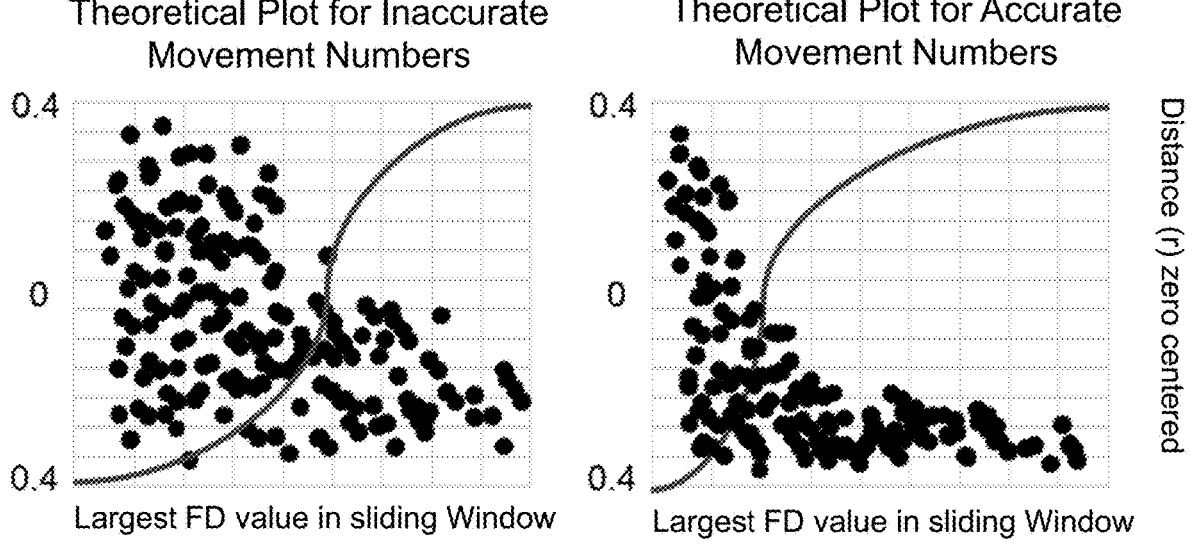

FIG. 30B provides theoretical plots for inaccurate and accurate movement numbers with each window ranked against Null.

Figure 30C:
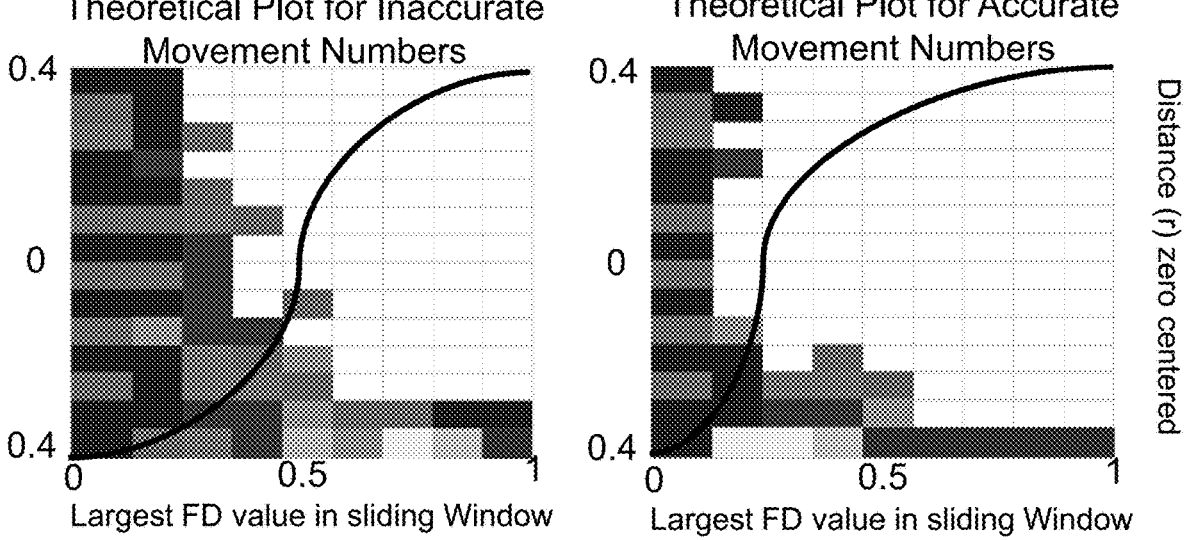

FIG. 30C provides theoretical plots for inaccurate and accurate movement numbers with each window ranked against Null binned.

Figure 31:
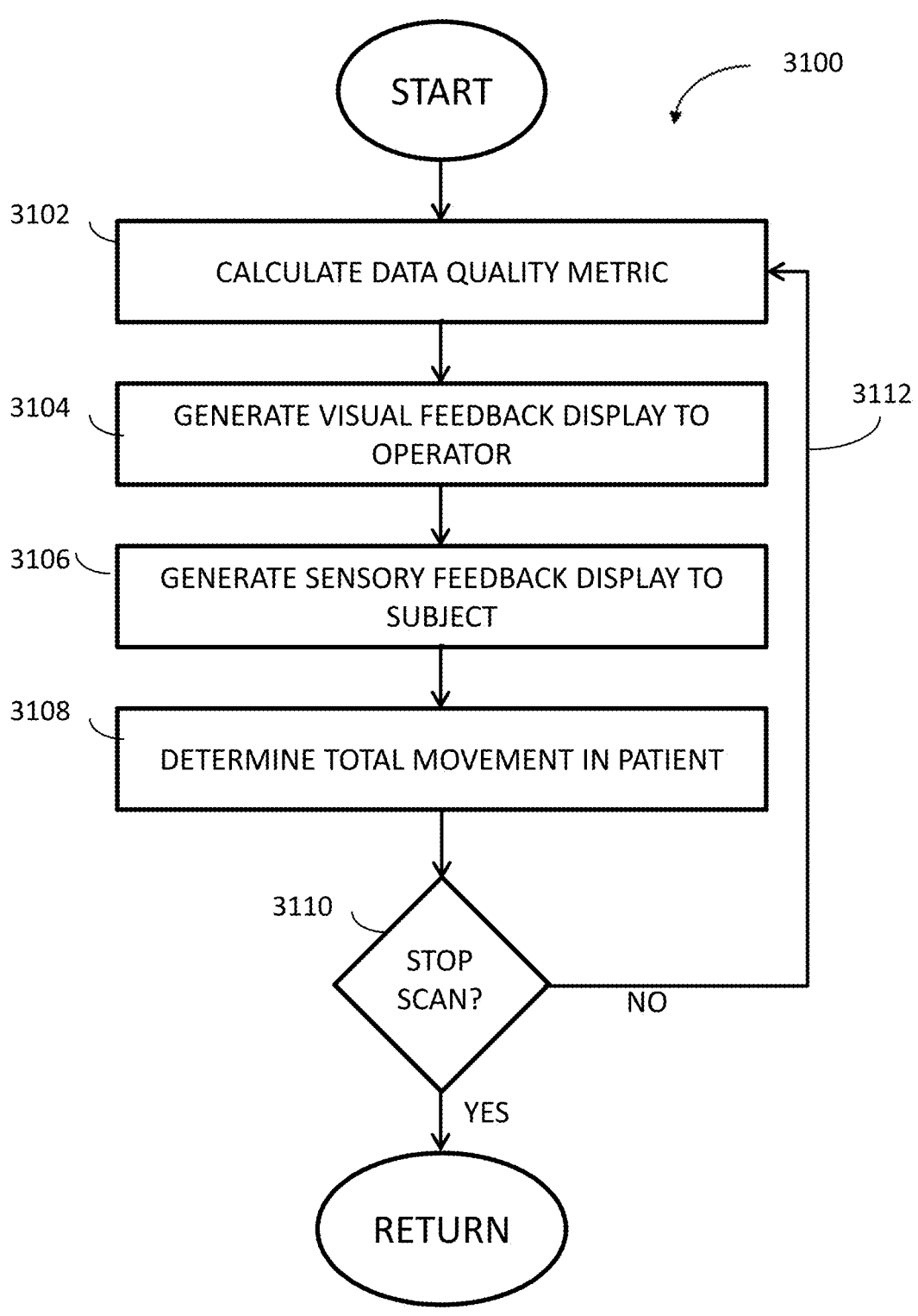

FIG. 31 is a flow chart illustrating the generation of a sensory feedback display based on a data quality metric, in accordance with one aspect of the disclosure.

FIG. 32 is a flow chart illustrating a use of an $N^{th}$ order filter to remove respiration-related artifacts from motion estimates prior to calculating framewise displacement, in accordance with one aspect of the disclosure.

FIG. 33 is a flow chart illustrating a use of an adaptive filter to remove respiration-related artifacts from motion estimates prior to calculating framewise displacement, in accordance with one aspect of the disclosure.

Figure 34:
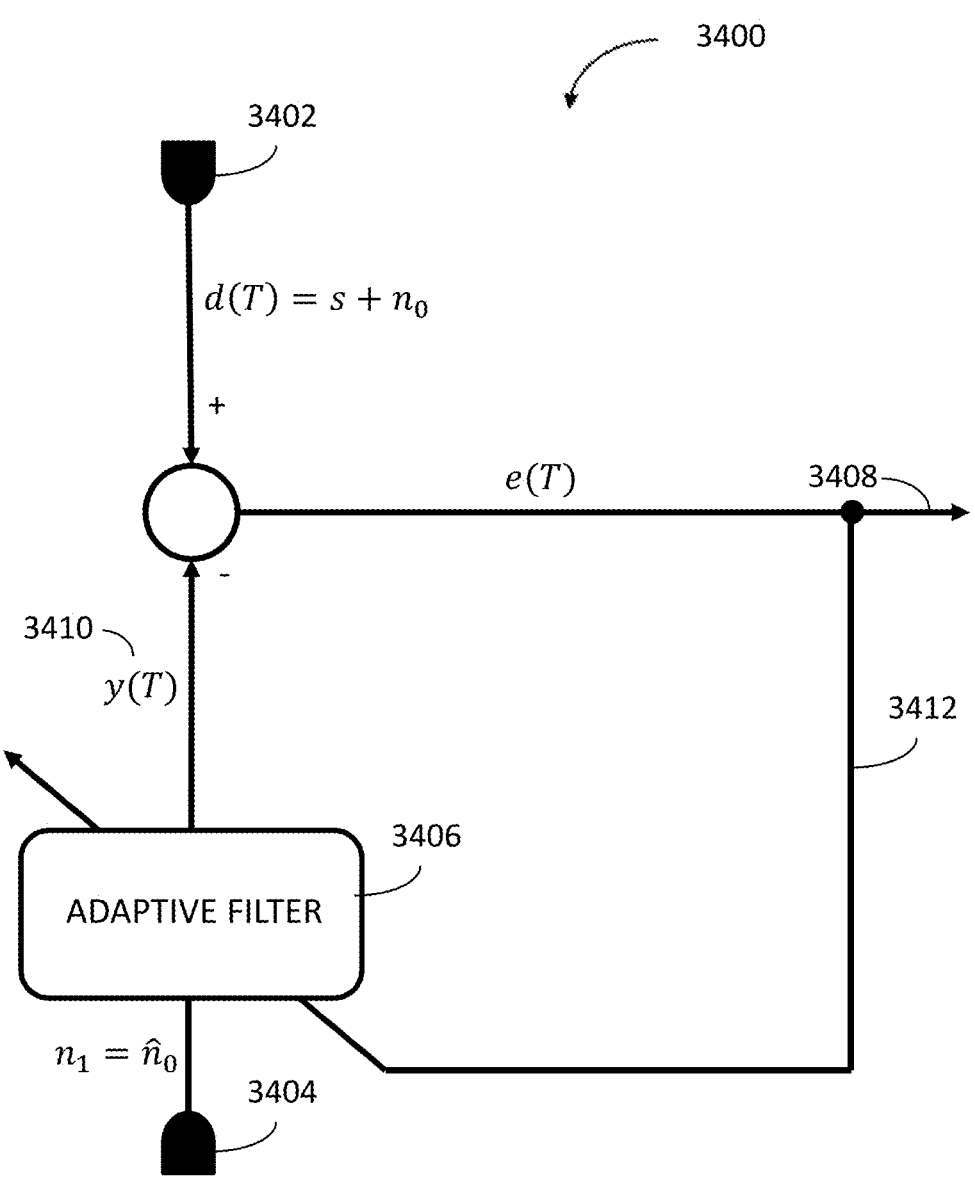

FIG. 34 is a schematic diagram illustrating the development of an adaptive filter to remove respiration-related artifacts from motion estimates, in accordance with one aspect of the disclosure.

DETAILED DESCRIPTION

In various aspects, Framewise Integrated Real-time MRI Monitoring (FIRMM) systems, devices, and methods for real-time monitoring and prediction of motion of a body part of a patient including, but not limited to, head motion during MRI scanning are disclosed. More specifically, methods, computer-readable storage devices, and systems are described for aligning magnetic resonance imaging (MRI) data, such as frames collected from an MRI scan, to a reference image in order to monitor motion of a patient's body part during an MRI scan. In various aspects, the reference image provides a common basis from which the displacement or motion of all frames may be obtained and compared.

Figure 1:
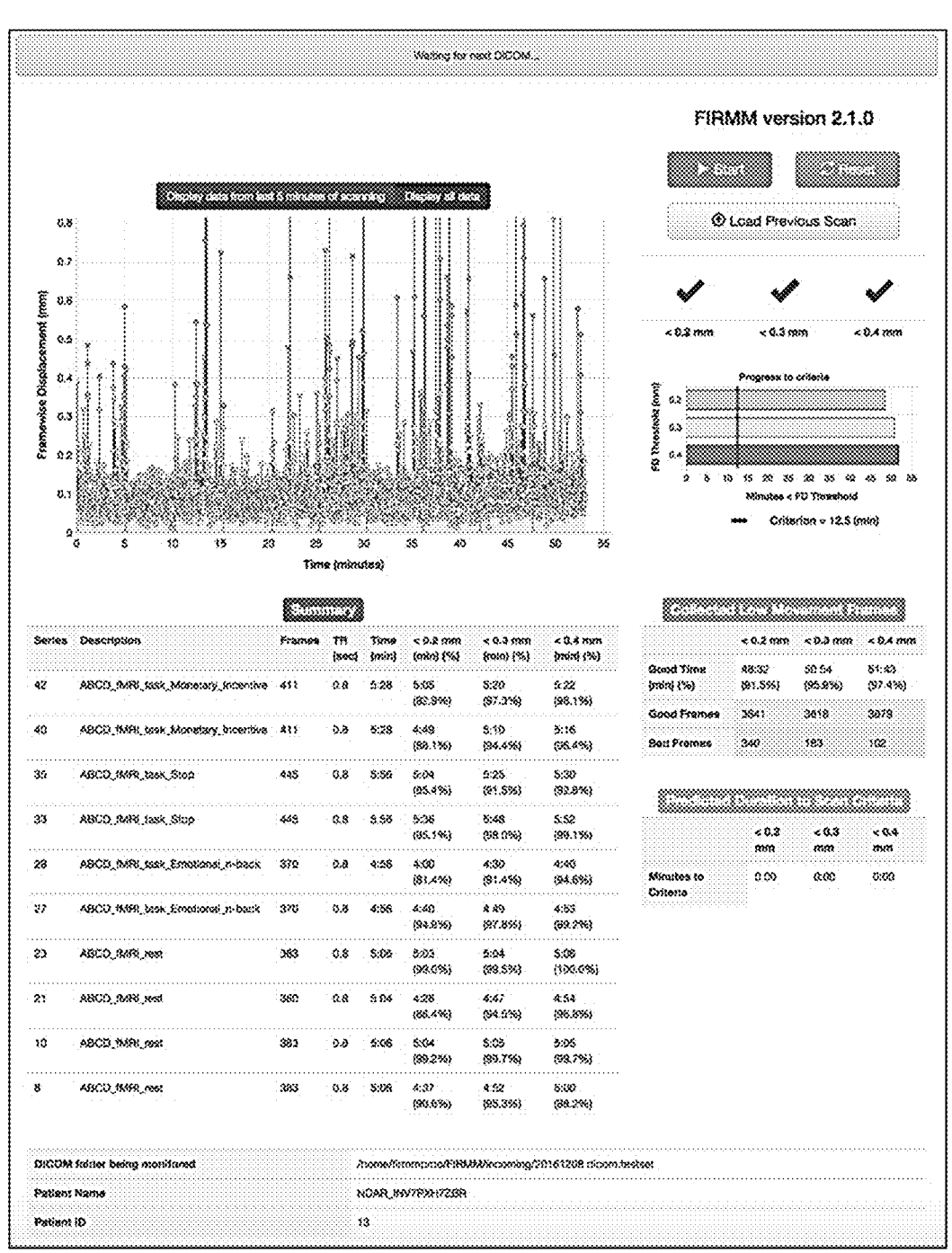
FIG. 1 shows a FIRMM (Framewise Integrated Real-time MRI Monitoring) graphical user interface (GUI), in accordance with one aspect of the disclosure.

In various aspects, the Framewise Integrated Real-time MRI Monitoring (FIRMM) computer implemented method simultaneously improves MRI data quality and reduces costs associated with MRI data acquisition. In one aspect, the FIRMM method is implemented in the form of a software suite that calculates and displays data quality metrics and/or summary motion statistics in real time during an MRI data acquisition. By way of non-limiting example, a screen shot of a GUI generated during brain MRI data acquisition is shown in FIG. 1. The FIRMM methods and systems are typically described herein in the context of functional MRI data acquisition, but in various other aspects the FIRMM methods and systems disclosed herein are suitable for real-time monitoring of head and body motion during other structural or anatomical MRI sequences, including but not limited to those that utilize motion navigators.

The disclosed FIRMM systems and methods overcome one or more of at least several shortcomings of previous systems. To address the shortcomings associated with 'over-scanning,' by previous systems to compensate for motion-distorted data, the FIRMM systems and methods disclosed herein provide real-time feedback to both the scanner operator and the subject undergoing the scan. More specifically, the disclosed FIRMM systems and methods provide sensory feedback to a subject during the scan based on the data quality metrics and summary motion statistics calculated in real time, thereby enabling the subject to monitor and adjust their movements accordingly (e.g., remain still) in response to the provided feedback. Further, the disclosed FIRMM systems and methods provide stimulus conditions, such as viewing a fixation crosshair or a movie clip, to simultaneously engage the subject while also providing real-time feedback to the subject.

The disclosed FIRMM systems and methods further address the shortcomings described above by enabling a scanner operator to continue each scan until the desired number of low-movement data frames have been acquired by, as non-limiting examples, (i) predicting the number of usable data frames that will be available at the end of the scan; (ii) predicting the amount of time a given subject will likely have to be scanned until the preset time-to-criterion (minutes of low-movement FD data) has been acquired; and (iii) enabling for the selection and deselection of specific individual scans for inclusion in the actual and predicted amount of low-movement data.

Previously, motion estimates for brain MRIs were typically analyzed offline, either after data collection was completed for a given subject, or more commonly, in large batches after data collection for the whole cohort had been completed. Postponing head motion analyses is expensive and risky, especially when scanning a previously unstudied patient population and after making changes to the data collection protocol or personnel.

More specifically, real-time information about head motion can be used to reduce head motion in multiple different ways including, but not limited to: 1) by influencing the behavior of MRI scanner operators and 2) by influencing MRI scanning subject behavior. Scanner operators may be alerted about any sudden or unusual changes in head movement and are enabled to interrupt such scans to investigate if the subject has started moving more because they have grown uncomfortable and whether a bathroom break, blanket, repositioning or other intervention could make them feel more comfortable. In some aspects, the FIRMM methods further include options for feeding information about head motion back to the subject, post-scan and/or in real time. The disclosed FIRMM methods allow scanner operators to find the sweet spot that provides the required amount of low-movement data at the lowest cost. A scan could be stopped, the subject could be further instructed or reminded on ways to try remaining still, and the scan could be re-acquired.

The FIRMM methods and systems disclosed herein were verified for accuracy and cost savings using several large rs-fcMRI datasets obtained from different patient and control cohorts as described below. In addition, the FIRMM methods and systems disclosed herein were further tested for real-world utility and durability using an additional cohort of 29 participants.

In one aspect, the FIRMM method includes receiving a frame, such as an image frame, from a magnetic resonance imaging system and aligning the frame to a reference image. In various aspects, the reference image may be a single frame selected from the frames collected from the MRI scan including, but not limited to, the first frame, a navigator frame, or any other suitable frame selected from a plurality of frames collected during an MRI scan. In other aspects, the reference image may be an image retrieved from an ana- tomical atlas. In various other aspects, the reference image may be an image retrieved from an anatomical atlas. In various additional aspects, the reference image may be a composite or combination of two or more frames collected during an MRI scan including, but not limited to, a mean of two or more frames. In one aspect, each current frame may be aligned to a previous frame collected immediately prior, which has been aligned iteratively with the reference image collected for a given MRI scan.

In certain aspects of the FIRMM method, aligning the frame to the reference image comprises a series of rigid body transforms, $T_i$, where i indexes the spatial registration of the frame i to the reference image, wherein each transform is calculated by minimizing or otherwise reaching a stop condition relative to a registration error, as expressed in Eqn. (1):

$$\varepsilon_i = \langle \left( sI_i\big(T(\vec{x})\big) - I_1(\vec{x}) \right)^2 \rangle; \qquad \text{Eqn. (1)}$$

where $I(\vec{x})$ is the frame intensity at locus $\vec{x}$ and s is a scalar factor that compensates for fluctuations in mean signal intensity, spatially averaged over at least a portion of the frame, such as a portion of the frame corresponding to an MRI image of the subject's body part, including, but not limited to, the head.

In various aspects, each transform is represented by a combination of rotations and displacements as described by Eqn. (2):

$$T_i = \begin{bmatrix} R_i & \dot{d}_i \\ 0 & 1 \end{bmatrix}; \qquad \text{Eqn. (2)}$$

where $R_i$ represents the 3×3 matrix of rotations including the three elementary rotations at each of the three axes (see Example 1 below) and $\dot{d}_i$ represents the 3×1 column vector of displacements.

In one aspect, the image frames are realigned using the 4dfp cross_realign3d_4dfp algorithm (see Smyser, C. D. et al. Cerebral cortex 20, 2852-2862, (2010), which is specifi- cally incorporated herein by reference in its entirety). In some aspects, the cross_realign3d_4dfp algorithm may be optimized for computational speed, including disabling of frame-to-frame image intensity normalization and the output of the alignment parameters only, rather than all realigned data.

In various aspects, the FIRMM method further includes calculating motion of a body part, such as a subject's head, between the frame and the immediately preceding frame. In various aspects, the motion of a body part, such as a subject's head, is calculated from multiple frame alignment parameters including, but not limited to, x, y, z, $\theta_x$, $\theta_y$, and $\theta_z$, where, x, y, z, are translations in the three coordinate axis and $\theta_x$, $\theta_y$, and $\theta_z$ are rotations about those axis. In various aspects, the FIRMM method further includes calculating total frame displacement using the multiple frame alignment parameters. For example, with a MRI scan of the human head, calculating head realignment parameters across frames, starting with the second frame generates a multiple dimensional (e.g., six) time-series of head motion. The head motion may be converted to a scalar quantity, for example, according to the equation:

$$\text{Displacement}_i = |\Delta d_{ix}| + |\Delta d_{iy}| + |\Delta d_{iz}| + |\Delta \alpha_i| + |\Delta \beta_i| + |\Delta \gamma_i| \qquad \text{Eqn. (1)}$$

where $\Delta d_{ix} = d_{(i-1)x} - d_{ix}$, $\Delta d_{iy} = d_{(i-1)y} - d_{iy}$, $\Delta d_{iz} = d_{(i-1)z} - d_{iz}$, and so forth.

In various aspects, in the non-limiting example of moni- toring a patient's head, rotational displacements may be converted from degrees to millimeters by computing dis- placement on the surface of a sphere, for example a sphere of radius 50 mm, which is approximately the mean distance from the cerebral cortex to the center of the head for a healthy young adult. By realigning each data frame to the reference image, FD may be calculated by subtracting $\text{Displacement}_{i-1}$ (corresponding to the previous frame) from $\text{Displacement}_i$ (corresponding to the current frame).

In various aspects, the FIRMM method further includes predicting whether there will be at least n number of usable frames at the end of a MRI scan. Because each data frame is realigned to the reference image, frame displacement (FD) can be calculated by subtracting $\text{Displacement}_{i-1}$ (corre- sponding to the previous frame) from $\text{Displacement}_i$ (cor- responding to the current frame). In various aspects, pre- dicting the number of usable frames includes applying a linear model (y=mx+b), where y is the predicted number of good frames at the end of the scan, x is the consecutive frame count, and m and b are estimated for each subject in real time. In one aspect, each frame may be labeled as usable if the relative object displacement of that frame is less than a given threshold (e.g., in mm), using the object's position in a previous frame as a reference. One non-limiting example of a cutoff threshold for usable data frames is 0.2, however the scan operator can edit a settings file associated with a FIRMM software suite in one aspect to select a different threshold as desired. In various aspects, usable frames may be determined relative to a pre-assigned cutoff value of total FD, including, but not limited to, less than about 5 mm, less than about 4 mm, less than about 3 mm, or less than about 2 mm total displacement. Alternative alignment algorithms can also be utilized in various other aspects. In various aspects, one or more EPI image regis- tration methods for calculating FD can be used, including, but not limited to, Functional MRI of the Brain Software Library (FSL), Analysis of Functional Neuro Images (AFNI), and Statistical Parametric Mapping (SPM).

In some aspects, motion monitoring information may be provided to the operator and/or the subject undergoing the MRI scan. In one aspect, a visual display of parameters for the scan may be displayed to a user. In various other aspects, at the end of each scan a summary of counts for that scan may be displayed in a list that tabulates the summary head motion data for each scan separately and/or for the sum of all the data acquired thus far in the active scanning session. In certain aspects, predictions may be provided about how much longer a given subject will likely have to be scanned until the pre-set time-to-criterion (minutes of low-movement FD data) has been acquired. For example, a graph of the actual amount of time (e.g., in min and s or percentages) elapsed to scan 'high-quality' frames toward a preset criterion amount of time may be provided. Such information may be provided in the form of a visual display, an auditory signal, or any other known means of providing information without limitation.

In various aspects, FD may be provided to the operator in real time, such that each time a new frame/scan/volume is acquired, a new data-point is added to a FD-vs-frame #graph (see FIG. 11, for example). As implemented in the Examples below, the FIRMM method may generate a display that includes traces of FD in real-time using a GUI. In addition, the FIRMM method may continuously generate updated summary counts representative of the number of 'high-quality' frames already acquired (e.g. given a specific cutoff preset, such as >0.2, >0.3 and/or >0.4) in table format and/or as a color-coded bar graph. At the end of a data acquisition run, the final summary counts for that run are displayed in a list that tabulates the summary head motion data for each run conducted during that scanning session. Furthermore, in certain aspects, predictions for the number of usable data frames that will be available at the end of the run may be provided, as well as the amount of time (e.g., in min and s) of additional scanning predicted to achieve a preset criterion number of usable frames.

In some aspects, the FIRMM method provides for the selection and deselection of specific individual scans for inclusion in the actual and predicted amount of low-movement data.

In various aspects, the FIRMM method further provides for the display of a parameter DVARS as an additional EPI data quality metric. DVARS, as used herein refers to the RMS of the derivatives of the time courses of every voxel of an MRI image. Without being limited to any particular theory, DVARS quantifies volume-to-volume signal changes, and consequently is thought to capture large deviations attributable to phenomena that impact the imaged body part on a global scale including, but not limited to, motion of a body part such as head motion. By way of non-limiting example, DVARS measures how much the whole brain signal intensity varies from each data frame to the next, independent of the source of signal change. DVARS traces are very sensitive to frame-to-frame head motion, and due to the observation of signal losses in echo plane imaging (EPI) in association with abrupt head displacement, DVARS in principle may also detect EPI signal aberrancies from sources other than head motion.

In one aspect, DVARS is computed according to the formula:

$$DVARS(\Delta I_i)_t = \sqrt{\langle [\Delta I_i(\vec{x})]^2 \rangle} = \sqrt{\langle [I_i(\vec{x}) - I_{i-1}(\vec{x})]^2 \rangle}$$

where $I_i(\vec{x})$ represents image intensity at locus $\vec{x}$ on frame i and angle brackets denote a spatial average over the whole brain or other imaged body part.

In various aspects, the FIRMM method generates a sensory feedback display to be communicated to the subject undergoing the MRI scan via a suitable feedback device. Any sensory feedback display may be provided by the FIRMM method via the feedback device including, but not limited to, a visual feedback display, an auditory feedback display, or any other suitable sensory feedback display to any known sensory modality of the subject in the MRI scanner without limitation. Non-limiting examples of suitable sensory feedback devices include a monitor visible to the subject within the MRI scanner via a mirror or other optical element for communication of a visual feedback display, a projector for communication of a visual feedback display via a screen visible to the subject within the MRI scanner, a loud speaker or headphones for communication of an auditory feedback display, or any other suitable sensory feedback device without limitation.

FIG. 31 is a flow chart illustrating a method 3100 for providing a sensory feedback to the operator of the MRI system and/or the patient within the MRI scanner of the MRI system during data acquisition in one aspect. In this aspect, the method 3100 includes calculating a data quality metric at 3102 based on one or more components of movement determined for the patient in the MRI device during scanning as described previously. Any data quality metric may be calculated at 3102 without limitation as described herein including, but not limited to, any one or more of the displacement components as described above, an overall frame displacement as described above, other data quality metrics including DVARS as described above, and any combination thereof.

Referring again to FIG. 31, the method 3100 may further include generating a visual display in real time to an operator of the MRI system at 3104 based on at least a portion of the data quality metric calculated at 3102. Non-limiting examples of suitable visual feedback displays include at least a portion of a GUI such as the GUI illustrated in FIG. 1. In various aspects, described in additional detail below. the visual feedback display for the operator of the MRI system may include visual elements including, but not limited to, one or more graphs displaying the data quality metrics for all frames received in the scan, tables of summary statistics regarding the quality of the current and previous scans, graphical or tabular elements communicating the cumulative number of useable frames obtained in the current scan, tabular or graphical elements communicating the amount of time remaining in the current scan and/or the predicted amount of time remaining in the current scan to obtain a predetermined number of useable scans, as described herein, and any combination thereof. In various aspects, the elements of the visual feedback display may be updated at any preselected rate up to a real-time rate of updating each display as each relevant quantity is calculated, the elements of the visual feedback display may be updated in response to a request from the operator of the MRI system, and the elements of the visual feedback display may dynamically update in response to at least one of a plurality of factors including, but not limited to, significant increases in the monitored motion of the subject between frames, cumulative motion, or any other suitable criteria.

Referring again to FIG. 31, the method 3100 may further include generating a sensory feedback display at 3106 for the patient in the scanner during acquisition of MRI data. As described in additional detail below, the sensory feedback display generated at 3104 may be updated at a wide variety of refresh rates ranging from a single update at the end of scanning to continuously updating in real time, based on at least one of a plurality of factors including, but not limited to the patient's age and condition.

In various aspects, the method 3100 may further include determining the total movement of the patient at 3108 between the previous frame and the current frame in response to the sensory feedback display generated at 3106. In one aspect, the method 3100 further includes evaluating at least one of a plurality of factors to determine whether the current MRI scan should be terminated at 3110. In various aspects, the scan may be terminated in accordance with at least one of a plurality of termination criteria including, but not limited to, one or more movements of an unacceptably high magnitude, and unacceptably high number of relatively low magnitude movements, a determination that a suitable number of useable frames were obtained, a prediction that a suitable number of useable frames cannot be obtained in the time remaining in the scan, a prediction that a suitable number of useable frames cannot be obtained within a reasonable cumulative scan time, and any combination thereof. If it is determined at 3110 to continue the scan, the method 3100 may communicate at least one feedback signal 3112 to be used in part to calculate the data quality metric at 3102 to start another iteration of the method 3100 for a subsequent frame.

In one aspect, the FIRMM method may provide a visual feedback display to the subject undergoing the MRI scan. In this aspect, a characteristic of the visual feedback display may change to communicate the occurrence of movement of the subject based on the detected motion of the subject obtained using the FIRMM method as described above. Any characteristic of one or more elements of a visual feedback display may be selected to vary in order to communicate the occurrence of movement including, but not limited to, a size, a shape, a color, a texture, a brightness, a focus, a position, a blinking rate, any other suitable characteristic of a visual element, and any combination thereof.

In another aspect, the FIRMM method may provide an auditory feedback display to the subject undergoing the MRI scan. In this aspect, a characteristic of the auditory feedback display may change to communicate the occurrence of movement of the subject based on the detected motion of the subject obtained using the FIRMM method as described above. Any characteristic of one or more elements of an auditory visual feedback display may be selected to vary in order to communicate the occurrence of movement including, but not limited to, a pause in the playback of a musical selection, a resumption of playback of a musical selection, a verbal cue, a volume of a tone, a pitch of a tone, a duration of each tone in a series, a repeat rate of a series of tones, a steadiness or waver in a pitch or volume of a tone, any other suitable characteristic of an auditory feedback, and any combination thereof.

In various aspects, a characteristic of a sensory feedback display may vary based on a degree or magnitude of detected movement by the subject in the MRI scanner. In one aspect, the characteristic of the sensory feedback display may vary continuously in proportion to the degree of detected movement of the subject. In another aspect, the characteristic of the sensory feedback display may change within a discrete set of characteristics, in which each characteristic in the discrete set is configured to communicate the occurrence of one level of movement including, but not limited to, no movement, low movement, a medium or intermediate level of movement, and a high degree of movement.

In various other aspects, the sensory feedback display may vary in response to changes in a single component of movement such as a translation in a single x, y, or z direction or a rotation about a single x, y, or z direction, the sensory feedback display may vary in response to changes in a combination of two or more components of movement, or the sensory feedback display may vary in response to an overall movement metric such as frame displacement described above. In one aspect, a single characteristic of the sensory feedback display is varied to communicate the occurrence of movement to the subject. In another aspect, two or more characteristics of the sensory feedback are varied independently to communicate the occurrence of movement to the subject, in which each characteristic varies based on a subset of the components of movement. By way of non-limiting example, a sensory feedback display may include a first characteristic that varies based on movement of the subject in the x-direction, and a second characteristic that varies independently based on combined movement of the subject in the y-direction and z-direction.

In various aspects, the frequency at which the characteristics of a sensory feedback display are updated may range from a single feedback display at the end of a scan to communicate whether or not sufficiently low movement was maintained during the scan to a frequency commensurate with the real-time frequency at which movement is monitored by the FIRMM method, and at any intermediate frequency without limitation. In various aspects, the frequency at which the characteristics of a sensory feedback display are updated may be selected based on at least one characteristic of the subject to be imaged in the MRI scanner including but not limited to, age of the subject, a condition of the subject such as attention deficit disorder or a learning disability, and any other relevant characteristic of the subject without limitation. In various aspects, the FIRMM method provides for feedback based on a motion value from a single frame or a combination of motion values across multiple frames. In various other aspects, the FIRMM method provides for real-time feedback and time delayed feedback. By way of on-limiting example, if a high update frequency is used for a sensory feedback display for a very young child, the display may encourage the child to increase movement within the MRI scanner as a way of providing a more entertaining and dynamic sensory feedback experience. In various aspects, the frequency at which the characteristics of a sensory feedback display are updated may be specified to be a constant update rate throughout MRI scanning, or the update rate may dynamically vary based on an instantaneous and/or cumulative assessment of the motion of the subject.

By way of non-limiting example, a subject undergoing the MRI scan may be instructed to view a fixation crosshair (e.g., a target). In this example, the crosshair may be color-coded based on the subject's detected movement (e.g., head motion), and the subject may be instructed to maintain the crosshair at a certain color (e.g., a first color) by remaining still during the scan. As a consequence of detected changes in the subject's movement, the crosshair may change to a second color (e.g., to represent medium movement) or a third color (e.g., to represent high movement), thereby enabling the subject to monitor and adjust his or her own movement during the scan. In another non-limiting example, a subject undergoing an MRI scan may be instructed to watch a movie clip. Based on the subject's level of movement (low movement, medium movement, high movement), a visual impediment on the movie clip may prevent the subject from viewing parts of the movie clip. For example, the subject may be instructed to remain still during the scan in order to watch an unobstructed view of the movie clip. Based on the subject's level of movement, the movie clip may be obstructed by a rectangular block of a certain size (e.g., a small yellow-colored rectangle for medium movement, and a large red-colored rectangular for high movement). Thus, the subject is able to monitor and adjust his or her own movement during the scan based on the real-time visual feedback.

In other aspects, the FIRMM method further provides for fixed and adaptive feedback conditions for the real-time visual displays described above. In one aspect, for fixed feedback conditions, thresholds for low, medium, and high motions may be held constant for the duration of the MRI scan. In another aspect, for adaptive feedback conditions, thresholds for low, medium, and high motions may change and be replaced with stricter (e.g., lower) threshold values during the duration of the MRI scan. With adaptive feedback conditions, the MRI scanner may adapt to the subject's ability to remain still, and, for example, increase the difficulty level of keeping the crosshair a first color or the movie clip visibly unobstructed.

In some aspects, changes in MRI acquisition procedures including, but not limited to, multiband imaging, enable improved temporal and spatial resolution relative to previous MRI acquisition procedures. However, the improved temporal and spatial resolution may be accompanied by artifacts in motion estimates from post-acquisition frame alignment procedures, thought to be caused primarily by chest motion during respiration. Without being limited to any particular theory, chest motion associated with respiration changes the static magnetic field (B0) during MRI data acquisition, and such 'tricks' any frame-to-frame alignment procedure used in real-time motion monitoring into correcting a 'head movement' even in the absence of actual head movement. In one aspect, the FIRMM method incorporates an optional band-stop (or notch) filter to remove respiration-related artifacts from motion estimates, thereby enhancing the accuracy of real-time representations of motion.

In various aspects, the FIRMM method applies a notch filter (e.g., band-stop filter) to motion measurements to remove artifacts from motion estimates caused by a subject's breathing. More specifically, as described in Example 4 below, a subject's breathing contaminates movement estimates in fMRI, and thereby distorts the quality of MRI data obtained. As described in Example 5 below, some aspects utilize a general notch filter to capture a large portion of a sample population's respiration peak with respect to power. In other aspects, a subject-specific filter based on filter parameters specific to a subject's respiratory belt data may be used.

In an aspect, the band-stop (e.g., notch filter) may be implemented to remove the spurious signal in the motion estimates that correspond to the aliased respiration rate. Conceptually, this filter removes the undesired frequency components while leaving the other components unaffected. The notch filter has two design parameters: (a) the central cutoff frequency and (b) the bandwidth or range of frequencies that will be eliminated. To establish the parameters for the central cutoff frequency and the bandwidth, a distribution of respiration rates obtained from various subjects of MRI during data acquisition may be analyzed, and a median of the distribution may be used as the cutoff frequency, and the quartiles 2 and 3 of the distribution may be used to determine bandwidths of the notch filter in various aspects. Subsequent to establishing these parameters, an IIR notch filter function may be used to design the notch filter. It is to be noted that for a given sampling rate (1/TR), the respiratory rates may not be aliased. In other cases, when the combination of TR and respiration rate leads to aliasing, the aliased respiration rate should be used instead.

In one aspect, the designed filter is a difference equation. When applied to a sequence representing a motion estimate, this difference equation recursively weights the two previous samples to provide an instantaneous filtered signal. This procedure starts with the third sample, weights the two previous points, and continues until the last time-point is filtered. One of the trade-offs of this type of implementation is that the filtered signal will have a phase delay with respect to the original signal. In one aspect, this phase delay may be compensated for by applying the filter twice, once forward and the second time backwards such that the opposite phase lags cancel out each other. To do this, once the filter is applied to the entire sequence, the same filter (difference equation) is reapplied backwards, with the last time-point of the forward-filtered sequence used as the first point for the backward application of the filter, and the recursive process continues until the first time-point of the forward-filtered sequence is filtered. In various aspects, the designed notch filters (general and subject-specific) may be applied to a sequence of motion estimates post-processing to improve data quality.

FIG. 32 is a flow chart illustrating a method 3200 for removing artifacts associated with respiration from the detected motion data using an Nth order filter. In one aspect, the method 3200 includes receiving 2N+1 frames from the MRI system at 3202 that are used to create the Nth order filter. In addition to the 2N+1 frames, the method 3200 further includes creating the Nth order filter based on minimum and maximum respiratory frequencies at 3204 in addition to the 2N+1 frames. In various aspects, described in additional detail herein, the subject's respiratory rate may be obtained using a variety of devices and methods including but not limited to, a respiratory monitor belt fitted to the subject, extracting respiratory frequency information from MRI signals obtained from the patient in the MRI scanner, and any other suitable method without limitation.

Referring again to FIG. 32, the method 3200 may further include calculating a motion of a body part of the patient using the methods described herein at 3206. The method further includes applying the Nth order filter created at 3202 to the current frame set in a forward and reverse direction with respect to data acquisition time at 3208. Without being limited to any particular theory, the Nth order filter in both directions eliminates a phase lag from the filtered data. Using the filtered motion estimates calculated at 3210, a data quality metric including, but not limited to framewise displacement is calculated at 3210. If additional frames are obtained at 3212, the method may replace the earliest frame in the 2N+1 frames received previously at 3202 with the frame received at 3212 to initiate a subsequent iteration of the method 3200.

In various aspects, the designed filter can also be applied in real time, since each instantaneous estimate of motion can be filtered out by weighting previous estimates following the notch filter's difference equation. As mentioned before, however, this approach leads to a phase lag. In one aspect, the filter is run in pseudo-real time to minimize the phase lag. In this aspect, once 5 samples are obtained, the filter could be applied twice and the best estimate would be the value corresponding to the third sample. This delayed signal will not have a phase delay. As each new sample is obtained, the filter can be applied twice to the entire sequence and the process can be repeated. Each time a new sample is measured, the filtered sequence will converge closer to the optimal output obtained when the filter is applied twice to the entire sequence. At the final frame of a given run, the filtered sequence is then identical to the filtered sequence obtained during post processing. Thus, the designed notch filters may be used in real-time to improve the accuracy of real-time estimates of motion using the FIRMM head motion prediction method described above.

In various aspects, adaptive filtering methods, including least squares adaptive filtering, may be applied in real time to identify and remove signal content associated with undesired frequencies from subject movement data, such as cardiac and/or respiratory frequencies, from measured subject movement data including, but not limited to, framewise displacement data, without concurrently introducing a phase lag to these data. In one aspect, a real-time adaptive filter may be used to remove respiratory-related artifacts from the MRI data.

In one aspect, illustrated in FIG. 34, an adaptive filtering method makes use of an unfiltered signal 3402 including, but not limited to, framewise displacement (FD) data derived from images obtained from the subject in the MRI scanner using the FIRMM method described above, as well as a best estimate of the noise signal 3404 to be eliminated using the adaptive filter 3406. The adaptive filter method 3400 minimizes in real time by gradient descent the contribution of the undesired signal into the measured signal, providing an optimal filtered sequence 3408. Non-limiting examples of suitable noise signals 3404 to be input to the adaptive filter 3406 include real-time measurements of the respiration rate of the subject in the MRI scanner, the sum of multiple sinusoidal signals at different phases with frequencies corresponding to the respiration rate of the subject, and any other suitable estimate of the subject's respiration rate. In one aspect, the respiration rate of the participant could be measured while the T1w or a previous sequence is acquired and used as the signal noise input 3404.

Referring again to FIG. 34, in one aspect the adaptive filter method 3400 includes receiving a first estimation of head movement 3402 in each direction (i.e., x, y, z, $\theta_x$, $\theta_y$, $\theta_z$) as determined using the FIRMM method described above. This first estimation of head movement 3402 includes both the real head movement(s) and the undesired artifact ($n_0$). Importantly, these two signals s and $n_0$ assumed to be independent and uncorrelated. In this method 3400, an additional input 3404 consisting of a best estimation of the undesired artifact ($n_1 = \hat{n}_0$) is received. If the undesired artifact no corresponds to respiration rate, this signal 3404 may be provided as a real time measurement of the respiration rate. In another aspect, if real time measurements of respiration are not available, a sinusoidal signal comprising a sum of a plurality of sinusoidal signals may be generated, in which the most likely respiration rate corresponds to the subject in the scanner. This error signal 3404 is filtered out by the adaptive filter 3406 to generate an optimized estimate of the error signal 3410 (y(T)). In this aspect, the goal of the adaptive filter 3406 is to maximize the correlation of the optimized estimate of the error signal 3410 (y(T)) and the measured estimation of head movement 3402 (d(T)). It is to be noted that, when the first frame is used, the adaptive filter 3406 has no effect on the signal 3404 (($\vec{n}_0$)). Also in this aspect, the optimized estimate of the error signal 3410 (y(T)) is subtracted from the measured estimation of head movement 3402 (d(T)) to calculate the error signal 3408 (i.e. e(T)=s+$n_0$−y(T)). This error 3408 is used as a feedback signal 3412 to modify the parameters of the adaptive filter 3406 to make the signal 3410 (y(t)) as correlated as possible to the measurement 3402 (d(T)). As the real head movement(s) and the real artifact ($n_0$) are uncorrelated, maximizing the correlation between $\hat{n}_0$ and d(T) is driven by the match between $n_0$ and $\hat{n}_0$. Hence, subtracting those signals (3402 and 3410) removes the undesired artifact. In one aspect, an adaptive filter method 3400 may be implemented using well-established methods in which the parameters of a second order difference equation are optimized to maximize the estimation of the undesired artifact.

In various aspects, to examine the effects of the filter quantitatively, a quality control method may be used, as illustrated in FIGS. 19A, 19B, 19C, and 19D, to quantitatively measure improved motion estimates after filtering. This approach does not involve censoring, and can be applied to any dataset and any data quality metric. As shown in FIGS. 19A-19D and FIGS. 30A-30C, the quality control method includes reordering a subject's volumes by decreasing quality irrespective of temporal order, as illustrated in FIG. 19A. The method further includes passing a sliding window through the quality-ordered data calculating correlations in different parts of the data, as illustrated in FIG. 19B. In addition, the method includes comparing the correlation matrix in the first window or first few windows to the matrix obtained in the other windows, as illustrated in FIG. 19C. After having established that motion artifacts have reduced distance dependence, the disclosed approach was used instead of $\Delta r$ of short-range connections, as originally shown for multiband data. The method in this aspect further includes establishing a null distribution of the outcome measure by repeating the steps described above while permuting the data quality metric values assigned to volumes (e.g., FD value for a given frame), using the null distribution to determine the significance of the quality-ordered outcome in each sliding window, and mapping the determined significance back to each of the data quality metric values contained in the sliding windows, as illustrated in FIG. 19D.

FIG. 33 is a flow chart illustrating a method 3300 of using an adaptive filter developed as illustrated in FIG. 34. Referring to FIG. 33, the method includes receiving a current frame from the MRI system at 3302, and calculating a motion of a body part between the reference image and the current frame at 3304. The method 3300 further includes removing undesired signal variations associated with respiration from the motion of the subject's body part calculated at 3304 using the adaptive filter at 3306, where the adaptive filter may be determined in according with the method 3400 summarized in FIG. 34. Using the filtered motion data calculated at 3304 and 3306, a data quality metric including, but not limited to framewise displacement may be calculated to 3308. The method 3300 may further include determining if an additional frame is obtained at 3310 and initiating another iteration of the method 3300 as needed.

FIG. 8 illustrates one non-limiting example FIRMM method 800 for processing a set of MRI frames to align the frames to a reference image in a set to compensate for a subjects' movement, in one aspect. The FIRMM method 800 includes receiving data at 802 from a magnetic resonance imaging system in the form of an MRI frame or image. The MRI frame may be received by a computing device from a magnetic resonance imaging system via a network or from a storage medium coupled to or in communication with the computing device.

Referring again to FIG. 8, the FIRMM method 800 also includes aligning the frame to the reference image at 804. Each frame may be aligned to the reference image through a series of rigid body transforms, $T_i$, where i indexes the spatial registration of frame i to a reference of frame1, starting with the second frame. Each transform is calculated by minimizing the registration error to an absolute minimum or below a selected cutoff:

$$\varepsilon_i = \left\langle \left( sI_i\left(T(\vec{x})\right) - I_1(\vec{x}) \right)^2 \right\rangle, \qquad \text{Eqn. (2)}$$

where $I(\vec{x})$ is the image intensity at locus $\vec{x}$ and s is a scalar factor that compensates for fluctuations in mean signal intensity, spatially averaged over the whole brain (angle brackets). In certain aspects, the frames may be realigned using 4dfp cross_realign3d_4dfp algorithm (see Smyser, C. D. et al. 2010, *Cerebral cortex* 20, 2852-2862, (2010)) which is specifically incorporated herein by reference). Alternative alignment algorithms can also be utilized to align the frames.

The FIRMM method 800 also includes calculating the relative motion of a body part between the frame and the preceding frame. The relative motion of a body part (e.g., head motion) may be calculated from six frame alignment parameters, x, y, z, $\theta_x$, $\theta_y$, and $\theta_z$, where x, y, z, are translations in the three coordinate axis and $\theta_x$, $\theta_y$, and $\theta_z$, are rotations about those axis.

The FIRMM method 800 also includes calculating the total frame displacement at 808 to generate multiple displacement vectors of head motion. By way of non-limiting example, total frame displacement may be calculated by adding the absolute displacement of the body part (e.g., head) in six directions, thereby treating the body part as a rigid body. In this non-limiting example, the head motion of the $i^{th}$ frame may be converted to a scalar quantity using the formula:

$$\text{Displacement}_i = |\Delta d_{ix}| + |\Delta d_{iy}| + |\Delta d_{iz}| + |\Delta \alpha_i| + |\Delta \beta_i| + |\Delta \gamma_i|; \quad \text{Eqn. (3)}$$

where $\Delta d_{ix} = d_{(i-1)x} - d_{ix}$; $\Delta d_{iy} = d_{(i-1)y} - d_{iy}$; $\Delta d_{iz} = d_{(i-1)z} - d_{iz}$; and so forth.

Rotational displacements $|\Delta \alpha_i|$, $|\Delta \beta_i|$, and $|\Delta \gamma_i|$ may be converted from degrees to millimeters by computing displacement on the surface of a 3D volume representative of the body part being imaged. By way of non-limiting example, if the head is imaged, the 3D volume selected to calculate displacement may be a sphere. Since each data frame is realigned to the reference image, FD may be calculated by subtracting $\text{Displacement}_{i-1}$ (for the previous frame) from $\text{Displacement}_i$ (for the current frame).

In some aspects, the FIRMM method 800 may further include excluding frames with a cutoff above a pre-identified threshold of total frame displacement at 810. Upon completion, the FIRMM method 800 returns to the start for each subsequent frame in the MRI scan.

In various aspects, the method 800 may be implemented by a system that includes an MRI system and one or more processors or computing devices. In various aspects, one or more operations described herein may be implemented by one or more processors having physical circuitry programmed to perform the operations. In various other aspects, one or more steps of the FIRMM method 800 may automatically be performed by one or more processors or computing devices. In various additional aspects, the various acts illustrated in FIG. 8 may be performed in the illustrated sequence, in other sequences, in parallel, or in some cases, may be omitted.

Computing System

In some aspects, the above described FIRMM methods and processes may be implemented using a computing system, including one or more computers. In particular, the FIRMM methods and processes described herein, e.g., methods described herein, may be implemented as a computer application, computer service, computer API, computer library, and/or other computer program product.

FIG. 9 depicts a simplified block diagram of a system 900 for implementing the FIRMM method described herein including, but not limited to, the method 800 shown illustrated in FIG. 8. Referring again to FIG. 9, a FIRMM computing device 904 may be configured to (i) receive an MRI data frame from a magnetic resonance imaging (MRI) system 902; (ii) align the received frame to a reference image received from MRI system 902 or retrieved from an anatomical atlas, or any other suitable reference image as described herein; (iii) calculate motion of a body part between the received frame and the reference image; (iv) calculate a data quality metric based at least in part on the calculated motion of the body part between the received frame and the reference image; (v) classify frames based on each frame's data quality metric based on a pre-identified data quality metric threshold; (vi) transmit feedback in real time to an operator via an operator computing device 910; and (vii) display sensory feedback to a subject (e.g., patient) undergoing an MRI scan via a patient computing device 912.

The system 900 further includes a database server 906 communicatively coupled to a database 908 that stores data. In one aspect, the database 908 may include head motion parameters, framewise displacement (FD) values associated with each data frame, and data associated with completed scan sessions (e.g., saved data frames). Additionally or alternatively, the database 908 may also include data associated with real-time visual displays and feedback conditions, such as movie clips and color-coded crosshairs displayed to a subject undergoing the MRI and preset thresholds for the visual displays (e.g., thresholds for no movement, medium movement, and high movement). In the exemplary aspect, the database 908 may be stored remotely from the FIRMM computing device 904. In some aspects, the database 908 may be decentralized.

In various aspects, the FIRMM computing device 904 may be communicatively coupled with, or is part of a computer network associated with the MRI system 902. The MRI system 902 is configured to acquire MRI images. In the exemplary aspect, The FIRMM computing device 904 receives MRI data frames from at least one MRI scanner of the MRI system 902.

The FIRMM computing device 904 may also be associated with one or more operator computing devices 910. In various aspects, operator computing devices 910 are computers that enable an operator to control the scanner. The operator computing device 910 enables the operator to view the received real-time and post-hoc visual feedback about a subject's body movements. More specifically, operator computing devices 910 may be communicatively coupled to the Internet through many interfaces including, but not limited to, at least one of a network, such as the Internet, a local area network (LAN), a wide area network (WAN), or an integrated services digital network (ISDN), a digital-up-connection, a digital subscriber line (DSL), a cellular phone connection, and a cable modem. Operator computing device 910 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices.

In the exemplary aspect, FIRMM computing device 904 transmits real-time feedback to an operator via an operator computing device 910. In further aspects, the operator computing device 910 may be or include a display device (e.g., a cathode ray tube (CRT), liquid crystal display (LCD), light emitting diode (LED) display, "electronic ink" display), or other electronic display configured to present a graphical user interface (e.g., a web browser and/or a client application) to the operator. In some aspects, the operator computing device 910 may include an input device for receiving input from the operator. The operator may use the input device during the MRI scan to, without limitation, respond to the data received from the FIRMM computing device 904 by, for example, selecting and/or deleting MRI data frames, and halting the MRI scan. In other aspects, operator computing device 910 may receive an input from the operator (e.g., by a touch screen, actuation of an icon, manipulation of an input device such as a joystick or knob, etc.). In these aspects, the operator computing device 910 may communicate (actively and/or passively) the input to one or more processors of the FIRMM computing device 904. In certain aspects, the operator computing device 910 may display MRI scan reports generated by FIRMM computing device 904 at the end of a scan session.

The FIRMM computing device 904 may be communicatively coupled with one or more patient computing devices 912 associated with a subject (e.g., a patient) undergoing the MRI scan. More specifically, the patient computing device 912 may be communicatively coupled to the Internet through many interfaces including, but not limited to, at least one of a network, such as the Internet, a local area network (LAN), a wide area network (WAN), or an integrated services digital network (ISDN), a digital-up-connection, a digital subscriber line (DSL), a cellular phone connection, and a cable modem. The patient computing device 912 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices. In the exemplary aspect, the patient computing device 912 receives real-time visual feedback from FIRMM computing device 904. In the exemplary aspect, the patient computing device 912 is a display device (e.g., a cathode ray tube (CRT), liquid crystal display (LCD), light emitting diode (LED) display, or "electronic ink" display). The patient computing device 912 may display stimulus conditions, such as movie clips and color-coded crosshairs to engage the subject, and provide real-time feedback received from the FIRMM computing device 904 to the subject undergoing the MRI scan. In some aspects, the operator computing device 910 and/or the patient computing device 912 are part of the MRI system 902.

FIG. 10 schematically shows a computing device 1000 in another aspect configured to perform one or more of the methods and processes described herein. The computing device 1000 may be similar to the FIRMM computing device 904 illustrated in FIG. 9. Referring again to FIG. 10, computing device 1000 may be operatively coupled to, in communication with, or included in an MRI system, such as the MRI system 902 shown in FIG. 9.

It is to be understood that any computer architecture may be used without limitation without departing from the scope of this disclosure. In different aspects, the computing device 1000 may take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

In an aspect, the computing device 1000 includes a logic subsystem 1002 and a data-holding subsystem 1004. The computing device 1000 may optionally include a display subsystem 1006, a communication subsystem 1008, an imaging subsystem 1010, and/or other additional components not shown in FIG. 10. The computing device 1000 may also optionally include user input devices such as manually actuated buttons, switches, keyboards, mice, game controllers, cameras, microphones, and/or touch screens, for example.

The logic subsystem 1002 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1004 may include one or more physical, non-transitory, devices configured to hold data and/or instructions executable by the logic subsystem to implement the herein described methods and processes. When such methods and processes are implemented, the state of data-holding subsystem 1404 may be transformed (e.g., to hold different data).

Data-holding subsystem 1004 may include removable media and/or built-in devices. Data-holding subsystem 1004 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1404 may include devices with one or more of the following characteristics: volatile, nonvolatile, dynamic, static, read/write, read-only, random access, sequential access, location addressable, file addressable, and content addressable. In some aspects, logic subsystem 1002 and data-holding subsystem 1004 may be integrated into one or more common devices, such as an application specific integrated circuit or a system on a chip.

FIG. 10 also shows an aspect of the data-holding subsystem in the form of a removable computer-readable storage media 1012, which may be used to store and/or transfer data and/or instructions executable to implement the herein described methods and processes. Removable computer-readable storage media 1012 may take the form of CDs, DVDs, HD-DVDs, Blu-Ray Discs, EEPROMs, flash memory cards, USB storage devices, and/or floppy disks, among others.

When included, display subsystem 1006 may be used to present a visual representation of data held by data-holding subsystem 1004. As the herein described methods and processes change the data held by the data-holding subsystem, and thus transform the state of the data-holding subsystem 1004. For example, the state of display subsystem 1006 may likewise be transformed to visually represent changes in the underlying data. Display subsystem 1006 may include one or more display devices utilizing virtually any type of technology. Such display devices may be combined with logic subsystem 1002 and/or data-holding subsystem 1004 in a shared enclosure, or such display devices may be peripheral display devices.

In an aspect, communication subsystem 1008 may be configured to communicatively couple computing device 1000 with one or more other computing devices. Communication subsystem 1008 may include wired and/or wireless communication devices compatible with one or more different communication protocols. As non-limiting examples, the communication subsystem 1008 may be configured for communication via a wireless telephone network, a wireless local area network, a wired local area network, a wireless wide area network, a wired wide area network, etc. In some aspects, the communication subsystem may enable computing device 1000 to send and/or receive messages to and/or from other devices via a network such as the Internet.

In one aspect, imaging subsystem 1010 may be used to acquire and/or process any suitable image data from various sensors or imaging devices in communication with computing device 1000. For example, imaging subsystem 1010 may be configured to acquire MRI image data, as part of an MRI system, e.g., MRI system 902 described above. Imaging subsystem 1010 may be combined with logic subsystem 1002 and/or data-holding subsystem 1004 in a shared enclosure, or such imaging subsystems may comprise periphery imaging devices. Data received from the imaging subsystem 1010 may be held by data-holding subsystem 1004 and/or removable computer-readable storage media 1012, for example.

In various aspects, the FIRMM method disclosed herein may be implemented in the form of one or more of at least several software packages, each with a specific purpose, to make installation and usage easier and more reliable. Any known type of software package executable on any known operating system may be used to implement the FIRMM methods disclosed herein without limitation.

By way of non-limiting example, a Docker-capable Linux system may be used to enable the FIRMM method described herein. In this example, the FIRMM software package may be launched with a shell script tailored to use a pre-built Docker image. The components used in the FIRMM implementation in this example include a compiled MATLAB (R2016b) binary backend which only requires an included MATLAB compiler runtime to run, shell scripts for image processing, a Docker image containing image processing software dependencies, and a Django web application frontend. The compiled MATLAB binary backend monitors an incoming folder waiting for a new subfolder that has the current date and contains images created within the last few minutes. The backend does shell script image processing only on new functional images. The required image processing software in this example is installed and configured already inside the Docker image. In this example, the results are visually displayed in the Django web application frontend as plots and tables via a web browser.

In this example, as soon as each frame/volume of EPI (echo planar imaging) data is acquired and reconstructed into a Digital Imaging and Communications in Medicine (DICOM) format, it is transferred to a pre-designated folder that the FIRMM software monitors for new images. Using a Siemens scanner, rapid DICOM transfer is achieved by selecting the 'send IMA' option in the ideacmdtool utility.

The FIRMM software reads the DICOM headers, and uses the header information to enter each DICOM sequentially into a job queuing system. DICOMs are processed in the temporal order they were acquired. The FIRMM software converts the DICOMs into nifti and then 4dfp format prior to any further processing. FIRMM realigns EPI data using the 4dfp cross_realign3d_4dfp algorithm (see Smyser, C. D. et al., Cerebral cortex 20, 2852-2862, (2010)). The cross_realign3d_4dfp algorithm run by the FIRMM software is optimized for computational speed, thus frame-to-frame image intensity normalization is disabled and the realigned data are not written out, only the alignment parameters. Alternative alignment algorithms operating on nifti format data can also be utilized. The EPI images do not undergo pre-processing steps typically utilized in offline data analyses. For EPI images with a spatial resolution smaller than 4 mm$^3$, data are down-sampled to 4 mm$^3$ prior to realignment to increase processing speed.

To estimate head realignments, each data frame (volume) of the run is aligned to a reference image through a series of rigid body transforms, $T_i$, where i indexes the spatial registration of frame i to the reference image. Each transform is calculated by minimizing the registration error:

$$\varepsilon_i = \left\langle \left( s I_i \left( T(\vec{x}) \right) - I_1(\vec{x}) \right)^2 \right\rangle,$$

where $I(\vec{x})$ is the image intensity at locus $\vec{x}$ and s is a scalar factor that compensates for fluctuations in mean signal intensity, spatially averaged over the whole brain (angle brackets). Each transform is represented by a combination of rotations and displacements as described by:

$$T_i = \begin{bmatrix} R_i & \dot{d}_i \\ 0 & 1 \end{bmatrix}$$

where $R_i$ represents the 3×3 matrix of rotations and $\dot{d}_i$ represents the 3×1 column vector of displacements. $R_i$ consists of the three elementary rotations at each of the three axes as expressed by:

$$R_i = R_{i\alpha} R_{i\beta} R_{i\gamma}, \text{ where}$$

$$R_{i\alpha} = \begin{bmatrix} 1 & 1 & 0 \\ 0 & \cos \alpha_i & -\sin \alpha_i \\ 0 & \sin \alpha_i & \cos \alpha_i \end{bmatrix}$$

$$R_{i\beta} = \begin{bmatrix} \cos \beta_i & 0 & \sin \beta_i \\ 0 & 1 & 0 \\ -\sin \beta_i & 0 & \cos \beta_i \end{bmatrix}$$

$$R_{i\gamma} = \begin{bmatrix} \cos \gamma_i & -\sin \gamma_i & 0 \\ \sin \gamma_i & \cos \gamma_i & 0 \\ 0 & 0 & 1 \end{bmatrix}.$$

To compute framewise displacement (FD), head realignment parameters are calculated across frames starting with the second frame to generate six displacement vectors of head motion. The head motion is converted to a scalar quantity with the formula: $\text{Displacement}_i = |\Delta d_{ix}| + |\Delta d_{iy}| + |\Delta d_{iz}| + |\Delta \alpha_i| + |\Delta \beta_i| + |\Delta \gamma_i|$, where $\Delta d_{ix} = d_{(i-1)x} - d_{ix}$, $\Delta d_{iy} = d_{(i-1)y} - d_{iy}$, $\Delta d_{iz} = d_{(i-1)z} - d_{iz}$, and so forth.

Rotational displacements are converted from degrees to millimeters by computing displacement on the surface of a sphere of radius 50 mm, which is approximately the mean distance from the cerebral cortex to the center of the head for a healthy young adult. In various aspects, alternative schemes of converting rotational displacements from degrees to millimeters may be used without limitation to account for variations in the patient's size or age, or to adjust for body parts different from the head/brain. Since each data frame was realigned to the reference image, FD was calculated by subtracting Displacement$_{i-1}$ (for the previous frame) from Displacement$_i$ (for the current frame).

To visualize framewise displacement (FD) in real time, the FIRMM software in one aspect may use a graphical user interface (GUI) designed in Django (www.djangoproject.com) and Chart.js (www.chartjs.org) to display FD traces and summary counts of data quality in real time. An example of a representative GUI 1100 is illustrated in FIG. 11. The GUI 100 may continuously display and update a graph 1101 of each frame's FD as a function of scan time. The GUI 100 may also continuously display and update summary counts about the number of 'high-quality' low-movement frames already acquired in a table format 1102 and as a color-coded bar graph 1104. As described above, low-movement frames may be identified as those frames with an FD that falls below an FD cutoff preset. Any one or more suitable FD cutoff presets may be selected without limitation including, but not limited to FD cutoff preset values of 0.2 mm, 0.3 mm and 0.4 mm. At the end of each data acquisition epoch (e.g., scan) the summary counts for that scan are displayed in a list 1106 that tabulates the summary head motion data for each scan separately, and for the sum of all the data acquired thus far in the active scanning session. The GUI may also display predictions 1108 about how much longer a given subject will likely have to be scanned until the preset time-to-criterion (e.g., minutes of low-movement FD data) has been acquired. The GUI may further include a graph of the actual amount of time (in min and s) one has scanned 'high-quality' frames toward a preset criterion amount of time. Users are able to customize the FD cutoffs and data amount criterion via a simple settings file.

In one aspect, the head motion (FD) prediction algorithm for predicting FD is a linear model that updates with each new data frame (y=mx+b), where y is the predicted number of low-movement frames below a certain FD cutoff at the end of the scan or experiment, x is the consecutive frame count, and m and b are estimated for each participant in real time. A given frame is labeled as usable if the relative object displacement is less than a given threshold (in mm), using as reference the object's position in the previous frame.

In various aspects, implementations of the FIRMM software use an MRI scanner configured to rapidly reconstruct and transfer BOLD images. The FIRMM software currently expects an EPI mosaic as provided by Siemens, but may be customized to work with non-mosaic formats associated with other MRI device makers, such as General Electric (GE) and Philips. In one aspect, the FIRMM software may be implemented on a Siemens 3T Tim Trio scanner and/or a Siemens 3T Prisma scanner. In various aspects, the FIRMM software may be configured to enable compatibility with a wide range of sequences and EPI image types. By way of non-limiting examples, for use with Siemens scanners, the FIRMM software may utilize the ideacmdtool SendIMA option with buffering disabled. Alternatively, rapid DICOM forwarding may also be built directly into Siemens sequences to enable communication with the FIRMM software.

In one aspect, the FIRMM software is implemented on a Docker-capable Linux computer networked to a second computer running the scanner operating system, which is typically included with existing MRI scanning systems used in research. The FIRMM software may be self-contained in a Docker image.

In one non-limiting example, the FIRMM software is implemented using a computer running Linux (Ubuntu 14.04 LTS) and the following hardware specifications: CPU=Intel Core i7 4790K 4.0 GHz Quad-core, motherboard=ASUS Z97M-PLUS, memory=16 GB DDR3, hard drive=Samsung 850 EVO 120 GB and graphics=GPU NVIDIA GTX 960.

In one aspect, the FIRMM software saves a temporary processing folder per study using the DICOM header information. In that folder, the FIRMM software saves the head motion parameters and FD values associated with each data frame. The FIRMM software also generates and saves a JSON file of the full information displayed in the GUI at the conclusion of the scanning session. By loading the JSONs of completed scans, users are able to recreate the final FIRMM display of previous scan sessions.

EXAMPLES

The following examples illustrate various aspects of the disclosure.

Example 1: Validation of FIRMM Head Motion Prediction

To validate the FIRMM head motion prediction method described above, the following experiments were conducted.

For this study, extant rs-fcMRI data from a total of 1,134 scans of participants, teens, and young adults (457 female scans) with a mean age of 12.4 years (range=7.2-19.6 years), were utilized to compare FIRMM's FD calculations to standard post-hoc methods (Power et al., 2012; Power et al., 2015), and to estimate the scanning cost reductions had FIRMM been available at the time of scanning. The same data was also used to validate FIRMM's head motion prediction algorithm.

After applying FIRMM to extant datasets 1 and 2, FIRMM's utility was then tested for scanner operators in a new cohort of 29 neurotypical participants (FIRMM testing; dataset 3:11 female, mean age=11.5 years, age range=5.9-15.9 years).

The extant rs-fcMRI data used in these experiments included cohorts with attention deficit hyperactivity disorder (ADHD; dataset 1:425 participants, 140 female), autism spectrum disorder (ASD; dataset 1:84 participants, 17 female), a family history of alcohol use (FHA; dataset 2:308 participants, 143 female) and age-matched neurotypical controls (Controls; dataset 1, 2:341 participants, 157 female).

Dataset 1: ADHD, ASD, Neurotypical Controls

The ADHD and ASD cohorts, alongside age-matched neurotypical controls, were recruited as part of two ongoing longitudinal studies in the Fair and Nigg laboratories. For neurotypical and ADHD participants, participants were recruited from families who volunteered in response to mass mailings in the community. Their diagnostic grouping was carefully evaluated in best-estimate, multi-stage case finding procedure that included parent clinical interview using the Kiddie Schedule for Affective Disorders and Schizophrenia (K-SADS-E) (Orvaschel, H., Lewinsohn, P. M. & Seeley, J. R., Journal of the American Academy of Child and Adolescent Psychiatry 34, 1525-1535, (1995)), and parent and teacher standardized rating scales including the Conners Rating Scale, 3rd edition, ADHD Rating Scale, and Strengths and Difficulties Questionnaire. Intelligence was estimated with a three-subtest short form (Block Design, Vocabulary, and Information) of the Wechsler Intelligence Scale for Participants, and academic achievement was estimated with word reading and numerical operations subtests of the Wechsler Individual Achievement Test. A best-estimate diagnostic team reviewed all the acquired information to independently assign a diagnosis. Their agreement on ADHD/non-ADHD status was acceptable (k>0.85 for all diagnoses occurring at base rate >5% in the sample, including ADHD and ADHD subtype).

Participants (e.g., subjects) were excluded if they did not meet criteria for ADHD or non-ADHD groups. If they had evidence of tic disorder, psychotic disorder, bipolar disorder, autism spectrum disorder, or mental retardation. Participants were further excluded for parent-reported history of neurological illness, chronic medical problems, sensorimotor handicap, or significant head trauma (with loss of consciousness. Participants were also excluded if they were taking psychotropic medications other than psychostimulants. Participants were also excluded if they had metal in their bodies, which could contra-indicate MRI acquisition or cause imaging artifacts (e.g., dental braces, intracranial aneurysm clips). Additional exclusion criteria for control participants were: presence of conduct disorder or major depressive disorder. Only right-handed participants were included in the study. Participants prescribed psychostimulant medications were scanned after a minimum washout period of five half-lives (e.g., 24-48 h depending on the preparation).

For ASD participants, diagnosis was determined by a multi-disciplinary clinical team that utilized the ADOS (Lord, C. et al. J Autism Dev Disord 30, 205-223 (2000)). All participants also met ASD criteria on the ADI-R (Lord, C., Rutter, M. & Le Couteur, A. J Autism Dev Disord 24, 659-685 (1994)), using DSM-IV criteria (American Psychiatric Association, 2000). Participants with ASD were also assessed for ADHD by the same research methods noted above. As described above, participants with ASD who were taking psychostimulant medications were allowed to participate, but were washed out for a minimum of 24 to 48 hours (depending on formulation) or at least 7 half-lives of the formulation (e.g., the period of time it takes the body to metabolize/excrete half of the dose of the medication) prior to neuroimaging. Participants taking non-stimulant psychoactive medications (e.g., tricyclic antidepressants, SSRIs, MAO inhibitors, or antipsychotic medication and atomoxetine) were excluded from the study.

Dataset 2: Family History of Alcohol Use, Neurotypical Controls

Participants, ages 10-16 years, were recruited from the local community. Family history positive (FHP) youth were part of an ongoing longitudinal study in the Nagel laboratory and matched for demographic characteristics to family history negative participants (neurotypical controls). To determine eligibility, structured interviews were conducted by telephone with the participant and one of their parents. Exclusionary criteria included: lack of information on family history, family history of psychotic disorders (e.g., schizophrenia or bipolar I), diagnosis of a DSM-IV psychiatric disorder, significant lifetime alcohol or substance use (>10 lifetime alcoholic drinks or >2 drinks on any single occasion, >5 uses of marijuana, >4 cigarettes per day, any other drug use), neurological illness, significant head trauma (loss of consciousness >2 minutes), serious medical conditions, mental retardation or learning disability, prenatal exposure to drugs or alcohol, left-handedness, premature birth (<36 weeks), MRI contraindications, and pregnancy or possible pregnancy.

The Family History Assessment Module (Rice, J. P. et al. Comparison of direct interview and family history diagnoses of alcohol dependence. Alcoholism, clinical and experimental research 19, 1018-1023 (1995)) was used with at least one biological parent and the participating youth, to assess the presence of AUDs, as defined by DSM-IV criteria, in first (biological parents) and second degree relatives (biological aunts, uncles, and grandparents). Youth were categorized as family history negative (FHN) or family history positive (FHP) based on this information. FHN youth had no relatives with a history of AUDs. FHP youth had at least one parent or two or more second-degree relatives on the same side of the family with a history of AUDs. For FHP youth, a Family History Density (FHD) score was calculated indicating the degree of familial AUDs: parents contributed 0.5, grandparents 0.25, and aunts and uncles a weighted ratio of 0.25 divided by the number of their siblings. In the FHP group, scores ranged from 0.04 to 1.50.

Intellectual functioning (IQ) was estimated with the 2-subtest version of the Wechsler Abbreviated Scale of Intelligence (Wechsler, D. Wechsler Abbreviated Scale of Intelligence (WASI). (Psychological Corp, 1999)).

Validation Data Acquisition Parameters

Dataset 1 and 2 participants were scanned on a Siemens Tim Trio 3.0 Tesla Magnetom Tim Trio system (Siemens Medical Solutions, Erlangen, Germany) with a 12-channel head coil, located at OHSU's Advanced Imaging Research Center. A high-resolution T1-weighted MPRAGE sequence was acquired (resolution=1×1×1.1 mm). BOLD-weighted functional images were collected (along the anterior-posterior commissure) using T2*-weighted echo planar imaging (TR=2500 ms, TE=30 ms, flip angle=90°, FOV=240 mm2, 36 slices covering the entire brain, slice thickness=3.8 mm, resolution=3.75×3.75×3.8 mm). Three scans of 5 min of resting state BOLD data were acquired, during which participants were instructed to stay still and fixate on a white crosshair in the center of a black screen projected from the head of the scanner and viewed with a mirror mounted on a 12-channel head coil.

Results

Head Motion is Greatest in Young Participants, Patients

Figure 2B:
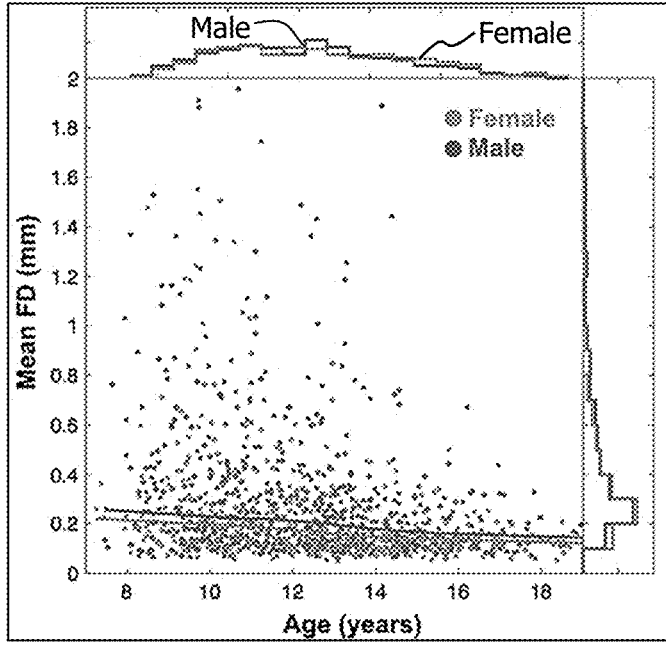
FIG. 2B is a graph summarizing the mean FD values as a function of the patient's age; each point is shaded according to each patient's sex.

MRI scans in demographic groups with very high head motion (e.g., movement) could potentially benefit greatly from utilizing FIRMM analytics. Therefore, the inventors examined the effects of age, gender, and different neuropsychiatric conditions on deleterious head motion in the set of 1,134 scan sessions from subjects 7-19 years old (FIGS. 2A and 2B). Consistent with previous research, a multivariate linear regression analysis (GLM: age, cohort, gender) showed that mean FD values were significantly greater at younger ages (effect of age, F=5.6, p<0.00001). FIGS. 2A and 2B show the effects of age, diagnosis and gender on head motion. The mean FD values (y-axis) for 1,134 MRI scan participants are shown relative to participants' ages (x-axes). Within all cohorts, there is massive inter-individual variance in head motion. FIG. 2A illustrates the mean framewise displacement (FD) values for participants based on the following diagnosis: control, family history of alcoholism (FHA), attention deficit hyperactivity disorder (ADHD), and autism spectrum disorder (ASD). FIG. 2B illustrates the mean FD values for participants based on gender and age. Patient and at-risk cohorts had overall greater FD values than controls (effect of cohort, F=19.3, p<0.00001). In addition, as shown in FIG. 2B, males had significantly greater FD values than females (effect of gender, F=5.5, p<0.02). The same patterns held true when the same analyses was conducted using the percentage of low movement frames (FD<0.2 mm, FD<0.3 mm, and FD<0.4 mm) as shown in FIGS. 7A-7F instead of mean FD as shown in FIGS. 2A and 2B.

Figure 3A:
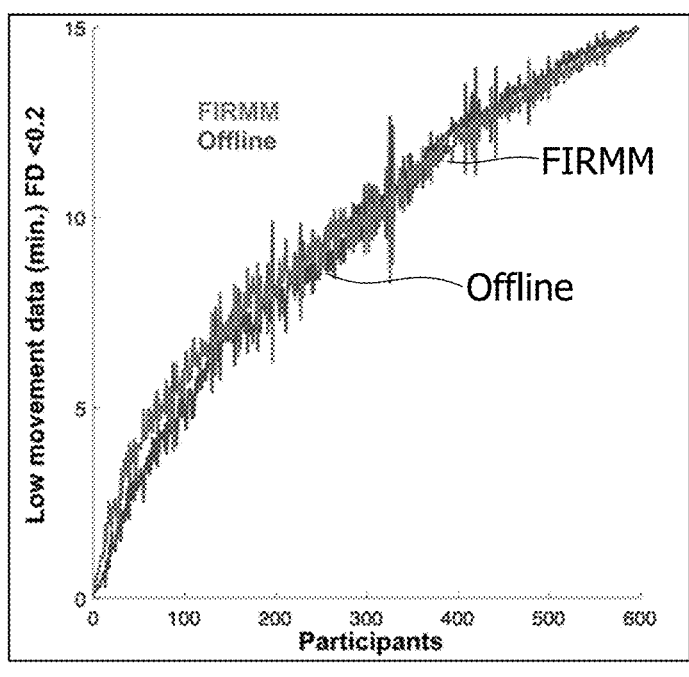
FIG. 3A shows a summary of the minutes of low movement MRI data (FD<0.2) obtained for each participant (y-axis), sorted by the mean number of low-movement across both methods for each participant (x-axis).
Figure 3B:
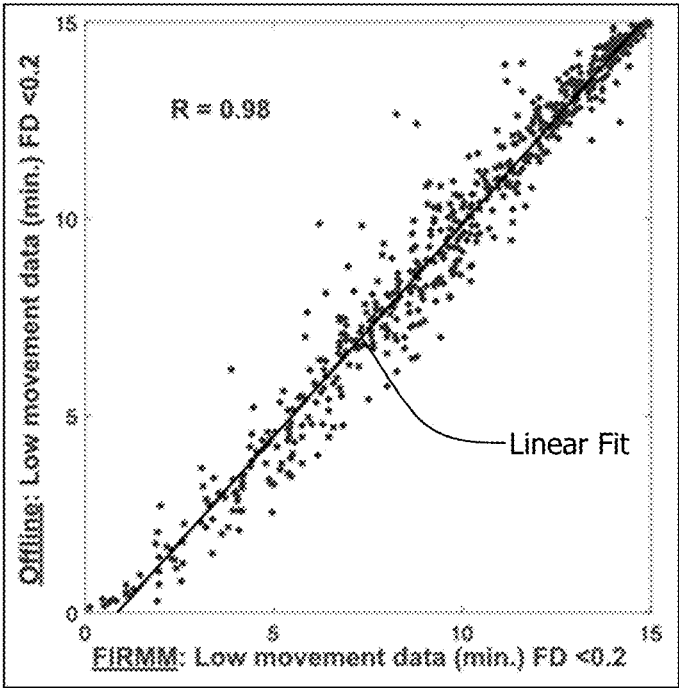
FIG. 3B shows the correlation (linear fit in black) between estimates of low-movement data (minutes) generated by FIRMM (x-axis) and the low-movement data identified using a standard offline post-hoc approach (y-axis).

FIGS. 7A-7F show the effects of age, diagnosis (e.g., control, FHA, ADHD, and ASD), and gender on head motion. The percentage of MRI data frames below the FD criterion cutoff (y-axis) for 1,134 MRI scan participants are shown relative to participants' ages (x-axis). Specifically, FIG. 7A illustrates the percentage of data frames below the criterion FD<0.2 for participants sorted by the described diagnoses (e.g., cohorts), and FIG. 7B illustrates the same data for participants sorted by gender. FIG. 7C illustrates the percentage of data frames below the criterion FD<0.3 for participants sorted by cohort, and FIG. 7D illustrates the same data for participants sorted by gender. FIG. 7E illustrates the percentage of data frames below the criterion FD<0.4 for participants sorted by cohort, and FIG. 7F illustrates the same data for participants sorted by gender. Demographics are a Poor Predictor of In-Scanner Head Motion If the inter-individual variance in FD within demographic groups were low, one could attempt to optimize MRI scan durations by simply using different scan lengths for different demographic groups. Yet, the analyses showed the variance of mean FD values across subjects to be very high in all cohorts ranging from about 0.1 to 2.0 mm across the entire sample. Some very young participants (e.g., patients) of less than 8 years of age had almost no head motion (mean FD~0.1 mm), while some typically developing adolescents had very high mean FD-values (>0.4 mm). Even though the GLM analysis showed that age, diagnosis and gender significantly affected mean FD values, these factors could only explain 13% of the variance (R²=0.13) across subjects. The high degree of inter-individual variance in FD across all cohorts shows that demographic criteria are insufficient predictors of how much data must be acquired for a given participant in order to retain a minimum number of low-movement data frames (See FIGS. 7A-7F).
FIRMM's Real-Time FD Calculations are Accurate FIRMM's FD calculations are not only fast, but also accurate, when compared to a standard, commonly utilized offline, post-hoc processing stream (Power et al., 2012; Power et al., 2015; Siegel et al., 2014). FIGS. 3A and 3B show a comparison of FD values generated by FIRMM and the offline approach. More specifically, FD data are shown from 597 participants (ADHD patients and controls) for whom a total of 360 rs-fcMRI data frames with a TR of 2.5 sec. were collected (15 minutes total). Further, FIG. 3A illustrates the percentage of low movement data (FD<0.2) for each participant included (y-axis), sorted by the mean percentage of low-movement frames across both methods (e.g., FIRMM and offline) for each participant (x-axis). FIG. 3B illustrates the correlation (r=0.98; linear fit shown, linear equation of y=1.07x−5.12) between estimates of low-movement data as calculated by FIRMM (x-axis) and the standard offline post-hoc approach (y-axis).

To test the accuracy of FIRMM's FD calculations, FD data from 1,134 scan sessions were combined from subjects across several pediatric patient or at-risk cohorts and age-matched controls between the ages of 7-19 years old (shown in FIGS. 2A and 2B). Across all subjects the FD values calculated by FIRMM in real time strongly correlated with the post-hoc FD numbers generated by the standard offline processing approach with an R-value of 0.981 (shown in FIG. 3A). The correlation (r) between offline processing and FIRMM in the number of usable low-movement frames (FD<0.2) was 0.984 (shown in FIG. 3B).

Using FIRMM to Scan Until Data Criterion is Reached Reduces Scan Times

Figure 4A:
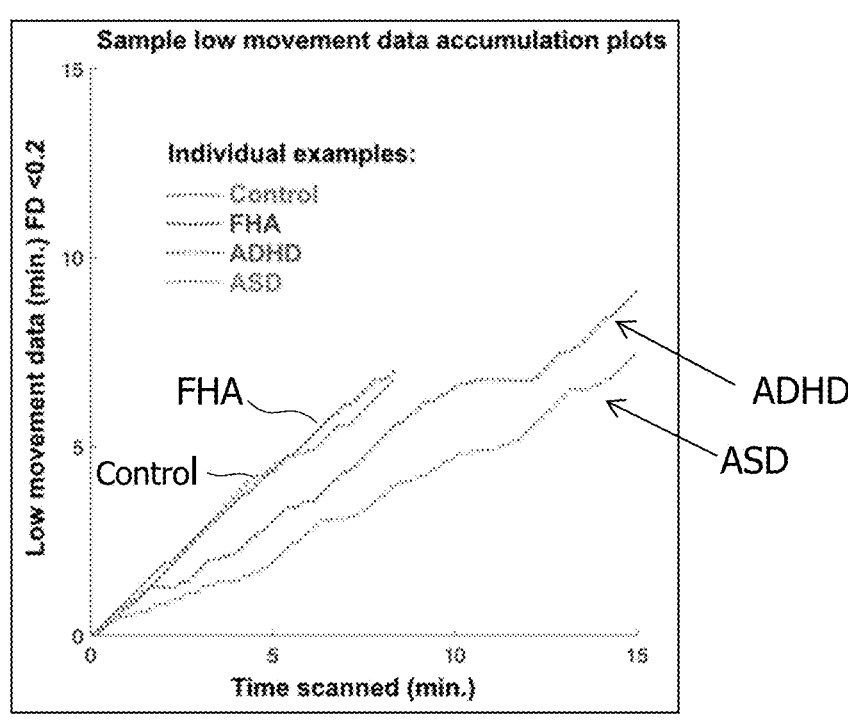
FIG. 4A shows the accumulation of low movement data (minutes FD<0.2; y-axis) relative to cumulative scanning time (minutes; x-axis) for a sample of individuals from each of the cohorts illustrated in FIG. 2A.
Figure 4B:
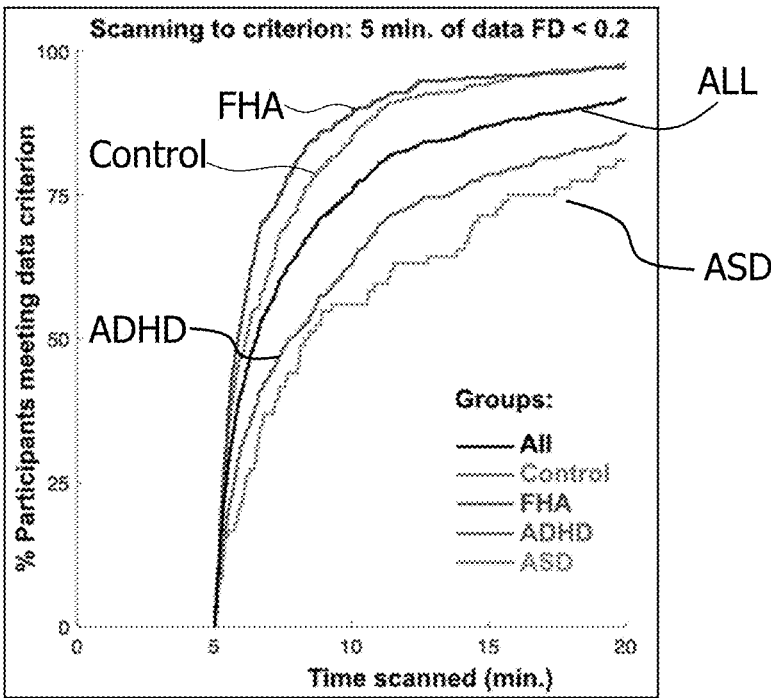
FIG. 4B shows the percentage of participants reaching the chosen data criterion of at least 5 minutes of data with FD<0.2 mm for each of the cohorts illustrated in FIG. 2A, as well as for the total sample of all cohorts.

The most rigorous frame-censoring discards all data frames with an FD value >0.2 mm. FIGS. 4A and 4B show the accumulation of low movement data (FD<0.2 mm). More specifically, FIG. 4A illustrates the accumulation of low movement data (minutes FD<0.2; y-axis) relative to the time spent scanning (minutes; x-axis) for sample individuals from each cohort. For standardization, the accumulation plot for those participants at the 50th percentile of usable data after 15 minutes of scanning, for each cohort was chosen for display. FIG. 4B illustrates the percentage of participants that have reached the chosen data criterion of at least 5 minutes of data with FD<0.2 mm for each cohort as well as the total sample. The area under the curve in FIG. 5B represents the relative time saved when scanning to criterion instead of scanning all participants for 20 minutes The relative time saved would have been 57% for the entire sample, 63% for controls, 64% for FHA, 49% for ADHD and 43% for ASD.

In order to obtain a reasonably stable estimate of a single subject's functional connectivity matrix, many research groups have been requiring at least 5 minutes of low-movement data per subject as a data criterion. Applying this criterion to the entire sample of 1,134 scan sessions, FIGS. 4A and 4B show that 20 minutes of rs-fcMRI data would have given at least 5 minutes of low-movement (FD<0.2 mm) data in 91% of participants. However, for 75% of the participants scanning could have been stopped after 10 minutes or less. For an additional 12% of the participants, data acquisition could have been stopped between 10-15 minutes. Another 4% of participants reached data criterion between 15-20 minutes of scanning.

In order to obtain a reasonably stable estimate of a single subject's functional connectivity matrix, many research groups have been requiring at least 5 minutes of low-movement data per subject as a data criterion. Applying this criterion to the entire sample of 1,134 scan sessions, it was found that 20 minutes of rs-fcMRI data would have given at least 5 minutes of low-movement (FD<0.2 mm) data in 91% of participants, as shown in FIGS. 4A and 4B. Thus, if FIRMM had been used to scan each participant until they reached the data criterion (5 minutes FD<0.2 mm), the total rs-fcMRI scan time and associated costs for this sample could have been reduced by 57%. In terms of scan time for the rs-fcMRI data ~216 hours could have been saved. Even if with conservatively estimated total hourly MRI scanning charges at $600/hr (MRI scanner usage fees, scanner operator(s) salaries and benefits, study participant payments), scanning to criterion with FIRMM would have reduced rs-fcMRI data acquisition costs by $130,000.

Recent research suggests that significantly more than 5 minutes of rs-fcMRI data are needed for high-fidelity functional connectivity estimation. Increasing the rs-fcMRI criterion beyond 5 minutes (FD<0.2 mm) would greatly increase MRI scanning costs and with it the potential cost savings from scanning to criterion with FIRMM.

Linear Accumulation of Low Movement Data Allows Prediction of Time to Criterion

To further improve FIRMM's utility for reducing scan times and costs an algorithm was built that accurately predicts the required scan time until the low movement data criterion will be reached.

When creating this prediction algorithm, the effects of time spent in the MRI scanner on head motion were visualized, as shown in FIGS. 5A-5C. FIGS. 5A-5F show that the linear accumulation of low-movement data allows accurate prediction of time-to-criterion. FIG. 5A shows the concatenated mean FD traces for all scanning sessions that included at least 3×5 minute rs-fcMRI scans. A few observations are noteworthy. As shown in FIG. 5A, in the higher moving clinical cohorts, mean FD values increased with time in scanner. Further, a small "reset" in mean FD is present such that head movement is lower for the start of the next scan session relative to the end of the prior session. In contrast, for the lower moving control cohort, mean FD increases only minimally over time. However, mean FD is less important than the mean percentage of low movement frames across the length of a scan session. Thus, the percentage of low movement frames (FD<0.2 mm) for the entire cohort, which is shown in FIG. 5B, indicates that the percentage of low movement frames (FD<0.2 mm) across each cohort declines only minimally with time spent in the scanner. FIG. 5B suggests that the accumulation of low movement frames (FD<0.2 mm) over time should be relatively linear, which is verified by the low-movement frame accumulation plot in FIG. 5C. Given these findings, a basic linear model was chosen to make real-time predictions about how long each participant would need to be scanned in order to reach the data criterion specified by the FIRMM user (FIG. 5D).

Using this model, it was shown that after acquiring 100 data frames, FIRMM makes accurate predictions about how much longer a participant must remain in the scanner in order to reach a certain number of low-movement data frames. FIG. 5E shows FIRMM's prediction error (in minutes; y-axis) and actual data accumulation (e.g., actual realization) across the length of the scan (x-axis) for the same subject as in FIG. 5D. The continuously updating prediction algorithm of FIRMM displays, to a scanner operator, an estimate of how much longer it will take to reach the pre-specified low-movement data criterion, as shown in FIG. 1. This feature is particularly helpful for very high-movement individuals, since it helps scanner operators estimate whether or not they will be able to collect the required amount of low-movement data during the allotted scanner time. FIG. 5F illustrates the robustness of the linear prediction algorithm. More specifically, FIG. 5F illustrates FIRMM's average prediction error (%) over time (x-axis) for each cohort and the entire group.

Using FIRMM Monitoring for the Early Termination of Scans in Very High Movement Subjects Reduces Aggregate Scan Time FIRMM can generate additional scan time savings by allowing scanner operators to terminate scans early for those participants with extremely low likelihoods of ever reaching the data criterion. For example, in the ADHD cohort 40 out of 425 participants had provided only 2.5 minutes (60 frames) of usable, low-movement data after 15 minutes of scanning (as shown in FIGS. 12-12F). For these high movement subjects even another 5 minutes of scanning would likely not have brought them to criterion and data collection could have been stopped after only 3 instead of 4 scans. Using FIRMM's linear prediction module, rs-fcMRI scans for some participants could have been terminated even earlier. In this manner, FIRMM allows MRI scanner operators to quickly move to the next MRI sequence in the study protocol, or to simply terminate the entire experiment, thus saving the participant and operator valuable time.

Example 1 Summary

The results of these experiments demonstrated the validity of the disclosed FIRMM head motion prediction method. The FIRMM head motion prediction method provides accurate real-time FD calculations, and accurate predictions in regards to the required scan time needed to reach the low movement data criterion. Further, the disclosed FIRMM head motion prediction method can be used to reduce scan times, thereby reducing the time and costs associated with 'overscanning.' Additionally, the FIRMM head motion prediction method further reduces scan times by enabling operators to terminate scan early for those participants who are extremely unlikely to reach the necessary low movement data criterion.

Example 2: Evaluation of FIRMM System by Scanner Operators

To evaluate the usage of the FIRMM head motion prediction method (e.g., FIRMM), described above, by scanner operators, the following experiments were conducted. After applying FIRMM to extant datasets 1 and 2, FIRMM's utility was tested for scanner operators in a new cohort of 29 neurotypical participants (FIRMM testing; dataset 3:11 female, mean age=11.5 years, age range=5.9-15.9 years).

The extant rs-fcMRI data used in these experiments included cohorts with attention deficit hyperactivity disorder (ADHD; dataset 1:425 participants, 140 female), autism spectrum disorder (ASD; dataset 1:84 participants, 17 female), a family history of alcohol use (FHA; dataset 2:308 participants, 143 female) and age-matched neurotypical controls (Controls; dataset 1, 2:341 participants, 157 female).

Dataset 3: FIRMM Usage Testing (Neurotypical Controls)

A total of 29 neurotypical participants between the ages of 5-16 years old were recruited from the local community and underwent rs-fcMRI scanning for a study that provided scanner operators access to FIRMM. Participants were excluded for medical, neurological, or psychiatric diagnoses such as ASD, mania, psychosis, cerebral palsy, epilepsy, intellectual delay/disability or chronic use of pharmaceutical agent thought to significantly alter brain function, tics, OCD, ADHD and cortical visual impairment. Participants were also excluded for any contraindications to MRI, including history of abnormal heart rhythm, pregnancy, pacemaker, metallic object(s) in body, extensive dental work, claustrophobia (as determined by asking subject whether he/she has ever experienced symptoms of claustrophobia such as feelings of anxiety/panic when in a confined space), and concussion with loss of consciousness >5 minutes. Being left-handed was not an exclusion criterion.

All participants completed the Tics, OCD and ASD modules of the KSADS (Kaufman et al., 1997), as well as the Behavior Rating Inventory of Executive Function (BRIEF) (Gioia et al., 2002), the Child and Adolescent Survey of Experiences, the Child Caregiving Involvement Scale, Child Depression Inventory, Current ADHD Rating Scale, Ever/ Lifetime ADHD Rating Scale, Participant's Yale-Brown Obsessive Compulsive Scale (CY-BOCS). Parents also completed a series of surveys using REDCap [Research Electronic Data Capture] hosted at Washington University (Harris et al., 2009) that in addition to standard demographics and medical history included the Edinburgh Handedness Inventory, Barratt Simplified Measure of Social Status (BSMSS), Constantino's Social Responsiveness Scale (SRS), Child Behavior Checklist (CBCL), Pediatric Quality of Life Inventory Parent Report (PedsQL), Child Sensory Questionnaire (CSQ), Parental Stress Index (PSI), and Behavioral Inhibition System and Behavior Activation System Questionnaire (BIS/BAS).

Validation Data Acquisition Parameters

Dataset 3 participants were scanned on a Siemens Tim Trio 3.0 Tesla Magnetom system (Siemens Medical Solutions, Erlangen, Germany) with a 12-channel head coil. A high-resolution T1-weighted MPRAGE sequence was acquired (resolution=1×1×1 mm).

Functional images were acquired using a BOLD contrast-sensitive echo-planar sequence (TE=27 ms, flip angle=90°, in-plane resolution 4×4 mm; volume TR=2.5 s). Whole-brain coverage was obtained with 32 contiguous interleaved 4 mm axial slices. Participants completed up to seven 6.8 minute BOLD scans. During two of seven scans participants were in the resting state, which consisted of viewing a centrally presented white crosshair (subtending <1° visual angle) on a black background. During the other five scans participants watched brief movies and/or received visual feedback about their head motion.

Results

FIRMM Alerts Scanner Operators to Unexpected Changes in Head Motion

FIGS. 6A and 6B show sample FD traces after implementing the FIRMM head motion prediction method described above. For the MRI scans shown here, access to FIRMM's real-time FD traces enabled scanner operators to intervene and improve MRI data quality. Testing the real-world utility of FIRMM in a new cohort of 29 typically developing participants revealed additional benefits. For example, as shown in FIG. 6A, a fairly sudden and significant reduction in a participant's FD values towards the end of a scanning session alerted the scanner operators to check on the participant who was found to have fallen asleep. FIRMM also allows experimenters to quickly test the effects of different scanning conditions on head movement in a given participant.

FIG. 6B shows data of one participant who underwent seven BOLD scans under slightly different conditions. It was immediately evident that one of the conditions (scan #4) showed greatly increased head movement, while all other experimental conditions were well-tolerated. FIG. 11 illustrates a screen-shot image of a FIRMM graphical user interface (GUI). In the exemplary aspect, a scanner operator's operator computing device 910 (shown in FIG. 9) may display real-time data such as, but not limited to, a participant's FD values over the course of the scan, the estimated time for completion based on the number of usable frames acquired, and the number of good and bad data images acquired based on the participant's FD values. In further aspects, FD thresholds (e.g., FD<0.2 mm, FD<0.3 mm, and FD<0.4 mm) may be color-coded on a real-time data plot or table displayed on the screen operator's operator computing device 910. For example, a FD visual representation as illustrated in FIG. 11 may be green for FD values <0.2 mm, yellow for FD<0.3 mm, and red for FD values <0.4 mm to alert the scanner operator as to the quality of data frames acquired during the scan.

Other usage cases provided by beta testing centers included using FIRMM to provide specific post-run feedback about head motion to motivate participants. This usage included sharing the percentage of low-movement data frames over the speaker system or displaying the FIRMM GUI (similar to FIG. 1) on the participant's screen in the scanner room for feedback and training purposes.

Example 2 Summary

The results of these experiments demonstrated the validity of usage of the disclosed FIRMM head motion prediction method by scanner operators. The FIRMM head motion prediction method alerts operators to sudden changes (e.g., increased or decreased FD values) by providing scanner operators real-time feedback by, for example, displaying data in real-time on the operator's GUI. This allows operators to respond to the feedback provided by FIRMM by taking measures to intervene during the MRI scan.

Example 3: Effect of Head Position Feedback Provided to MRI Subjects on Head Motion Using FIRMM Method To validate the effect of providing head position feedback to MRI subjects using the FIRMM head motion prediction method described above, the following experiments were conducted. The effects of viewing movie clips, viewing a fixation crosshair (e.g., rest), and receiving real-time visual feedback about head movement during the scans were investigated in 24 participants and adolescents.

Dataset 4: Head Position Feedback Participants

A total of 24 participants and adolescents between the ages of 5-15 years old were recruited from the local Washington University community. Of the 24 participants, 10 were female, 14 were male, and the mean age was 11.1 years. Participants completed the Tics, OCD, and ASD modules of the KSADS (Kaufman et al., 1997), as well as Current ADHD Rating Scale, Lifetime ADHD Rating Scale (Conners et al., 1998), the Multidimensional Anxiety Scale for Participants (MASC) (March et al., 1997), the Social Responsiveness Scale (SRS) (Constantino et al., 2003), the Kaufman Brief Intelligence Test II (K-BIT II) (Kaufman and Kaufman, 2004), the Barratt Simplified Measure of Social Status (BSMSS), and the Edinburgh Handedness Inventory (Oldfield, 1971). Assessments were collected using REDCap [Research Electronic Data Capture] hosted at Washington University (Harris et al., 2009). Of the 24 participants, 6 did not complete the KSADS, 1 did not complete the KBIT, and 3 did not complete the ADHD Rating Scale, SRS, MASC, or BSMSS, all due to time constraints.

Participants were excluded for parental-reported psychosis, mania, ASD, cerebral palsy, epilepsy, intellectual delay/disability and cortical visual impairment. Participants were also excluded for any contraindications to MRI, including a history of abnormal heart rhythm, pacemaker, metallic object(s) in body, extensive dental work, claustrophobia (as determined by asking the child whether he/she has ever experienced symptoms of claustrophobia such as feelings of anxiety/panic when in a confined space), and concussion with loss of consciousness >5 minutes. Participants were not excluded for tic disorders, anxiety disorders, ADHD, taking psychoactive medications, or handedness. Two of the participants had a previous diagnosis of ADHD, both of whom were taking stimulant medications. No other participants were taking psychoactive medications. One participant met diagnostic criteria for OCD and one met diagnostic criteria for Provisional Tic Disorder after the KSADS.

Validation Data Acquisition Parameters

Image Acquisition

Dataset 4 participants were scanned on a Siemens Tim Trio 3.0 Tesla MAGNETOM scanner (Siemens Medical Solutions, Erlangen, Germany) with a Siemens 12-channel Head Matrix Coil. A high-resolution T1-weighted MPRAGE structural image (resolution=1×1×1 mm) was acquired for each participant. Functional images were acquired using a BOLD contrast-sensitive echo-planar sequence (TE=27 ms, flip angle=90°, in-plane resolution 4×4 mm; volume TR=2.5 s). Whole-brain coverage was obtained with 32 contiguous interleaved 4 mm axial slices. Participants completed seven 6-minute 50-second long BOLD runs.

Experimental Design

Head motion was monitored, and feedback was presented to subjects undergoing MRI scans based on real-time calculations of head motion using the FIRMM head motion prediction method described above. Participants completed rest runs, during which they viewed a fixation crosshair, and movie runs, during which they viewed movie clips. For each of these stimulus conditions (e.g., rest runs and movie runs), they received three feedback conditions: none, fixed, and adaptive. During the fixed and adaptive feedback conditions, participants received online feedback about their head motion. Thus, the experiment consisted of a 2 (stimulus)×3 (feedback) design, resulting in six conditions. The first BOLD run always consisted of a baseline rest run in order to obtain a baseline assessment of each participant's movement during a standard eyes-open resting state scan. The following six runs consisted of the six experimental conditions, the order of which was counterbalanced across participants.

Participants were instructed to relax and hold as still as possible during all scans. During rest scans, they were told to look at the "plus sign" (e.g., crosshair) and during movie scans, they were told to watch the movie (as shown in FIGS. 12A and 12B). For the feedback scans, participants were told that a game was added such that the scanner will tell them if they are moving too much with a yellow/red plus sign (Rest) or box (Movie), and their goal was to keep the plus sign white (Rest) or keep the boxes away (Movie). For the Adaptive feedback condition, they were also told that when they hold still well, the scanner will take the game to the next level and make it a little harder.

Stimuli

FIGS. 12A and 12B illustrate a schematic of an exemplary feedback visual display provided to the participants. More specifically, FIG. 12A shows three feedback conditions (e.g., no to low motion feedback, medium motion feedback, and high motion feedback) for the rest scans, and FIG. 12B shows the same for the movie scans. As shown in FIG. 12A, for the rest scan, the crosshair may be color-coded such that the crosshair is a first-colored crosshair 1202 (e.g., white) for low to no motion, a second-colored crosshair 1204 (e.g., yellow) for medium motion, and a third-colored crosshair 1206 (e.g., red) for high motion. During the experiment, a white crosshair (subtending <1° visual angle) was centrally presented on a black background. For the rest conditions that included feedback (e.g., medium motion and high motion), the feedback consisted of the crosshair changing color to yellow for "medium" motion or red for "high" motion. Motion was determined using framewise displacement (FD; see below for description). The criteria for medium and high motion were tailored to the individual by extracting the individual participant's FDs during the baseline rest scan. The FDs for each frame of the baseline rest scan were sorted highest to lowest. The FD corresponding to the top 10% of frames was used as the high motion threshold, and the FD corresponding to the top 25% of frames was used as the medium motion threshold. Floor thresholds were set to 0.3 mm (high) and 0.2 mm (medium). For the Fixed Feedback condition, the thresholds were held constant for the duration of the run. For the Adaptive Feedback condition, the thresholds were held at these starting values for the first 20 frames of the run, after which they were recalculated according to the same criteria (10 and 25%) using the previous 20 frames of the current scan, and recalculated for each subsequent frame based on the previous 20 frames. New FD threshold values replaced the previous FD threshold values only if they were lower than the current ones (e.g., stricter). Thus, participants could decrease the FD threshold values until the end of the run or until reaching the floor thresholds of 0.3 and 0.2 mm.

As shown in FIG. 12B, the feedback conditions described above may be used for movie scans. For movie scans, visual feedback may be provided by FIRMM to the subject for medium motion by obstructing the movie with a rectangle centered on the screen. The rectangle may be a first-colored rectangle 1208 (e.g., yellow) to indicate medium motion. For high motion, the rectangle may be a larger second-colored rectangle 1210 (e.g., red). During the experiment, clips of cartoon blockbuster movies were shown to participants. Three movies were used to make a total of seven movie clips that were shown to participants in a randomized order. Movie clips were chosen on the basis of being engaging, but not overly exciting or upsetting, as determined by the experimenters. For each participant, a different clip was shown for each movie condition. For the movie conditions with feedback, the feedback consisted of a yellow rectangle centered on the screen (500×375 pixels) for medium motion, or a larger red rectangle centered on the screen (800×600 pixels) for high motion that occluded the movie while it continued to play. The criteria for feedback during the fixed and adaptive feedback conditions were the same as that for the Rest feedback conditions.

Stimuli were presented using the Psychophysics Toolbox Version 3 in Matlab, and back-projected onto a MR-compatible rear-projection screen at the end of the scanner bore, which the participants viewed through a mirror mounted onto the head coil. The screen size was 1024×768 pixels. MR-compatible headphones were worn to dampen the noise of the scanner and to listen to the movies during the Movie conditions.

Image Preprocessing

Functional images from each participant were preprocessed to reduce artifacts (Shulman et al., 2010), including (i) sinc interpolation of all slices to the temporal midpoint of the first slice, accounting for differences in the acquisition time of each individual slice, (ii) correction for head motion within and across runs, and (iii) intensity normalization to a whole brain mode value (across voxels and TRs) of 1000 for each run. Atlas transformation of the functional data was computed for each individual using the MPRAGE T1-weighted scan. For one participant, the T1-weighted scan contained too much motion artifact for adequate registration, and thus, a T2-weighted image was used. Each functional run was resampled in atlas space on an isotropic 3 mm grid combining movement correction and atlas transformation in a single interpolation. The target atlas was previously created from MPRAGE scans of thirteen 7-9 year old participants (seven males) and twelve 21-30 year old adults (six males), collected on the same Siemens 3T Trio used in this study. This atlas was made to conform to the Talairach atlas space using the spatial normalization method of Lancaster et al. (1995).

Functional Connectivity Preprocessing

For resting-state functional connectivity MRI analyses, additional preprocessing steps were used to reduce spurious variance unlikely to reflect neuronal activity. These steps included (i) demeaning and detrending, (ii) multiple regression of nuisance variables from the BOLD data (nuisance variables included motion regressors derived by Volterra expansion (Friston et al., 1996), individualized ventricular and white matter signals constructed using Freesurfer's segmentation, brain signal averaged across the whole brain, and the derivatives of these signals), (iii) temporal band-pass filtering (0.009 Hz<f<0.008 Hz), and (iv) spatial smoothing (6 mm full width at half maximum). For the one participant with excessive movement contaminating the T1 image, the T2-weighted image was used for creation of the nuisance regressor masks using FSL's fast segmentation.

Motion Censoring Method

A volume censoring procedure (Power et al., 2014) in which volumes with FD>0.3 were identified and censored from the data was implemented. The threshold of 0.3 was chosen because at this movement threshold, even the best performing subjects received the "red" warning that movement was too high during the feedback conditions. Given this approach, head motion was indexed by calculating both mean FD and the number of frames retained after censoring.

Results

Real-Time Feedback and Movie Watching Reduced Movement in Younger Participants

To test the effects of real-time feedback and movie watching on FD, a repeated-measures ANOVA was run with mean FD as the dependent variable and with the within-subjects factors stimulus (rest, movie) and feedback type (none, fixed, adaptive). There was a significant main effect of stimulus, such that FD was lower for movie (M=0.28, SD=0.30) than for rest (M=0.60, SD=0.91), F(1, 23)=4.77, p=0.039. There was a significant main effect of feedback type, with the lowest FD for the fixed condition (M=0.26, SD=0.23), then the adaptive condition (M=0.45, SD=0.61), and highest for no feedback (M=0.61, SD=0.98), F(2, 46)=3.8, p=0.03. The stimulus×feedback type interaction was not significant (p=0.15).

Given the potential effects of age and sex on in-scanner head motion, the same stimulus×feedback type ANOVA was run with the additional between-subjects factors of (a) age group (younger [5-10 years old, n=11], older [11-15 years old, n=13]) and (b) sex (male, female). There were significant main effects of stimulus, F(1, 20)=8.26, p=0.009, Feedback type, F(2, 40)=4.95, p=0.012, and age group, such that the younger group (M=0.74, SD=0.79) had higher FD than the older group (M=0.18, SD=0.73), F(1, 20)=6.36, p=0.02. There was no main effect of the subject's sex (p=0.995). There was also a significant stimulus×age group interaction, F(1, 20)=8.92, p=0.007, and a significant feedback×age group interaction, F(2, 40)=3.61, p=0.036. No interactions with sex were significant.

Further, the stimulus×feedback×age group interaction was close to significant, F(2, 40)=3.14, p=0.054. FIGS. 13A and 13B illustrate the nature of this interaction by showing that the effects of movie watching and feedback on FD were driven by the younger participants. More specifically, FIG. 13A shows the mean FD calculated for younger participants (5-10 years) and older participants (11-15 years) for rest scans and movie scans for the three feedback conditions (e.g., no feedback, fixed feedback and adaptive feedback). FIG. 13B shows the percentage of MRI frames retained after volume censoring (FD<0.3 mm). The error bars in both FIGS. 13A and 13B indicate standard error of the mean.

Though the order of the conditions was counterbalanced, an effect of time in the scanner was tested by conducting a One-way ANOVA with Run as the within-subjects factor (7 levels for 7 runs, the first was the baseline rest run). There was no significant effect of Run (p=0.67).

The effects of viewing movies and receiving online feedback on the number of frames retained (e.g., with FD<0.3 mm) using the frame censoring approach described above is shown in FIG. 13B. Repeated-measures ANOVAs were run with number of frames retained as the dependent variable. The stimulus (rest, movie)×feedback type (none, fixed, adaptive) ANOVA revealed a significant main effect of stimulus with fewer frames retained during rest (M=124, SD=35.4) than during movies (M=136.1, SD=28.7), F(1, 23)=10.4, p=0.004, and a significant main effect of feedback type, with the fewest frames retained during no feedback (M=123.9, SD=41.3), than with the adaptive feedback (M=129.6, SD=33.4). The most frames were retained during fixed feedback (M=136.7, SD=23.6), F(2, 46)=3.79, p=0.03. There was no significant interaction of stimulus×feedback type (p=0.26).

Age group and sex were included as between-subjects factors. Again, a significant main effect of stimulus, F(1, 20)=11.5, p=0.003, and feedback type, F(2, 40)=4.15, p=0.023 were discovered. There was also a significant main effect of age group, such that fewer frames were retained in the younger group (M=116.74, SD=42.9) than in the older group (M=142.39, SD=40.5), F(1, 20)=4.54, p=0.046, but no main effect of Sex (p=0.45). The stimulus×age group interaction was significant, F(1, 20)=5.88, p=0.025. FIGS. 13A and 13B show that, as with mean FD, the effects were driven by the younger participants.

Seed Maps and Network Structure are Qualitatively Preserved Across Conditions

Imaging data were analyzed from 17 participants, all of whom retained at least 72 frames (3 min) of data in each condition after motion censoring. The other participants did not have enough data in one or more conditions for analysis. Importantly, the amount of data and mean FD post motion censoring did not differ significantly between conditions in these 17 participants (all p's>0.1). From these data, seed maps were constructed for six canonical seed regions: left motor cortex (Talairach coordinates: −38, −29, 57), right motor cortex (39, −19, 56), left angular gyrus (−46, −63, 31), left precuneus (9, −56, 16), right ventromedial prefrontal cortex (7, 37, 0), and dorsal anterior cingulate cortex (−1, 10, 46). Seeds with a 10 mm diameter centered on the canonical coordinates were created, and the time courses in the seed regions were then cross-correlated with all other voxels in the brain. Seed maps were generated for each condition (fixation no feedback, fixation fixed feedback, fixation adaptive feedback, movie no feedback, movie fixed feedback, movie adaptive feedback).

FIGS. 14A and 14B show group-averaged seed maps replicating canonical functional connectivity (FC) profiles. More specifically, FIG. 14A shows seed maps for the left angular gyrus (Talairach coordinates −46, −63, 31), and FIG. 14B shows seed maps for the right motor cortex (Talairach coordinates 39, −19, 56) for the 17 participants with useable FC data in every condition. FC maps of the six predefined, canonical seed regions exhibited the expected FC profiles. For example, a seed placed in the left angular gyrus produced correlations with other regions belonging to the default-mode network, including the homotopic angular gyrus and posterior cingulate cortex. The RSFC seed maps looked qualitatively similar across scan conditions.

FC correlation matrices were constructed for the 17 subjects with adequate imaging data. For each participant, FC time courses were extracted from 264 previously defined regions of interest (ROIs). The cross correlations between all 264 ROIs (10 mm diameter spheres) were computed. These correlations can be viewed in matrix form, with the regions organized according to previously described functional network scheme. Correlation matrices were constructed for each participant for each condition and normalized using Fisher r-to-z transform. Matrices were averaged across participants to check for the expected block structure (e.g., strong within network correlations) in each condition.

In order to test whether or not the behavioral interventions significantly affected FC, the correlation matrices were statistically compared across conditions using a paired version of object-oriented data analysis (OODA)—a method for contrasting connectomes described in (La Rosa et al., 2012; La Rosa et al., 2016). Briefly, OODA computes average weighted matrices following the Gibbs distribution for each condition, and compares the matrices by taking the Euclidian distance between them. To assign a p-value to the observed differences, the samples are bootstrapped (N=1000 times) creating a distribution of distances.

FIGS. 15A-15C illustrate correlation matrices displaying functional connectivity between 264 previously-defined regions of interest (ROI) organized by network. Data are shown for the 17 subjects with useable FC data in every condition. More specifically, FIG. 15A shows data for feedback conditions Rest No Feedback and Movie No Feedback. FIG. 15B shows data for feedback conditions Rest Fixed Feedback and Movie Fixed Feedback. FIG. 15C shows data for feedback conditions Rest Adaptive Feedback and Movie Adaptive Feedback. FIGS. 15A-15C demonstrate the expected network structure with strong within-network correlations and lower between-network correlations. The expected block structure is present for all conditions, demonstrating higher within than between network correlations For FIGS. 15A-15C, 16A-16D, and 17, Aud=auditory, CB=cerebellum, CO=cingulo-opercular, DAN=dorsal attention network, DMN=default mode network, FP=fronto-parietal, PMN=parietal memory network, Sal=salience, SC=subcortical, SM=somatomotor, SM(lat)=somatomotor lateral, VAN=ventral attention network, and Vis=visual.

FC is Significantly Altered by Movies, but not by Feedback

Paired-sample t-tests revealed that no connections survived multiple comparison corrections for the contrasts between feedback conditions (Rest No Feedback vs. Rest Fixed Feedback, Rest No Feedback vs. Rest Adaptive Feedback, Rest Fixed Feedback vs. Rest Adaptive Feedback). When comparing the Rest No Feedback and Movie No Feedback conditions, 48 functional connections were significantly different, most of which were visual network-to-visual network connection. Given the large number of tests and the need for multiple comparisons correction, these analyses were very conservative and may not have revealed all of the true differences. OODA allows direct comparison of the correlation matrices between conditions as a whole, and therefore, may be more sensitive at detecting differences. These analyses revealed a significant difference between Rest No Feedback and Movie No Feedback (p<0.001), but no significant differences between Rest No Feedback and Rest Fixed Feedback (p=0.33), Rest No Feedback and Rest Adaptive Feedback (p=0.45), and Rest Fixed Feedback and Rest Adaptive Feedback (p=0.9). Thus, movies significantly altered FC when compared to the resting state, while feedback did not, as shown in FIGS. 16A-16D.

FIGS. 16A-16D show the differences in FC between key conditions. Differences between movies and rest were structured (and significant), while differences were less (and not significant) between feedback conditions. FIG. 16A shows differences in FC between Rest No Feedback and Movie No Feedback. FIG. 16B shows differences in FC between Rest No Feedback and Rest Fixed Feedback. FIG. 16C shows differences in FC between Rest No Feedback and Rest Adaptive Feedback. FIG. 16D shows differences in FC between Rest Fixed Feedback and Rest Adaptive Feedback.

In order to interrogate the nature of the significant difference between Rest No Feedback and Movie No Feedback conditions, post-hoc permutation analyses were run to identify specific network-to-network blocks that differed. FIG. 17 displays the results, showing the specific and systematic effects of movie watching. More specifically, FIG. 17 shows significant network-level differences between Rest No Feedback and Movie No Feedback conditions. Absolute difference in r is shown for significant network-to-network blocks. As seen in FIG. 17, there were significant differences involving frontoparietal network FC with many other networks, including sensorimotor processing networks (somatomotor, auditory, visual), top-down control networks (cingulo-opercular, dorsal attention), and the default-mode network. There were also differences in FC within and between the visual network and between the auditory network and other networks. These results demonstrate that watching a movie alters FC within and between specific functional networks, involving both sensorimotor processing and top-down control.

Example 3 Summary

The results of these experiments demonstrated the validity of presenting visual feedback to a subject undergoing an MRI scan based on real-time calculations of head motion using the disclosed FIRMM head prediction method. Real-time head motion feedback, in general, reduced motion during MRI scans in young participants. Specifically, in young participants, movie watching during MRI scans reduced head motion. The results of these experiments further disclosed that movies, not feedback, significantly altered functional connectivity (FC) MRI data. Thus, real-time visual feedback may be provided by FIRMM to the subject undergoing the MRI scan by (a) changing the colors of the crosshair and (b) obstructing the movie clip with color-coded rectangles of varying sizes to allow the subject, without intervention from the scanner operator, to adjust his or her body movements accordingly.

Example 4: Identification of Respiratory Artifacts in Movement Estimates in fMRI To identify respiratory artifacts that contaminate motion estimates, the following experiments were conducted. More specifically, multiband data and single-band (e.g., single shot) data were obtained from a subject provided with a visual stimulus or a 'respiratory cue' during the MRI scan. A visual stimulus was provided so as to control the subject's breathing to exactly 11 Hz throughout the MRI scan. The respiratory traces and power spectra were compared between the two data types (e.g., multiband imaging data and single-band imaging data).

Dataset 4: ABCD—Multiband

Data from the ABCD study was used. ABCD participants were of ages 9-10 years of age, and selected from the Oregon Health and Science University (OHSU). ABCD participants and families were recruited through school- and community-based mailings, targeted to reach an ethnic and demographic sample representative of the United States population. Exclusion criteria were set forth largely to ensure that participants would be able to complete the study protocol, and included current diagnosis of a psychotic disorder (e.g., schizophrenia), a moderate to severe autism spectrum disorder, intellectual disability, or alcohol/substance use disorder, lack of fluency in English (for the child only), uncorrectable sensory deficits, major neurological disorders (e.g., cerebral palsy, brain tumor, multiple sclerosis, traumatic brain injury with loss of consciousness >30 minutes), gestational age <28 week or birthweight <1.2 kg), neonatal complications resulting in >1 month hospitalization following birth, and MRI contraindications (e.g., braces).

Prior to MRI scanning, respiratory monitoring bellows (e.g., belts) were placed comfortably around the participant's ribs (with sensor horizontally aligned just below the ribcage). Further, a pulse oxygen monitor was placed on the non-dominant index finger of the participant. All participants had both sufficient EPI data to examine (e.g., 4, 5 minute runs) and quality physiologic data obtained from Siemens built in physiologic monitor and respiratory belt.

Dataset 5: Neurotypical Controls

Data from OHSU's in-house 'single shot' (e.g., single-band) dataset as to neurotypical controls (e.g., control cohort) was used. The controls consisted of 321 scanning sessions, with 149 female scan sessions. These neurotypical controls were recruited as part of two ongoing longitudinal studies in the Fair and Nigg laboratories. Participants were recruited from families who volunteered in response to mass mailings in the community. Their diagnostic category (e.g., control) was carefully evaluated in best-estimate, multi-stage case finding procedure.

Exclusion criteria were set forth for ADHD, tic disorder, psychotic disorder, bipolar disorder, autism spectrum disorder, conduct disorder, major depressive disorder, intellectual disability, neurological illness, chronic medical problems, sensorimotor disability, and significant head trauma (with loss of consciousness). Further, participants were excluded if they were taking psychotropic medications or psychostimulants. Participants were also excluded if they had contraindications to MRI. Only right-handed participants were included in the study.

Evaluation Data Acquisition Parameters

ABCD participants were scanned on a Siemens 3.0 T Magnetom Prisma system (Siemens Medical Solutions, Erlangen, Germany) with a 32-channel head coil, located at OHSU's Advanced Imaging Research Center. A high-resolution T1-weighted MPRAGE sequence was acquired (resolution=1×1×1 mm). BOLD-weighted functional images were collected (along the anterior-posterior commissure) using T2*-weighted echo planar imaging (TR=0.80 ms, TE=30 ms, flip angle=90, FOV=240 mm2, 36 slices covering the entire brain, slice thickness=3.8 mm, resolution=3.75×3.75×3.8 mm). Four runs of 5 min of resting state BOLD data were acquired, during which ABCD participants were instructed to stay still and focus on a white crosshair in the center of a black screen projected from the head of the scanner and viewed with a mirror mounted on the 32-channel head coil. This is the rest condition as discussed above, and is similar to the feedback visual display shown in FIG. 12A.

Neurotypical control participants (e.g., single shot dataset) were scanned on a Siemens Tim Trio 3.0 T Magnetom Tim Trio system (Siemens Medical Solutions, Erlangen, Germany) with a 12-channel head coil, located at OHSU's Advanced Imaging Research Center. A high-resolution T1-weighted MPRAGE sequence was acquired (resolution=1×1×1 mm). BOLD-weighted functional images were collected (along the anterior-posterior commissure) using T2*-weighted echo planar imaging (TR=2500 ms, TE=30 ms, flip angle=90, FOV=240 mm2, 36 slices covering the entire brain, slice thickness=3.8 mm, resolution=3.75×3.75×3.8 mm). Three runs of 5 min of resting state BOLD data were acquired, during which control participants were instructed to stay still and fixate on a white crosshair in the center of a black screen projected from the head of the scanner and viewed with a mirror mounted on a 12-channel head coil. This is the rest condition as discussed above, and is similar to the feedback visual display shown in FIG. 12A.

Data Processing Parameters

All data were processed following slightly modified processing pipelines from the Human Connectome Project. Such pipelines require the use of FSL (Smith et al. 2004; Jenkinson et al. 2012; Woolrich et al. 2009) and FreeSurfer tools (Dale et al. 1999; Desikan et al. 2006; Fischl & Dale 2000). Because all participants did not produce quality T2 images, the T2 specific imaging in this pipeline was removed.

Gradient distortion corrected T1-weighted volumes were first aligned to the MNI's AC-PC axis, and then non-linearly normalized to the MNI atlas. The T1w volumes were subsequently re-registered using boundary based registration (Greve & Fischl 2009) to improve alignment. The T1w's brain was further segmented using recon-all from Free-Surfer. The BOLD data was corrected for field distortions (using FSL's TOPUP) and processed by doing a preliminary 6 degrees of freedom linear registration to the first frame. After this initial alignment, the average frame was calculated and used as final reference. The BOLD data was subsequently registered to this final reference and to the T1-weighted volume, all in one single step, by concatenating all the individual registrations into a single registration.

Surface registration. The bold data confined within the gray matter was registered into a mesh that followed the contour of the mid thickness defined by the cortical ribbon. The cortical ribbon was defined by taking into account the T1-weighted and T2-weighted volumes. This ribbon was used to quantify the partial contribution of each voxel in the BOLD data. Timecourses in the cortical mesh were calculated by obtaining the weighted average of the voxels neighboring each vertex within the mesh, where the weights were given by the average number of voxels wholly or partially within the cortical ribbon.

Voxels with high coefficient of variation, indicating difficulty with tissue assignment or containing large blood vessels, were excluded. Next, the resulting timecourses in this mesh were down sampled into a standard space of anchor points (grayordinates), which were defined in the brain atlas and mapped uniquely to each participant's brain after smoothing them with a 2 mm full-width-half-max Gaussian filter. Subcortical regions were treated and registered as volumes. Two thirds of the grayordinates were vertices located in the cortical ribbon while the remaining grayordinates were subcortical voxels.

Nuisance regression. The minimally processed timecourses reported by the HCP pipelines were further preprocessed to minimize the effect of unwanted signals in the BOLD data. This extra step consisted of regressing out the average signal from the grey matter, white matter, and ventricles. This extra step further consisted of regressing out the average signal from the movement between frames from the six image alignment parameters x, y, z, $\theta_x$, $\theta_y$, and $\theta_z$ on the actual and the previous TR and their squares, which correspond to the Volterra series expansion of motion. The regression's coefficients (beta weights) are calculated solely based on frames with low movement, but regression is calculated considering all the frames to preserve temporal order in the data for filtering in the time domain. Next, time courses were filtered using a first order Butterworth band pass filter to preserve frequencies between 0.009 and 0.080 Hz.

Estimating Respiration Characteristics

Normal physiological ranges of respiration rate change with age, going from 44 breaths per minute (bpm) at birth to 16 bpm at the age of 18 years old. The corresponding frequency in Hz can be obtained by dividing the subject's respiration rate, in bpm, by 60. For a respiration rate of 20 bpm, a typical value in teenagers, the corresponding frequency in Hz is 0.$\overline{3}$. This means that a respiration rate of 20 bpm is revealed by a peak at a frequency of 0.$\overline{3}$ Hz in a power spectrum graph.

The bold data was acquired at a frequency of 1/TR. In particular for the ABCD study, the TR=0.8 seconds, and the sampling frequency was 1.25 Hz (1.25=1/0.8). A power spectrum of a signal acquired at 1.25 Hz shows the individual (and orthogonal) sinusoidal signals that, if added, can recreate the original temporal signal. Those individual sinusoidal signals have frequencies that go from zero until 0.625 Hz, e.g., 1.25/2 Hz, or, in general, one half of the sampling frequency, known as the Nyquist frequency. A signal of 20 bpm (0.$\overline{3}$ Hz), if existing, can be seen in the spectrum of the motion estimates, since 0.625 Hz>0.$\overline{3}$ Hz.

For slower TRs (or faster respiration rates), for example for the control (e.g., OHSU) dataset (TR=2.5 s), the respiration rate signal could be "aliased" into the motion estimates. In other words, the peak of the respiration rate would look like a peak at a slower frequency. Aliasing happens when a fast process is acquired at low sampling rates. In general, for a sampled process, signals faster than Nyquist (e.g., one half of the sampling frequency) are aliased (folded) in the spectrum. Aliasing happens by the combination of two factors: the TR and the subject's respiration rate (see figure xx "show alias"). For example, the same signal of 20 bpm (0.$\overline{3}$ Hz) would look like a peak at a frequency of 0.1$\overline{6}$ Hz at a TR of 2 seconds (see figure xx "show alias"). In general, the aliased frequency can be calculated as follows:

$$RR_{a,HZ} = abs(RR_{HZ} - floor((RR_{HZ} + f_{Ny})/f_S) * f_S),$$

where $RR_{a,HZ}$ is the aliased' respiration rate frequency (in Hz), $RR_{HZ}$ is the real respiration rate frequency (in Hz), $f_S$ is the sampling frequency (in Hz) and can be calculated as 1/TR. Finally, $f_{Ny}$ is the Nyquist frequency, which is one half of the sampling frequency $RR_{HZ}$.

Estimating Motion Frequency Content

The frequency content of the motion estimates were calculated using power spectral density estimation. Power estimation reports the average amplitude of the individual components that, if added, can reconstruct the original signal. This standard procedure in signal processing consists of windowing the data, calculating the Fourier Transform of each window, and averaging the amplitudes for each frequency across windows. To minimize leakage of frequency associated with segmenting the data, we windowed each segment multiple times using different window types (e.g., "tapers"). This calculation was done in Matlab using the function pmtm.

Qualitative Assessment Conducted by Examining Correlation Outcomes of Seed Regions Qualitative assessments were conducted using the effects of motion on BOLD data in a format introduced by Powers et al. A version of this representation, as shown by FIGS. 18A and 18B, was used. As seen in FIGS. 18A and 18B, data (representing each voxel or, for surface data, greyordinates) from each masked EPI frame is displayed as a vector. Each vector, again representing each frame in a 'BOLD run,' is stacked horizontally in the time domain. This procedure allows one to view, in one shot, all of the data that is represented in a given run (or full study via concatenated runs) for a given subject. These rectangular grey plots of BOLD data (e.g., BVD plots) as shown in FIGS. 18A and 18B have been described in detail elsewhere.

As illustrated in FIGS. 18A and 18B, on top of the BVD plots are DVARS measurements (D for derivative of time-series, VAR for RMS variance across voxels) prior to connectivity preprocessing ("Pre reg"), post the regression phase of the preprocessing ("Post reg"), and after the all of the processing, including filtering ("Post all"). DVARS is a good estimate of motion that does not rely on the frame-realignment. Also included is a mean ("Mean") and standard deviation ("Std") plot of the whole brain signal.

Frame displacement (FD) is plotted across the run. For each frame or data point in the FD line plots is a colored circular mark, which represents the FD threshold in which a given frame would have been excluded from future analysis. The corresponding threshold line is displayed by a matching color horizontally in the plot. For example, dots of a first color (e.g., grey dots) may represent frames that would be excluded at an FD threshold of 0.6 (unless they would also be excluded at a higher threshold). Dots of a second color (e.g., green dots) may represent an FD threshold of 0.1, and dots of a third color (e.g., orange) may represent an FD threshold of 0.2. These dots are then duplicated on the upper bound of the graph so that the various thresholds can be easily compared against the BVD plots. The idea here is that the proper threshold for removing unwanted movement corrupted data should line up, at least visually, with the corrupted data visualized by the BVD plot.

Qualitative Assessment Conducted Utilizing a Quality Measure

Qualitative Assessment was conducted utilizing a quality measure introduced by Power et al, 2014. The steps are illustrated in FIGS. 19A-19D and the results are illustrated in FIGS. 30A-30C. FIG. 19A illustrates the first step where FD values are used to order subject volumes by decreasing quality. In the second step, as shown in FIG. 19B, a sliding window of a number of volumes is used to calculate correlations (in volumes 1-50, 2-51, etc.). Mean correlations in the first 10 boxcars define zero. In the third step, instead of using $\Delta r$ in short distance connections as an outcome measure, a correlation (r) between the baseline matrix and the given sliding boxcar matrix. The correlation is shown in FIG. 19C. Step 4 consists of repeating steps 1-3, as shown in FIGS. 19A-19C, using permutations of data quality metric labels (e.g., FD values) to establish null outcome distributions. Step 5, as shown in FIG. 19D, includes comparing the true values to the null distribution to show at what FD value the matrices are different from random at a confidence of p<0.05. As shown in FIG. 19D, values in grey near 0 are non-significantly different than random. Values in grey at the bottom of the plot are significantly different from random.

After generating the data quality metric-ordered outcomes of all subjects, and for all conditions (e.g., without filter, with general filter, with subject specific filter), the data quality metric-ordered outcomes were analyzed to determine what procedures are the most similar or deviant from random as a whole. The rank of the data quality metric-ordered outcomes across subjects was plotted, as shown in FIG. 20A, and binned, as shown in FIG. 20C. As seen in FIG. 20C, this procedure provides a vertical distribution of ranks in a data quality metric bin.

The graphs shown in FIGS. 20A-20C are interpreted such that if the FD traces are accurately representing movement in the BOLD data, the shift from more randomly distributed ranks occurs quickly, as the mean FD values rise. This result would ensue because in the optimal case, where FD is perfectly accurate at depicting true movement in the scanner, the baseline measurement (e.g., the highest quality frames) will have very little movement. Thus, when compared to frames that have higher movement, divergence will ensue quickly (e.g., will quickly become divergent from random), as shown in FIGS. 20A-20C. In the case where FD is randomly associated with true movement in the BOLD, there will be no divergence because the baseline measurement will have an equal amount of movement frames compared to the other measurements. Thus, the FD measurements that are most accurate should skew leftward relative to the others.

Results

Fundamental Difference Exists in Motion Traces Produced by Multiband Data when Compared to Single-Band Data FIGS. 18A and 18B, as discuss above, provide an example of BVD plots for a very low moving subject who had been scanned both with multi-band acquisitions and single-band acquisitions for 5 minutes. The subject was also provided with a visual stimulus, or 'respiratory cue' such that his breathing would be set exactly at 11 hz throughout the run. FIGS. 18A and 18B show that the movement values as measured with FD appear to be higher with the multi-band data than the single-band. Indeed, despite no apparent artifacts showing in the BOLD data or other quality measurements of DVARS or standard deviations of the whole brain, many frames do not pass the standard cutoff of FD<0.2 for the multiband data only. These qualitative observations suggest a fundamental difference in motion estimates provided by multiband data, as compared to single shot (e.g., single-band) data.

Multiband Imaging Reveals Previously Unrecognized Distortions of FD Calculations Having established the possibility of differences in motion estimates for multi-band data as compared to single-band data, the respiratory traces and power spectra between the two data types were subsequently compared. FIG. 21A shows the estimates in a single representative subject, whereby the respiration data were resampled to match the sampling rate of the BOLD data—in this case a TR of 800 ms. To facilitate comparisons by visual inspection, plots were provided with timecourses for motion estimates on each one of the six directions of the rigid body registration parameters on top of the respiration rate signal. Side-by-side spectra are also provided for those signals in FIG. 21A. The center row of FIG. 21A provides the full trace of a run for a subject, and the first row of FIG. 21A provides a small screen-shot of 10 frames of that same run. FIG. 21A shows a trend for the motion trace to follow in some respect the respiratory trace. This correspondence occurs in several directions, but in particular, the y-direction (e.g., the phase encoding direction).

The bottom row of FIG. 21A confirms this association by plotting the power spectrum for both the motion traces and the respiratory trace across runs for the same subject. The peak amplitude of the respirations, matches the peak amplitude of the motion trace. Importantly, while the largest 'bump' occurs in the y-direction (again, the phase encoding direction, as would be expected) the artifact appears to 'bleed' into other directions as well. This may relate to the fact that the relative head position of the subject often changes from the beginning to the end of a run.

FIG. 21B illustrates the power spectrum across all subjects ranked from those having the lowest motion to those having the highest motion. FIG. 21B shows that the artifact is present in most subjects, as shown by the arrows on the y-direction and z-direction. In many subjects, the artifact is also present in multiple directions, albeit to a lesser extent. It appears that for participants who move most in the scanner (e.g., bottom of FIG. 21B), the artifact is reduced. This phenomenon is likely secondary to having reduced contributions to the power spectra from respirations relative to movement for a given subject.

Single-Band FD Values Also have the Same Respiration Artifact

FIGS. 22A-22G show the same data as shown in FIGS. 21A and 21B, but with single-band (e.g., single shot) acquisition data. For these data, respiration data was not available. It can be seem from the single shot data that similar types of artifacts shown with multiband data exist for single shot data. Specifically, FIG. 22B illustrates that the artifacts primary occur in the Y-direction (e.g., the phase encode direction). However, the profile of the power spectra appears to be much wider and less specific (e.g., the peak in the power is quite broad).

This phenomenon is likely secondary to the fact that the slower sampling rate of single shot data (e.g., the TR) is not fast enough to capture the true rate of the respirations. Rather, respirations are being aliased into other frequencies. This effect is illustrated in FIGS. 22C-22G. Any signal that has a frequency higher than half the sampling rate (e.g., the Nyquist limit) will be erroneously detected as a signal of lower frequency. For example, a 2 Hz signal sampled at 10 Hz will read out at 2 Hz. A 5 Hz signal sampled a 10 Hz, will read out at 5 Hz because it is exactly at the Nyquist limit. However, a 6 Hz signal sampled at 10 Hz, will not read out as 6 Hz, but will rather read out at a lower sampling frequency. In this example, the signal was be read out as 4 Hz because the signal is higher than Nyquist limit.

FIGS. 22C-22G provide an illustration of what frequencies might be expected for a given respiratory rate and for a given TR (e.g., sampling rate). FIG. 22C illustrates three examples of 15, 20, and 25 breaths per minute. It can be seen from FIG. 22E that the artifact in the motion traces for a TR of 800 ms (or 0.8 s) will likely match the true respiratory rate of a given participant; however, for slower TRs as shown by FIGS. 22F and 22G, the respiratory rate will be aliased into different frequencies. Thus, any variation in respiratory rate during a scan are likely to be spread into various frequencies, widening a given profile, as shown in FIG. 22A. This mismatch between true respiratory rate and what is observed in motion traces might be one reason why these artifacts in motion data have not been previously reported on single shot data until now.

FIGS. 23A-23E show BOLD data for a subject breathing at a very specific respiratory rate of 0.33 Hz. Data was collected using the identical multiband sequence at TR=0.8 ms, 1.5 s, and 2 s. Data was also collected using single shot data at TR=2.5 s. What can be seen in the supplementary material is that aliasing of the respiratory signals matches closely to the theoretical values outlined in FIGS. 22C-22G.

Example 4 Summary

The results of these experiments demonstrated the effects of respirations on motion estimates. More specifically, the results demonstrated that respirations contaminate movement estimates in fMRI. Qualitative observations highlighted a fundamental difference in motion traces produced by multiband data compared to single-band data. Further, multiband imaging, with its faster repetition times and improved spatial resolution, revealed previously unrecognized distortions of FD calculations. Additionally, single shot FD values were shown to have the same respiration artifact, albeit to a lesser extent.

Example 5: Evaluation of FIRMM System Integrated with Notch Filters to Remove Distortions Caused by Respirations in Head Motion Data Having established the effects of respirations on motion estimates in Example 4, the following experiments were conducted to validate the FIRMM head motion prediction method integrated with notch filters on head motion data distorted by respirations. A subject's breathing (e.g., respirations) causes artifacts in motion estimates obtained from traditional frame alignment procedures during preprocessing and/or real-time monitoring. The effects of these artifacts can have detrimental effects on connectivity related outcomes. To correct the undesired signal(s) in the motion estimates, a notch filter having two design parameters, a central cutoff frequency and a bandwidth, was designed based on the distribution of respiration rate from data provided by the Adolescent Brain and Cognitive Development (ABCD) study. The designed filters (e.g., a general filter and a subject specific filter) were implemented on both multiband and single-band (e.g., single shot) data, and were integrated with the FIRMM head motion prediction method, disclosed above, to remove undesired signal(s) corresponding to the subject's respiration rate.
Evaluation Data Acquisition Parameters The same ABCD study participants of dataset 4 and neurotypical control participants of dataset 5 as described in Example 4 participated in the experiments of Example 5. ABCD and Neurotypical control participants were scanned in the same method, and on the same equipment as described above in Example 4.

Results

Filtering FD Traces Corrects for Respiratory Artifacts and Improves Estimation of BOLD Data Quality The notch filter was applied in two ways. First, a general filter was generated in order to capture a wide range of possible respiratory rates. The general filter was designed to capture a large portion of the ABCD sample population respiration peak with respect to power. This filter worked well in improving the connectivity outcomes. Second, a subject specific filter was designed to produce filter parameters specific to a subject's respiratory belt data. The subject specific filter performed slightly better than the general filter. FIG. 24A illustrates the results of no filter application and FIG. 24B illustrates the results of implementing a general notch filter using BOLD Visualization Data (BVD) plots. FIG. 24C illustrates the results of no filter application for data obtained from a medium moving ABCD participant. FIG. 24D illustrates the results of applying a general notch filter to the data obtained from the same medium moving ABCD participant shown in FIG. 24C.

It can be seen from FIGS. 24B and 24D that application of the general filter reduces motion estimates. The motion traces, as measured with FD, appears to more accurately reflect the motion artifact in the actual data. This is illustrated in the "post-regression" grey plots of FIGS. 24B and 24D. Considering the field's general standard of a FD cutoff of <0.2 mm, one can see that the frames above this threshold more closely align with post-regression motion artifacts, as demonstrated by the strips in grey plots and the spikes in the "post all" DVARS lines.

Further, the amount of variance as measured by DVARS, as shown by "post all" DVARS and "std" in plots of FIGS. 24B and 24D, appears to be slightly reduced when using the motion filter. This result likely reflects the closer correspondence of the motion values (e.g., translation and rotation numbers) to the actual motion artifacts when regressing out motion from the signal. In other words, the linear model fit that is used to regress motion from the bold signal is stronger in the absence of the artifact induced by respirations.

FIGS. 25A and 25B show results with the general filter application, and FIGS. 9A and 9B show results with the subject specific filter application. More specifically, FIGS. 25A and 25B show respiratory traces and power spectra between multi-band data and single-band data. FIGS. 25A and 25B provide the replicates of FIGS. 21A and 21B discussed above, after the general and subject specific filters have been applied. Both FIGS. 25B (general filter) and 26B (specific filter) disclose that methods implementing the general filter and subject specific filters do not perfectly capture the artifacts caused by respiration. As shown in FIGS. 26A and 26B, particularly for high moving subjects (e.g., bottom of the graph), the filter may be impinging on true motion values.
Filtered Estimates Provide Improved Data Quality FIGS. 27A-27L and FIG. 28 illustrate that quantitative measurements relating motion estimates to connectivity data suggest that filtered estimates provide improved data quality. The interpretation of FIGS. 27A-27L are that if the FD traces are accurately representing movement in the BOLD data, then the curves should be shifted to the left. This result would arise, because in the optimal case, where FD is perfectly accurate at depicting true movement in the scanner, the baseline measurement (the highest quality frames) would have very little movement. Thus, when compared to frames that have higher movement, divergence will quickly ensue (e.g., will quickly become divergent from random). In the case where FD is randomly associated with true movement in the BOLD, there will be no divergence because the baseline measurement will have an equal (or similar) amount of movement frames compared to the other measurements (see FIGS. 20A-20C). In short, the FD measurements that are most accurate should skew leftward relative to the others.

FIGS. 27A-27L show that FD measurements appear most random when no filter is used as opposed to FD measurements that use a general filter or a run-specific filter. This can be visualized with fewer 'light grey' points shown in FIGS. 27A and 27D along with a shift to the left of the cumulative distribution for FIGS. 27G and 27J. The subject specific filter, as shown in FIGS. 27C, 27F, 27I, and 27L, produced largely overlapping distributions with the general filter, as shown in FIGS. 27B, 27E, 27H, and 27K. Further, as shown in FIG. 28, kstest2 was used to test significant differences between CDFs. FIG. 28 illustrates that the difference between No Filter and General Filter is significantly different (p<0.0001). The kstest2 also showed the CDF of the Run Specific Filter compared to the General Filter to also be significantly different (p<0.0001).

Real-Time Integration of the Notch Filter with the FIRMM Head Motion Prediction Method Provides More Accurate Motion Data The notch filtering approach was directly integrated into FIRMM. Integration of the notch filter into FIRMM provided scanner operators and research investigators with (a) the option of applying the notch filter in real time and (b) inputting their own filter parameters, as shown in FIGS. 29A and 29B. FIGS. 29A and 29B show a screen-shot of a display provided by FIRMM to an operator computing device such as operator computing device 910 (shown in FIG. 9). More specifically, FIG. 29A shows a display for unfiltered data of a subject with three 5 minute resting runs. FIG. 29B shows a display for filtered data of the same subject with three 5 minute resting runs. The design of the real-time filter was generated to closely match post-processing numbers. As shown in FIGS. 29C and 29D, the filtered FD numbers (FIG. 29D) closely match the post-processing numbers.

Further, the FIRMM head motion prediction method enabled the notch filter to be turned on and off, which provided scanner operators and investigators the ability to tailor MRI scans according to a subject's needs, population (e.g., special populations like infants might not need the notch filter), and/or research objective.

Example 5 Summary

The results of these experiments demonstrated the validity of the disclosed approach that integrates a notch filter with the FIRMM head motion prediction method. The notch filter-integrated FIRMM head motion prediction method was effective in filtering FD traces to correct respiratory artifacts, and improve estimations of BOLD data quality. Further, quantitative measurements relating motion estimates to connectivity data suggest that filtered estimates provide improved data quality. Additionally, integrating the notch filter with the FIRMM head motion prediction method in real-time provided more accurate head motion data, and provided scanner operators with increased options in setting their own filters during real-time MRI scans.

It is to be understood that the configurations and/or approaches described herein are exemplary in nature, and that these specific aspects or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and sub-combinations of the various processes, systems and configurations, and other features, functions, acts, and/or properties disclosed herein, as well as any and all equivalents thereof.

What is claimed is:

1. A computer-implemented method for monitoring movement of a patient undergoing a magnetic resonance imaging (MRI) scan by aligning MRI data, the method implemented on a computing device including at least one processor in communication with at least one memory device, the computing device in communication with an MRI system, the method including steps comprising:
   a) receiving, by the computing device, a data frame from the MRI system acquired during the MRI scan;
   b) aligning, by the computing device, the received data frame to a reference image;
   c) calculating, by the computing device, motion of at least a portion of the patient between the received data frame and the reference image;
   d) providing stimulus to the patient, by the computing device, wherein the stimulus includes a task to be performed by the patient during the MRI scan and sensor feedback indicating the motion of the at least a portion of the patient; and
   e) repeating steps a) through d) during the MRI scan to make the stimulus interactive with the patient to perform the task while controlling the motion of the patient.

2. The method of claim 1, further comprising acquiring feedback from the patient, by the computing device, using at least one of manually actuated buttons, switches, keyboards, mice, game controllers, cameras, microphones, or touch screens accessible to the patient during the MRI scan.

3. The method of claim 1, wherein the stimulus includes a game communicated to the patient during the MRI scan.

4. The method of claim 3, wherein the game includes gameplay that indicates when the motion of the at least a portion of the patient is above a threshold or when a lack of motion satisfies a hold still threshold.

5. The method of claim 1, wherein the stimulus includes a movie.

6. The method of claim 5, wherein step e) includes obscuring the movie to indicate when the motion of the at least a portion of the patient is above a threshold or when a lack of motion satisfies a hold still threshold.

7. The method of claim 1, further comprising:
   identifying, by the computing device, the motion of the at least a portion of the patient relative to the reference image using six frame alignment parameters, wherein the six frame alignment parameters are x, y, z, $\theta_x$, $\theta_y$, and $\theta_z$;
   calculating, by the computing device, a frame displacement using at least the data frame including the motion of at least a portion of the patient and the six frame alignment parameters; and
   displaying, by the computing device, the frame displacement for each frame in real time to at least one of an operator of the MRI system or to the patient with the stimulus.

8. The method of claim 1, wherein the task and the sensory feedback are provided to the patient simultaneously.

9. The method of claim 1, further comprising:
   predicting, by the computing device, a number of usable frames available upon completion of the MRI scan; and
   displaying, by the computing device, the predicted number of usable frames to at least one of an operator of the MRI system or the patient in real time as the patient is receiving the stimulus.

10. The method of claim 9, wherein predicting the number of usable frames comprises applying a linear model (y=mx+b), wherein y is a predicted number of usable frames available upon completion of the scan, x is a consecutive frame count, and m and b are estimations for each subject in real time.

11. The method of claim 1, further comprising:

predicting, by the computing device, a duration of scanning sufficient to achieve a predetermined number of usable frames, each usable frame comprising a frame with a frame displacement caused by the motion falling below a predetermined threshold; and displaying, by the computing device, the predicted duration of scanning to at least one of an operator of the MRI system or the patient as part of the stimulus.

12. The method of claim 1, wherein aligning the received data frame to the reference image comprises calculating a series of rigid body transforms, Ti, wherein i indexes a spatial registration of the received data frame to the reference image, wherein each of the series of rigid body transforms is calculated by minimizing a registration error:

$$\varepsilon_i = \left\langle \left( sI_i\left( T(\vec{x}) \right) - I_1(\vec{x}) \right)^2 \right\rangle$$

such that $I(\vec{x})$ is a frame intensity at locus $\vec{x}$ and s is a scalar factor that compensates for fluctuations in mean signal intensity.

13. The method of claim 12, wherein each of the series of rigid body transforms is represented by a combination of rotations and displacements, $$T_i = \begin{bmatrix} R_i & \dot{d}_i \\ 0 & 1 \end{bmatrix}$$

wherein Ri represents a 3×3 matrix of rotations, $\dot{d}_i$ represents a 3×1 column vector of displacements, and wherein $R_i$ represents three elementary rotations at each axis.

14. The method of claim 1, further comprising:

generating, by the computing device, summary counts in real-time of a number of high-quality low-movement frames acquired during the MRI scan; and transmitting the generated summary counts to at least one of a scanner operator or the patient.

15. A system comprising:

a computing device including a memory device and a processor, the memory device storing instructions that configure the computing device to:

receive a data frame from a magnetic resonance imaging (MRI) system performing an MRI scan of a patient;

compare the data frame to a reference image to assess motion of a body part of the patient during the MRI scan;

generate sensory feedback to be communicated to the patient during the MRI scan based on the motion of the body part of the patient during the MRI scan; and adjust the sensory feedback during the MRI scan as the motion of the body part of the patient changes; and a feedback device configured to provide stimulus to the patient during the MRI scan, wherein the stimulus includes a task as part of at least one of a game, a movie, a cartoon, a shape, or an auditory signal.

16. The system of claim 15, wherein the computing device is further configured to align the received data frame to the reference image and calculate the motion of the body part of the patient between the received data frame and the reference image.

17. The system of claim 15, wherein the feedback device includes at least one of manually actuated buttons, switches, keyboards, mice, game controllers, cameras, microphones, or touch screens accessible to the patient during the MRI scan.

18. The system of claim 15, wherein the stimulus comprises the game, and the game includes gameplay that indicates when the motion of the body part of the patient is above a threshold or when a lack of motion satisfies a hold still threshold.

19. A computer-implemented method for monitoring movement of a patient undergoing a magnetic resonance imaging (MRI) scan by aligning MRI data, the method implemented on a computing device including at least one processor in communication with at least one memory device, the computing device in communication with an MRI system, the method comprising:

receiving a data frame from the MRI system performing the MRI scan of the patient;

comparing the data frame to a reference image to assess motion of a body part of the patient during the MRI scan;

generating stimulus to be communicated to the patient during the MRI scan based on a task of the MRI scan and the motion of the body part of the patient during the MRI scan;

adjusting the stimulus during the MRI scan to adjust the task and as the motion of the body part of the patient changes; and communicating the stimulus to the patient during the MRI scan, wherein the sensory feedback includes at least one of a game, a movie, a cartoon, a shape, or an auditory signal.

20. The method of claim 19, further comprising receiving feedback from the patient from at least one of manually actuated buttons, switches, keyboards, mice, game controllers, cameras, microphones, or touch screens accessible to the patient during the MRI scan.

* * * * *